(12) United States Patent
Bobrowicz et al.

(10) Patent No.: US 7,259,007 B2
(45) Date of Patent: Aug. 21, 2007

(54) METHODS FOR ELIMINATING MANNOSYLPHOSPHORYLATION OF GLYCANS IN THE PRODUCTION OF GLYCOPROTEINS

(75) Inventors: Piotr Bobrowicz, White River Junction, VT (US); Terrance A. Stadheim, White River Junction, VT (US); Stefan Wildt, Lebanon, NH (US)

(73) Assignee: GlycoFi, Inc., Lebanon, NH (US)

( * ) Notice: Subject to any disclaimer, the term of this patent is extended or adjusted under 35 U.S.C. 154(b) by 0 days.

(21) Appl. No.: 11/020,808

(22) Filed: Dec. 22, 2004

(65) Prior Publication Data

US 2006/0160179 A1 Jul. 20, 2006

Related U.S. Application Data

(60) Provisional application No. 60/532,461, filed on Dec. 24, 2003.

(51) Int. Cl.
*G01N 1/10* (2006.01)
*C12P 21/06* (2006.01)
*C12H 21/04* (2006.01)
*C12N 1/18* (2006.01)

(52) U.S. Cl. ............... 435/255.5; 435/255.1; 435/254.2; 435/254.23; 435/69.1; 435/483

(58) Field of Classification Search .................. None
See application file for complete search history.

(56) References Cited

U.S. PATENT DOCUMENTS

2002/0137134 A1* 9/2002 Gerngross ................ 435/69.1

FOREIGN PATENT DOCUMENTS

| EP | 1 283 265 A1 | 5/2001 |
| WO | WO 01/88143 * | 2/2001 |
| WO | WO 01/88143 A1 | 11/2001 |

OTHER PUBLICATIONS

Antebi, et al., "The Yeast Ca2+-ATPase Homologue, PMR1, is Required for Normal Golgi Function and Localizes in a Novel Golgi-like Distribution", Molecular Biology of the Cell, vol. 3, pp. 633-654, Jun. 1992.
Ballou, et al., "Isolation, Characterization, and Properties of Saccharomyces cerevisiae mnn Mutants with Nonconditional Protein Glycosylation Defects", Methods In Enzymology, vol. 185, pp. 440-470, 1990.
Choi, et al., "Use of combinatorial genetic libraries to humanize N-linked glycosylation in the yeast *Pichia pastoris*", PNAS, vol. 100, No. 9, pp. 5022-5027, Apr. 29, 2003.
Davidson, et al., "A PCR-based strategy to generate integrative targeting alleles with large regions of homology", Microbiology, vol. 148, pp. 2607-2615, 2002.
Dean, et al., "The VRG4 Gene is Required for GDP-mannose Transport into the Lumen of the Golgi in the Yeast, *Saccharomyces cerevisiae*", The Journal of Biological Chemistry, vol. 272, No. 50, pp. 31908-31914, 1997.
Goldstein, et al., "Three New Dominant Drug Resistance Cassettes for Gene Disruption in *Saccharomyces cerevisiae*", Yeast, vol. 15, pp. 1541-1553, 1999.
Hamilton, et al., "Production of Complex Human Glycoproteins in Yeast", Science, vol. 301, pp. 1244-1246, 2003.
Hunter, et al., "The protein kinases of budding yeast: six score and more", Trends in Biochemical Science, vol. 22, pp. 18-22, Jan. 1997.
Jigami, et al., "Mannosylphosphate transfer to yeast mannan", Biochimica et Biophysica Acta, vol. 1426, pp. 335-345, 1999.
Kukuruzinska, et al., "Protein Glycosylation in Yeast", Ann. Rev. Biochem., vol. 56, pp. 915-944, 1987.
Lussier, et al., "The Ktr1p, Ktr3, and Kre2p/Mnt1p Mannosyltransferases Participate in the Elaboration of Yeast O- and N-linked Carbohydrate Chains", The Journal of Biological Chemistry, vol. 272, No. 24, pp. 15527-15531, 1997.
Miele, et al., "Characterization of the acidic oligosaccharides addembled on the Pichia pastoris-expressed recombinant kringle 2 domain of human tissue-type plasminogen activator", Biotechnology and Applied Biochemistry, vol. 27, pp. 79-83, 1997.
Miura, et al., "Cloning and characterization in *Pichia pastoris* of PNO1 gene required for phosphomannosylation of N-linked oligosaccharides", Gene, vol. 324, pp. 129-137, 2004.
Montesino, et al., "Variation in N-Linked Oligosaccharide Structures on Heterologous Proteins Secreted by the Methylotrophic Yeast *Pichia pastoris*", Protein Expression and Purification, vol. 14, pp. 197-207, 1998.
Odani, et al., "Cloning and analysis of the MNN4 gene required for phosphorylation of N-linked oligosaccharides in *Saccharomyces cerevisiae*", Glycobiology, vol. 6, No. 8, pp. 805-810, 1996.
Pullen, et al., "CD40 Signaling through Tumor Necrosis Factor Receptor-associated Factors (TRAFs)," Journal of Biological Chemistry, vol. 274, No. 20, pp. 14246-14254, 1999.
Rayner, et al., "Identification of the MNN2 and MNN5 Mannosyltransferases Required for Forming and Extending the Mannose Branches of the Outer Chain Mannans of *Saccharomyces cerevisiae*", Journal of Biological Chemistry, vol. 273, No. 41, pp. 26836-26843, 1998.
Rosenfeld, et al., "Genetic Control of Yeast Mannan Structure", Journal of Biological Chemistry, vol. 249, No. 7, pp. 2319-2321, 1974.
Wang, et al., "MNN6, a Member of the KRE2/MNT1 Family, Is the Gene for Mannosylphosphate Transfer in *Saccharomyces cerevisiae*", Journal of Biological Chemistry, vol. 272, No. 29,1 pp. 18117-18124, 1997.

* cited by examiner

*Primary Examiner*—Rebecca E. Prouty
*Assistant Examiner*—Mohammad Meah
(74) *Attorney, Agent, or Firm*—John David Reilly; William Krovatin

(57) ABSTRACT

The present invention relates to the elimination of mannosylphosphorylation on the glycans of glycoproteins in the yeast genus *Pichia*. The elimination of mannosylphosphorylated glycoproteins results from the disruption of the PNO1 gene and the newly isolated *P. pastoris* MNN4B gene. The present invention further relates to methods for producing modified glycan structures in host cells that are free of glycan mannosylphosphorylation.

5 Claims, 25 Drawing Sheets

Figure 1A

```
   1 ATG AAA GTA TCA AAG CGG TTG ATA CCG AGG AGA TCT CGT CTC CTC ATT ATG ATG ATG CTA CTG GTT GTT
   1▶ M   K   V   S   K   R   L   I   P   R   R   S   R   L   L   I   M   M   M   L   L   V   V
  70 TAC CAG CTG GTG GTT TTG GTC CTA GGA TTG GAG AGC GTC TCT GAA GGA AAA TTA GCA AGC TTG CTT GAC
  24▶ Y   Q   L   V   V   L   V   L   G   L   E   S   V   S   E   G   K   L   A   S   L   L   D
 139 TTG GGC GAT TGG GAT CTA GCT AAC TCC TCG CTA TCT ATA TCC GAT TTC ATA AAG CTG AAG CTC AAA GGC
  47▶ L   G   D   W   D   L   A   N   S   S   L   S   I   S   D   F   I   K   L   K   L   K   G
 208 CAA AAG ACT TAT CAC AAA TTT GAT GAA CAT GTC TTC GCC GCA ATG GCA AGA ATT CAA AGT AAT GAG AAT
  70▶ Q   K   T   Y   H   K   F   D   E   H   V   F   A   A   M   A   R   I   Q   S   N   E   N
 277 GGC AAG TTG GCG GAT TAC GAG TCT TCA ACT GAC GTA ACC ATT CAA AAT GTT GAA CTT TGG
  93▶ G   K   L   A   D   Y   E   S   T   S   S   K   T   D   V   T   I   Q   N   V   E   L   W
 346 AAG AGA TTG AGC GAA GAA GAA TAC ACT TAC GAA CCG CGG ATA ACT TTG GCT GTG TAT CTG AGC TAC ATT
 116▶ K   R   L   S   E   E   E   Y   T   Y   E   P   R   I   T   L   A   V   Y   L   S   Y   I
 415 CAT CAG AGG ACT TAT GAC AGG TAC GCG ACT AGT TAC GCT CCT TAT AAC TTG CGG GTG CCT TTT TCG TGG
 139▶ H   Q   R   T   Y   D   R   Y   A   T   S   Y   A   P   Y   N   L   R   V   P   F   S   W
 484 GCT GAC TGG ATA GAT CTG ACG GCC CTA AAT CAA TAC TTG GAT AAA ACG AAA GGC TGC GAG GCA GTT TTC
 162▶ A   D   W   I   D   L   T   A   L   N   Q   Y   L   D   K   T   K   G   C   E   A   V   F
 553 CCT AGA GAA AGT GAG GCA ACT ATG AAG CTT AAC AAT ATC ACT GTT GTG GAC TGG CTT GAG GGC CTT TGC
 185▶ P   R   E   S   E   A   T   M   K   L   N   N   I   T   V   V   D   W   L   E   G   L   C
 622 ATA ACT GAT AAA TCA CTT CAA AAT TCC GTA AAC TCC ACA TAT GCG GAA GAG ATT AAT AGT CGG GAC ATC
 208▶ I   T   D   K   S   L   Q   N   S   V   N   S   T   Y   A   E   E   I   N   S   R   D   I
 691 TTG TCT CCT AAC TTC CAT GTG TTT GGT TAT TCT GAT GCT AAA GAT AAT CCT CAG CAA AAA ATC TTT CAA
 231▶ L   S   P   N   F   H   V   F   G   Y   S   D   A   K   D   N   P   Q   Q   K   I   F   Q
 760 TCT AAA TCT TAT ATC AAC TCA AAG CTG CCG CTC CCA AAA AGT TTG ATA TTT TTA ACA GAT GGA GGT AGT
 254▶ S   K   S   Y   I   N   S   K   L   P   L   P   K   S   L   I   F   L   T   D   G   G   S
 829 TAC GCT TTG ACA GTC GAC CGA ACT CAA ATT AAA AGA ATT CTA AAA TCT GGC CTG CTT TCA CAC TTT TTC
 277▶ Y   A   L   T   V   D   R   T   Q   N   K   R   I   L   K   S   G   L   L   S   H   F   F
 898 TCA AAG AAA AAG AAG GAA CAC AAT CTG CCT CAA GAC CAA AAA ACT TTC ACG TTT GAC CCC GTA TAC GAA
 300▶ S   K   K   K   K   E   H   N   L   P   Q   D   Q   K   T   F   T   F   D   P   V   Y   E
 967 TTC AAT AGA CTG AAA TCT CAG GTC AAG CCC CGT CCA ATA TCT TCA GAA CCT AGT ATT GAT TCT GCT TTG
 323▶ F   N   R   L   K   S   Q   V   K   P   R   P   I   S   S   E   P   S   I   D   S   A   L
1036 AAG GAA AAT GAC TAC AAG CTT AAA CTG AAA GAG TCG TCG TTT ATT TTT AAT TAC GGA AGG ATT CTT TCG
 346▶ K   E   N   D   Y   K   L   K   L   K   E   S   S   F   I   F   N   Y   G   R   I   L   S
1105 AAC TAT GAA GAG CGG CTT GAG AGT CTA AAT GAC TTC GAG AAA TCG CAC TAC GAG TCC TTA GCT TAT TCC
 369▶ N   Y   E   E   R   L   E   S   L   N   D   F   E   K   S   H   Y   E   S   L   A   Y   S
1174 TCC TTG TTA GAG GCA AGA AAG TTG CCC AAG TAT TTC GGC GAA GTT ATA TTG AAG AAC CCA CAA GAT GGT
 392▶ S   L   L   E   A   R   K   L   P   K   Y   F   G   E   V   I   L   K   N   P   Q   D   G
1243 GGA ATT CAT TAT GAT TAC AGA TTC TTC AGC GGA CTC ATT GAT AAA ACT CAG ATA AAT CAT TTT GAG GAT
 415▶ G   I   H   Y   D   Y   R   F   F   S   G   L   I   D   K   T   Q   I   N   H   F   E   D
1312 GAG ACT GAA AGA AAG AAG ATA ATC ATG CGT AGA CTT CTT CGA ACT TGG CAG TAC TTC ACG TAT CAC AAT
 438▶ E   T   E   R   K   K   I   I   M   R   R   L   L   R   T   W   Q   Y   F   T   Y   H   N
1381 AAC ATT ATC AAT TGG ATC TCG CAC GGT TCT TTA CTG TCA TGG TAT TGG GAT GGA CTT TCT TTT CCA TGG
 461▶ N   I   I   N   W   I   S   H   G   S   L   L   S   W   Y   W   D   G   L   S   F   P   W
1450 GAC AAT GAC ATT GAC GTA CAA ATG CCC ATA ATG GAG CTG AAT AAC TTC TGC AAA CAG TTC AAC AAT TCT
 484▶ D   N   D   I   D   V   Q   M   P   I   M   E   L   N   N   F   C   K   Q   F   N   N   S
1519 CTG GTC GTG GAG GAT GTT TCT CAA GGG TTT GGC AGA TAC TAC GTT GAT TGC ACG AGC TTC CTG GCC CAG
 507▶ L   V   V   E   D   V   S   Q   G   F   G   R   Y   Y   V   D   C   T   S   F   L   A   Q
1588 AGA ACG CGA GGT AAT GGT AAC AAC AAC ATT GAT GCC CGT TTT ATT GAT GTG TCG TCT GGT CTC TTC ATT
 530▶ R   T   R   G   N   G   N   N   N   I   D   A   R   F   I   D   V   S   S   G   L   F   I
1657 GAC ATT ACG GGT TTG GCT TTG ACT GGA TCA ACA ATG CCC AAA AGA TAC TCC AAT AAG CTG ATA AAA CAA
 553▶ D   I   T   G   L   A   L   T   G   S   T   M   P   K   R   Y   S   N   K   L   I   K   Q
1726 CCG AAA AAA TCT ACC GAC TCA ACA GGA TCG ACT CCT GAG AAC GGA CTC ACT AGA AAC TTG AGG CAA AAT
 576▶ P   K   K   S   T   D   S   T   G   S   T   P   E   N   G   L   T   R   N   L   R   Q   N
1795 TTG AAT GCA CAA GTT TAC AAC TGT AGA AAC GGT CAT TTT TAC CAA TAC TCG GAG CTA TCT CCT TTG AAG
 599▶ L   N   A   Q   V   Y   N   C   R   N   G   H   F   Y   Q   Y   S   E   L   S   P   L   K
1864 TTG TCG ATA GTA GAA GGT GCA CTC ACC CTA ATA CCC AAC GAT TTT GTT ACT ATA TTG GAA ACT GAG TAC
 622▶ L   S   I   V   E   G   A   L   T   L   I   P   N   D   F   V   T   I   L   E   T   E   Y
1933 CAA AGG AGA GGT CTT GAA AAG AAC ACA TAT GCG AAG TAT CTC TAC GTT CCA GAG CTT CGA CTT TGG ATG
 645▶ Q   R   R   G   L   E   K   N   T   Y   A   K   Y   L   Y   V   P   E   L   R   L   W   M
2002 TCA TAC AAT GAC ATC TAT GAT ATC TTG CAA GGT ACT AAT AGT CAT GGC CGT CCT TTA TCT GCA AAG ACA
 668▶ S   Y   N   D   I   Y   D   I   L   Q   G   T   N   S   H   G   R   P   L   S   A   K   T
2071 ATG GCG ACT ATC TTT CCT CGG TTA AAC TCT GAC ATT AAT CTA AAA AAG TTT TTG CGC AAT GAT CAT ACT
 691▶ M   A   T   I   F   P   R   L   N   S   D   I   N   L   K   K   F   L   R   N   D   H   T
2140 TTT AAG AAC ATT TAT TCT ACT TTC AAC GTG ACA CGA GTG CAC GAG GAG GAA CTG AAG CAT TTG ATA GTA
 714▶ F   K   N   I   Y   S   T   F   N   V   T   R   V   H   E   E   E   L   K   H   L   I   V
2209 AAC TAT GAC CAA AAT AAA CGG AAG TCG GCT GAG TAC AGG CAG TTC TTG GAA AAC TTG CGG TTT ATG AAT
 737▶ N   Y   D   Q   N   K   R   K   S   A   E   Y   R   Q   F   L   E   N   L   R   F   M   N
```

Figure 1ß

```
2278 CCA ATC AGA AAA GAT CTG GTG ACT TAC GAG AGT AGG TTG AAG GCT CTT GAT GGA TAC AAT GAG GTC GAA
760▶ P   I   R   K   D   L   V   T   Y   E   S   R   L   K   A   L   D   G   Y   N   E   V   E
2347 GAA TTA GAA AAG AAG CAA GAG AAT AGG GAA AAA GAA AGA AAG GAG AAG AAG GAA AAG GAG GAA AAA GAG
783▶ E   L   E   K   K   Q   E   N   R   E   K   E   R   K   E   K   K   E   K   E   E   K   E
2416 AAG AAG GAA AAG GAG GAA AAA GAG AAG AAG GAA AAG GAA GAA AAG GAA AAG AAG GAA AAG GAA GAA AAG
806▶ K   K   E   K   E   E   K   E   K   K   E   K   E   E   K   E   K   K   E   K   E   E   K
2485 GAG AGG AAA GAG AAG GAA GAA AAG GAA GAA TAT GAA GAA GAC GAT AAT GAG GGC GAA CAA CCA ACA GAA
829▶ E   R   K   E   K   E   E   K   E   E   Y   E   E   D   D   N   E   G   E   Q   P   T   E
2554 CAA AAG AGC CAG CAG GAG GCT AAA GAA TAG
852▶ Q   K   S   Q   Q   E   A   K   E
```

Figure 2

```
   1 ATG TTC AAA GAA ACG TCA AAG AAC TTG TTT GGT TCG ATA AAT ACC TTC AAT ACG GTG GAG TAT GTC ATG
   1▶ M   F   K   E   T   S   K   N   L   F   G   S   I   N   T   F   N   T   V   E   Y   V   M
  70 TAT ATG ATG CTA CTA CTG ACT GCG TAT TTT TTG AAC CAC CTG TTG CAT AGT TTG GAT AAC ATC AAT CAT
  24▶ Y   M   M   L   L   L   T   A   Y   F   L   N   H   L   L   H   S   L   D   N   I   N   H
 139 TTG GTT GAG TCT GAT GTT AAT TAT CAA CTA CTT CAA AGG GTA ACA AAT AAA GTC AAG CTT TTT GAT GAG
  47▶ L   V   E   S   D   V   N   Y   Q   L   L   Q   R   V   T   N   K   V   K   L   F   D   E
 208 GAA GCA GTC TTG CCC TTT GCT AAG AAT CTC AAT AGA AGA ACT GAA CGC TTT GAT CCA AGG TTG CCT GTA
  70▶ E   A   V   L   P   F   A   K   N   L   N   R   R   T   E   R   F   D   P   R   L   P   V
 277 GCT GCA TAC CTT CGA AGC CTT CAA GAT CAG TAT TCG GAG CTT CCA CAA GGT ACC GAC CTG AAT GAT ATT
  93▶ A   A   Y   L   R   S   L   Q   D   Q   Y   S   E   L   P   Q   G   T   D   L   N   D   I
 346 CCG CCC CTG GAG GTT TCT TTC CAC TGG GAT GAC TGG TTA AGT TTG GGA ATT GCA TCA ACC TTT TGG GAC
 116▶ P   P   L   E   V   S   F   H   W   D   D   W   L   S   L   G   I   A   S   T   F   W   D
 415 GCC TTC GAC AAT TAC AAC AAG AGA CAA GGA GAA AAT GCA ATT TCT TAC GAG CAG CTC CAA GCA ATA CTT
 139▶ A   F   D   N   Y   N   K   R   Q   G   E   N   A   I   S   Y   E   Q   L   Q   A   I   L
 484 GTT AAT GAT TTG GAA GAT TTT tCT CCC TAC ACC GCA CAT ATT CTT CAC AGT AAC GTG GAA GTC TAC AAA
 162▶ V   N   D   L   E   D   F   S   P   Y   T   A   H   I   L   H   S   N   V   E   V   Y   K
 553 TAC AGA ACG ATT CCT CAA AAG ATC GTC TAT ATG TCA AAC AAG GGC TAT TTT GAA CTC TTG GTA ACC GAA
 185▶ Y   R   T   I   P   Q   K   I   V   Y   M   S   N   K   G   Y   F   E   L   L   V   T   E
 622 AAG GAA AAA CTA TCC AAT GAG GGT CTC TGG AGC ATT TTC CAT CAG AAA CAA GGT GGA CTT AAC GAA TTC
 208▶ K   E   K   L   S   N   E   G   L   W   S   I   F   H   Q   K   Q   G   G   L   N   E   F
 691 AGT AGT CTC AAT CTC ATA GAG GAG GTT GAT GCG TTG GAT GAA ATC TAT GAT TCC AAA GGG TTG CCT GCT
 231▶ S   S   L   N   L   I   E   E   V   D   A   L   D   E   I   Y   D   S   K   G   L   P   A
 760 TGG GAT CCT CCC TTC CCT GAG GAA CTT GAT GCT TCA GAT GAA GAT TTC AAG TTC AAT GCC ACA GAA GAA
 254▶ W   D   P   P   F   P   E   E   L   D   A   S   D   E   D   F   K   F   N   A   T   E   E
 829 CTG GCA AAG GTA GAG CAA ATC AAA GAA CCA AAG CTG GAA GAC ATA TTC TAT CAG GAA GGA CTG CAA CAC
 277▶ L   A   K   V   E   Q   I   K   E   P   K   L   E   D   I   F   Y   Q   E   G   L   Q   H
 898 GGG ATT CAA ACA TTG CCT TCA GAT GCA AGT GTT TAT TTT CCT GTG AAT TAC GTT GAA AAC GAC CCT GGA
 300▶ G   I   Q   T   L   P   S   D   A   S   V   Y   F   P   V   N   Y   V   E   N   D   P   G
 967 TTA CAG TCC CAT CAC TTA CAC TTC CCA TTT TTC AGT GGA ATG GTC TTA CCA AGA GAA ATC CAT TCT TCA
 323▶ L   Q   S   H   H   L   H   F   P   F   F   S   G   M   V   L   P   R   E   I   H   S   S
1036 GTG CAT CAC ATG AAT AAG GCG TTT TTC TTG TTT GCA AGA CAG CAC GGT TAT GTT GTT TGG TTC TTT TAT
 346▶ V   H   H   M   N   K   A   F   F   L   F   A   R   Q   H   G   Y   V   V   W   F   F   Y
1105 GGT AAC TTA ATT GGA TGG TAT TAC AAT GGA AAT AAC CAC CCT TGG GAT TCG GAC ATC GAT GCC ATA ATG
 369▶ G   N   L   I   G   W   Y   Y   N   G   N   N   H   P   W   D   S   D   I   D   A   I   M
1174 CCC ATG GCG GAG ATG GCA AGA ATG GCT CAT CAC CAT AAC AAC ACA CTA ATA ATA GAG AAC CCC CAC GAT
 392▶ P   M   A   E   M   A   R   M   A   H   H   H   N   N   T   L   I   I   E   N   P   H   D
1243 GGA TAT GGA ACC TAT TTA CTG ACT ATT TCT CCT TGG TTC ACG AAG AAG ACA AGA GGT GGT AAC CAT ATT
 415▶ G   Y   G   T   Y   L   L   T   I   S   P   W   F   T   K   K   T   R   G   G   N   H   I
1312 GAT GGT CGT TTT GTG GAC GTT AAG AGG GGT ACC TAC ATC GAC CTC AGT GCA ATT TCA GCT ATG CAC GGA
 438▶ D   G   R   F   V   D   V   K   R   G   T   Y   I   D   L   S   A   I   S   A   M   H   G
1381 ATA TAT CCT GAC TGG GTT AGA GAT GGT GTG AAA GAA AAC CCT AAG AAT CTG GCT CTG GCC GAC AAG AAC
 461▶ I   Y   P   D   W   V   R   D   G   V   K   E   N   P   K   N   L   A   L   A   D   K   N
1450 GGT AAT TGG TAC CTT ACT AGA GAT ATT CTC CCA TTG AGG AGA ACA ATA TTC GAA GGT CTC GAT CCT TAC
 484▶ G   N   W   Y   L   T   R   D   I   L   P   L   R   R   T   I   F   E   G   S   R   S   Y
1519 ACC GTT AAA GAC ATT GAA GAT ACC CTG CTT AGA AAC TAT GGA GAT AAA GTA CTG ATA AAC ACA GAA CTG
 507▶ T   V   K   D   I   E   D   T   L   L   R   N   Y   G   D   K   V   L   I   N   T   E   L
1588 GCA GAC CAT GAA TGG CAT GAT GAC TGG AAA ATG TGG GTA CAA AAA AAG AAA TAC TGC ACT TAT GAG GAA
 530▶ A   D   H   E   W   H   D   D   W   K   M   W   V   Q   K   K   K   Y   C   T   Y   E   E
1657 TTT GAA GAT TAC CTG AGT GCT CAT GGA GGG GTT GAA TAC GAC GAA GAT GGA GTA TTG ACC TTG GAA GGA
 553▶ F   E   D   Y   L   S   A   H   G   G   V   E   Y   D   E   D   G   V   L   T   L   E   G
1726 GCT TGT GGA TTT GAA GAA GTC CGA CAA GAT TGG ATC ATT ACC CGT GAA AGT GTA AAT CTT CAT ATG AAG
 576▶ A   C   G   F   E   E   V   R   Q   D   W   I   I   T   R   E   S   V   N   L   H   M   K
1795 GAA TGG GAA GCT ATC CAG AGG AAC GAA TCA ACC ACA GAG TAT ACT GCT AAG GAT CTT CCT CGT TAC AGG
 599▶ E   W   E   A   I   Q   R   N   E   S   T   T   E   Y   T   A   K   D   L   P   R   Y   R
1864 CCA GAT TCC TTC AAA AAT CTA TTG GAT GGA GTT TCC AAT CAT GGA AAT GGA AAT GTT GGT AAG ATA GAG
 622▶ P   D   S   F   K   N   L   L   D   G   V   S   N   H   G   N   G   N   V   G   K   I   E
1933 CAT GTC AAA CTT GAA CAC AAC GAC TAG ATA GTT GTT TTT TCT ATA TAA AAC GAA ACG TTA TCA TCT TTA
 645▶ H   V   K   L   E   H   N   D
2002 ATA ATC ATT GAG GTT TAA AGG GCG AAT TCC AGC ACA CTG GCG GCC GTT ACT AGT GGA TC
```

Figure 3A

```
   1 ATG AGT GGC AAT CCT TTT CTG TTC TCT CCT TCA AAT TTT GAC TTT TCT GGT TTG GAT CAT TAT AGA TCC
   1▶  M   S   G   N   P   F   L   F   S   P   S   N   F   D   F   S   G   L   D   H   Y   R   S
  70 ACT GAT AAA GAT CAC TTA GCT CTA GAT GTT CTC GAT TAT GAC AAA AAT CAC TTC TTC TCC AGA AAC TCC
  24▶  T   D   K   D   H   L   A   L   D   V   L   D   Y   D   K   N   H   F   F   S   R   N   S
 139 CCC AGT TTG AAA TCT CGT ATT CAC TTT TAT CGA CAT AAA TTG ACC ACT AGA AAG CAA ATT GGA CTT TTC
  47▶  P   S   L   K   S   R   I   H   F   Y   R   H   K   L   T   T   R   K   Q   I   G   L   F
 208 AGC GGC AGA CTG AAG CTT TTT GTG CTT GCT CTC TTT GTG TTG ATC ACA TTT TCT GCA ATC CAC ATT CCA
  70▶  S   G   R   L   K   L   F   V   L   A   L   F   V   L   I   T   F   S   A   I   H   I   P
 277 ATC CCT TTC TCT TTG GAT ATT CTA GGT TCC CAT GTC AAA TAC CTG CCC TTA CGA GAG AAA GTC GAT CCG
  93▶  I   P   F   S   L   D   I   L   G   S   H   V   K   Y   L   P   L   R   E   K   V   D   P
 346 GAA GAG GCA CTC CAT CTG CAC GGA CTG GAT CTC TCG GTA GCA GAG CTA CCT TTT TTC AAT GAT GAC ATG
 116▶  E   E   A   L   H   L   H   G   L   D   L   S   V   A   E   L   P   F   F   N   D   D   M
 415 ATG TCT GAA TTT AAC TAC GAT CCT AGA CTA CCC ACC GCT TTG ATT TTG AAG TTA GTG TTA GAT CAT ATA
 139▶  M   S   E   F   N   Y   D   P   R   L   P   T   A   L   I   L   K   L   V   L   D   H   I
 484 AGT GTG CGT AAT GGA ACG TTT GAT GCT AAG TTT AAG GTC CCC TTT AAC TGG AAA CTT TGG GTG GAT TTG
 162▶  S   V   R   N   G   T   F   D   A   K   F   K   V   P   F   N   W   K   L   W   V   D   L
 553 CAT TCA AGG TTA GTT CCA TCT AAT AGT TGG TAT AAT CGA TTT CGA TTA CCC TCA GGT CGT TTC GAA ACA
 185▶  H   S   R   L   V   P   S   N   S   W   Y   N   R   F   R   L   P   S   G   R   F   E   T
 622 TGC GAT GAA TTT AAG AGG TTT TTC GGA ATC ACT AAG AAT CAC TTT GGA ACA GAC CTT GAT AAT TGC GTT
 208▶  C   D   E   F   K   R   F   F   G   I   T   K   N   H   F   G   T   D   L   D   N   C   V
 691 GAT ATC GAG TAT GAT ACT CCG GAA GGT TAT CCA AAG TTC AAA GTT TTG CAT GCG GAA GAT AAA GCT CTT
 231▶  D   I   E   Y   D   T   P   E   G   Y   P   K   F   K   V   L   H   A   E   D   K   A   L
 760 CCT TAT GAA GCA CGT ATC ATT TAT GGT GCT TCT TAC CTT TAC CAC GAA GCA CAG AAT CCT AAA AGG TTG
 254▶  P   Y   E   A   R   I   I   Y   G   A   S   Y   L   Y   H   E   A   Q   N   P   K   R   L
 829 ATA TTT TTA GGA TTG GGC AAG TCC AAT GAG TCT TTG ATC TTA CCA GTT GAG GCA AAT GAC AGT TCC AAC
 277▶  I   F   L   G   L   G   K   S   N   E   S   L   I   L   P   V   E   A   N   D   S   S   N
 898 TTA ATG CAA TTC AAC CAC GAA TAT GCA AGA AGC TTT AAC GAT CAA CCT TTC GTT TCT CTT GAG GAA CTT
 300▶  L   M   Q   F   N   H   E   Y   A   R   S   F   N   D   Q   P   F   V   S   L   E   E   L
 967 GTC AAG AAG GTT TCA CTG ACC TTG AAT TTG AAT AGT GAT AAG GTG CTA CCA ATC AAT GAA CTG GAC GTT
 323▶  V   K   K   V   S   L   T   L   N   L   N   S   D   K   V   L   P   I   N   E   L   D   V
1036 ATC AAA GAC ACC CCG CGC TTA ATG AAT CAC AAC AAC CAG GGA CTG AGC ATA GAC AAG AGC TCA TTT CAA
 346▶  I   K   D   T   P   R   L   M   N   H   N   N   Q   G   L   S   I   D   K   S   S   F   Q
1105 TGG GAT CTG GAA AGG GAA TTA CAG TTG TTA GAA CAT AGA ACC AGT CAA GTT AAT GAC GTG GAA GGC CTT
 369▶  W   D   L   E   R   E   L   Q   L   L   E   H   R   T   S   Q   V   N   D   V   E   G   L
1174 GAT GCG GGT ATT TAT TCA ACA ATT CAA TGT GAA ATG CGC TCT ATG TAC GAT TTT TCA AAA TAC TTC CAT
 392▶  D   A   G   I   Y   S   T   I   Q   C   E   M   R   S   M   Y   D   F   S   K   Y   F   H
1243 GAA TCA AAA GTC TCT GGT AAA TAT CTT CCT TCT GGA GAG CAC TAT GAC TGG CGA TTT TTT AAT GGT TTT
 415▶  E   S   K   V   S   G   K   Y   L   P   S   G   E   H   Y   D   W   R   F   F   N   G   F
1312 TAC CTT TCT CAG CAG GAG AAT CTA GCT GTC CTG CAC AGG TTA GGA AGA ACA TGG CTA CGC TTT TCT CGT
 438▶  Y   L   S   Q   Q   E   N   L   A   V   L   H   R   L   G   R   T   W   L   R   F   S   R
1381 GCT GCT GGT TTA CAT ACA TGG ATT GCT CAC GGG ACA CTG TTG GGT TGG TAT TGG AAT GGT CTG ATT CTG
 461▶  A   A   G   L   H   T   W   I   A   H   G   T   L   L   G   W   Y   W   N   G   L   I   L
1450 CCG TGG GAT CAG GAT CTT GAT GTT CAA ATG ACT GTA CAA TCA TTG TAT CTG TTG GGA AGG AAT TTC AAC
 484▶  P   W   D   Q   D   L   D   V   Q   M   T   V   Q   S   L   Y   L   L   G   R   N   F   N
1519 AGC TCT CTT GTA ACT GAT GTT AGT ATT GAA GAT GGC TAC AGC TCA GCA TTG GGA CAT TAC TAT ATT GAC
 507▶  S   S   L   V   T   D   V   S   I   E   D   G   Y   S   S   A   L   G   H   Y   Y   I   D
1588 GTT GGA TCC TCC TTC TTT GTT AGG GAT AAA CTA AAT GGT AAC AAT GCT ATA GAT GCA CGT TTC GTT GAT
 530▶  V   G   S   S   F   F   V   R   D   K   L   N   G   N   N   A   I   D   A   R   F   V   D
1657 ACT GAG ACC GGG TTG TAT GTT GAT ATA ACT GCA TTG GCT TTT ACA GAT CAC TTA AAA CTA AAA CTC ACT
 553▶  T   E   T   G   L   Y   V   D   I   T   A   L   A   F   T   D   H   L   K   L   K   L   T
1726 ACC AAA GAG AAA GTT GAG CTA CAG AAG GTT ATG GAT CCA AAT GTA AAG GAA AAA TTG CAG TGG ATC AAA
 576▶  T   K   E   K   V   E   L   Q   K   V   M   D   P   N   V   K   E   K   L   Q   W   I   K
1795 AAT AAA TAT TCA ACG GCC ACG CTA CCG GGT GTG ATA GAA ACA GAT AGG AAT AAA GTA TCT GAT GCG CTA
 599▶  N   K   Y   S   T   A   T   L   P   G   V   I   E   T   D   R   N   K   V   S   D   A   L
1864 GAG AAG CAA TTT CAT GAT TTC AAG TTC GAC AAT TTT GTC AAC AAA GAG TTG TTT CAC TGT CGA AAT AAC
 622▶  E   K   Q   F   H   D   F   K   F   D   N   F   V   N   K   E   L   F   H   C   R   N   N
1933 CAT TTC TAC AAA TAT GGA GAG GTT GGC CGA TTA CGG AGC ACT ATG TTT GAG GGC GTT CCT GCC CTT ATA
 645▶  H   F   Y   K   Y   G   E   V   G   R   L   R   S   T   M   F   E   G   V   P   A   L   I
2002 CCA TTT GAA TTT GAG TCC ATA CTG AAA CGA GAA TAT CCT AAA GGT CTA ACT TTG AAG CAT TTC TCC AAT
 668▶  P   F   E   F   E   S   I   L   K   R   E   Y   P   K   G   L   T   L   K   H   F   S   N
2071 CAT TTT TGG GAT CCA GTG AAC CGA TTG TGG GTA CCA GAA AAG AAG AAA AAA ATT AGA CAC ATA GAG TTT
 691▶  H   F   W   D   P   V   N   R   L   W   V   P   E   K   K   K   K   I   R   H   I   E   F
```

Figure 3β

```
2140 TCA CTT ACG AAG GAA GTT ACA GAA AGC CAC AAG AAA GAA CTT GCA CAG ATC CAT GGG AAC GAA ACG GGT
714▶ S   L   T   K   E   V   T   E   S   H   K   K   E   L   A   Q   I   H   G   N   E   T   G
2209 ATA ACC TCC GAC TTC GCA TAT TCT CCT TTC AGA ATA GAT CCC TGG CTG TCT CGA TAC AGG AAA AAA ATG
737▶ I   T   S   D   F   A   Y   S   P   F   R   I   D   P   W   L   S   R   Y   R   K   K   M
2278 ACT AGG AGC CAA
760▶ T   R   S   Q
```

Figure 5
A.
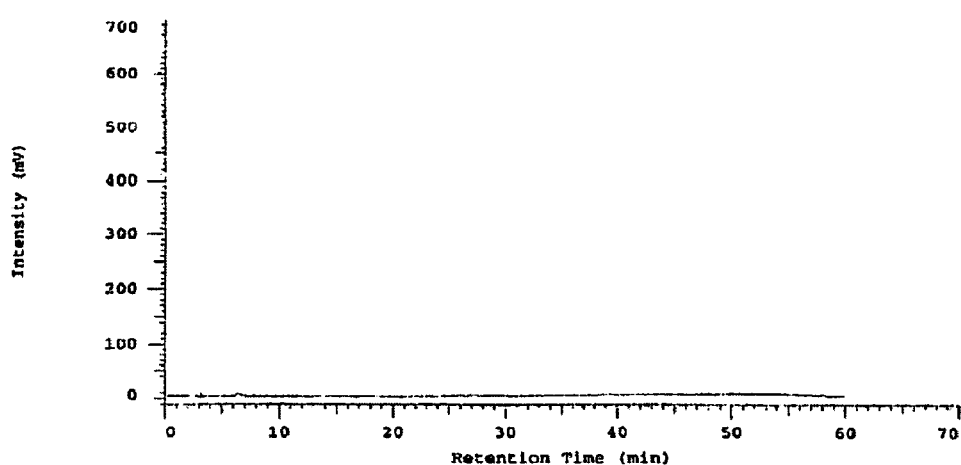
B.
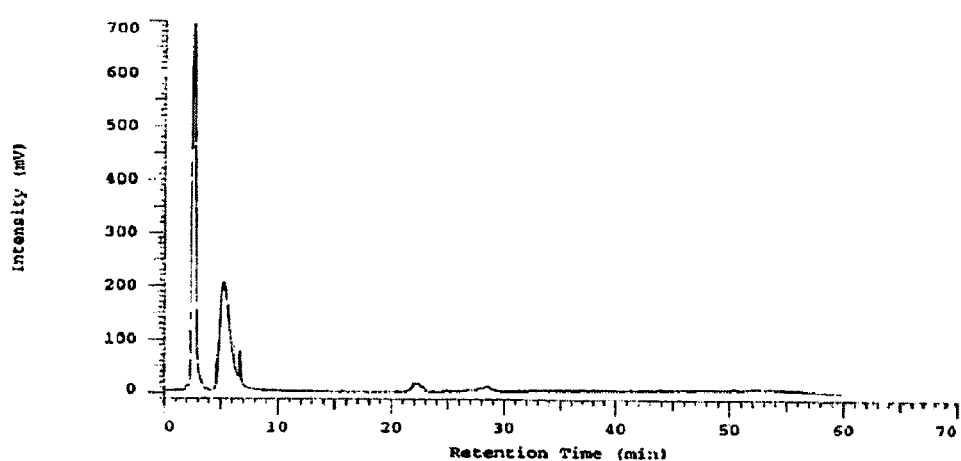
C.
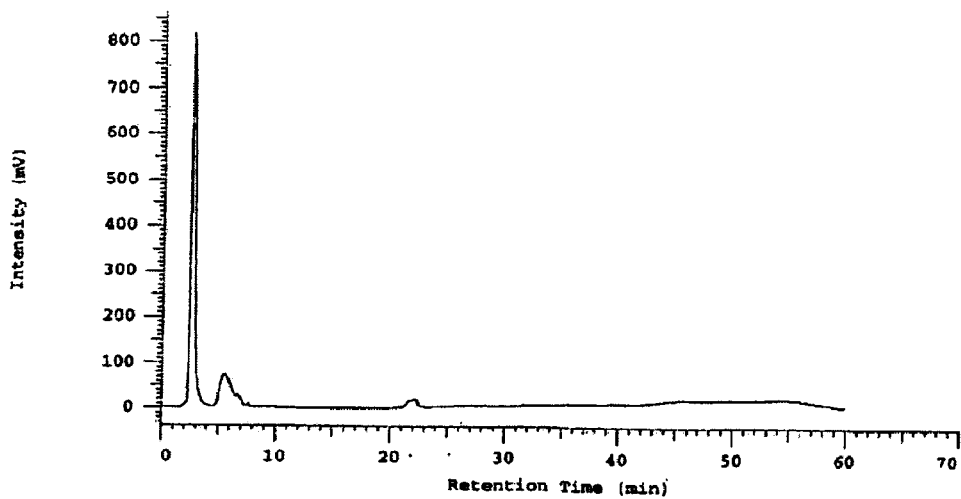

D.

Figure 6
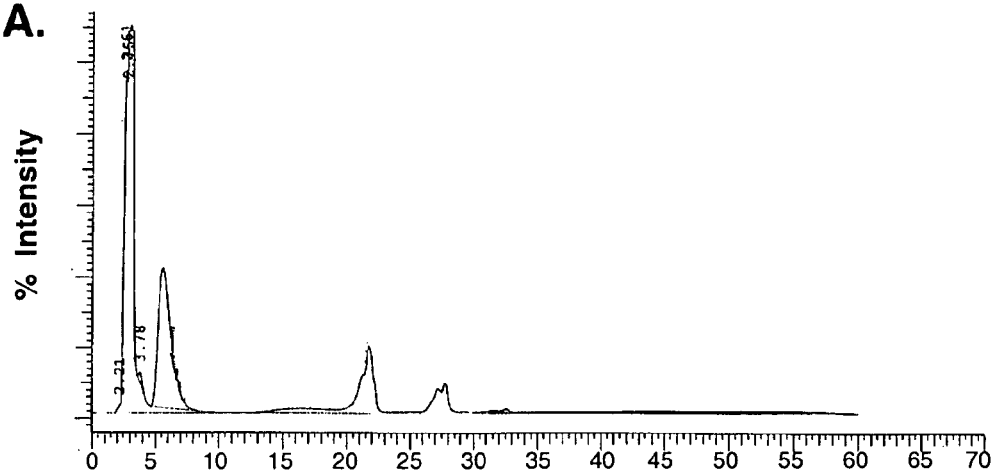
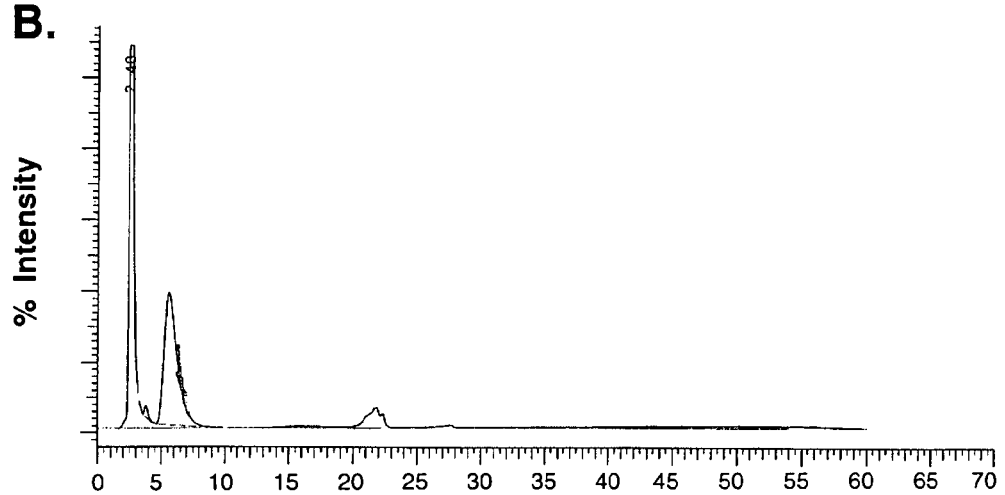
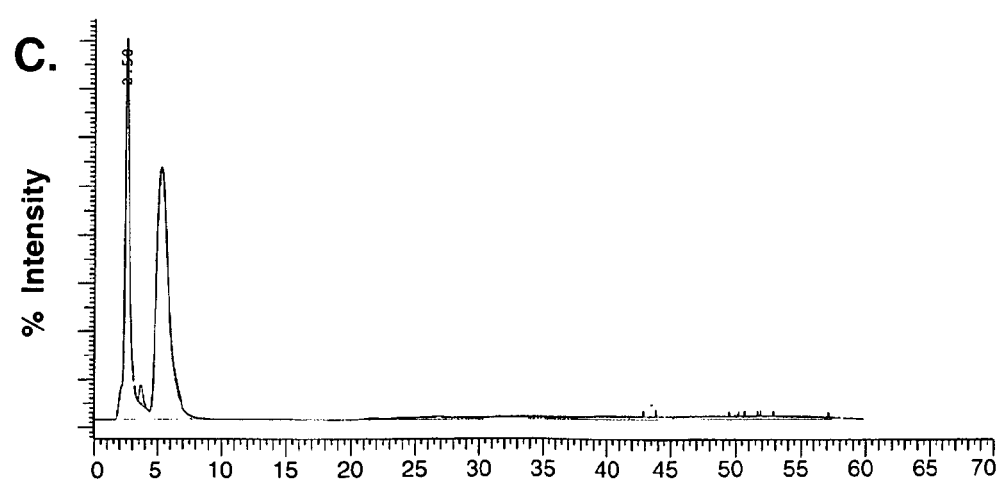
Retention Time (minutes)

Figure 7
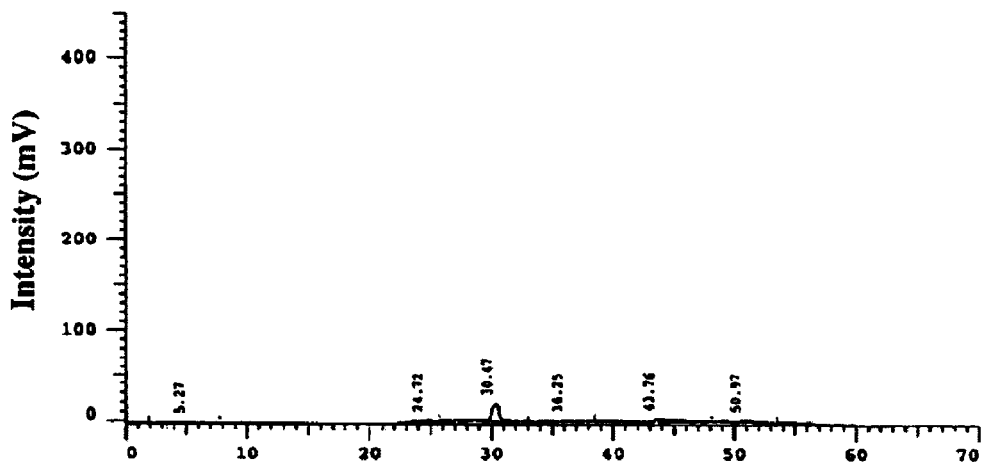
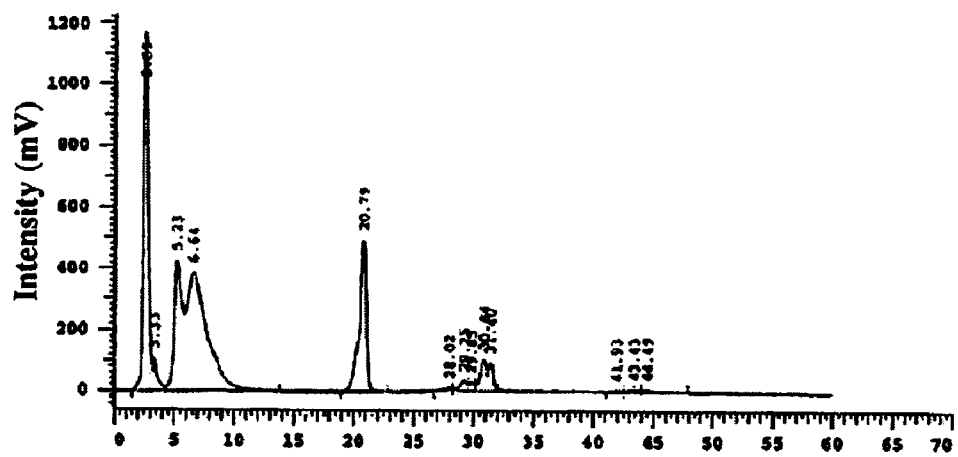
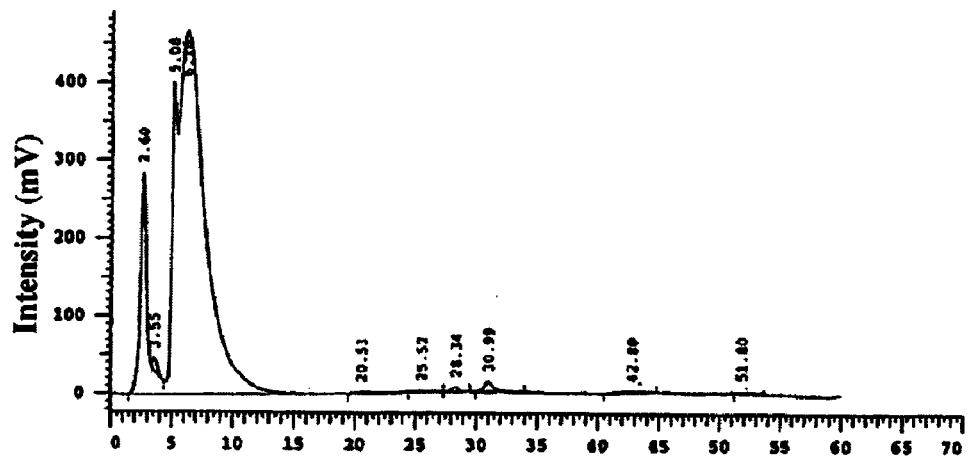
Retention time (minutes)

Figure 7
D.
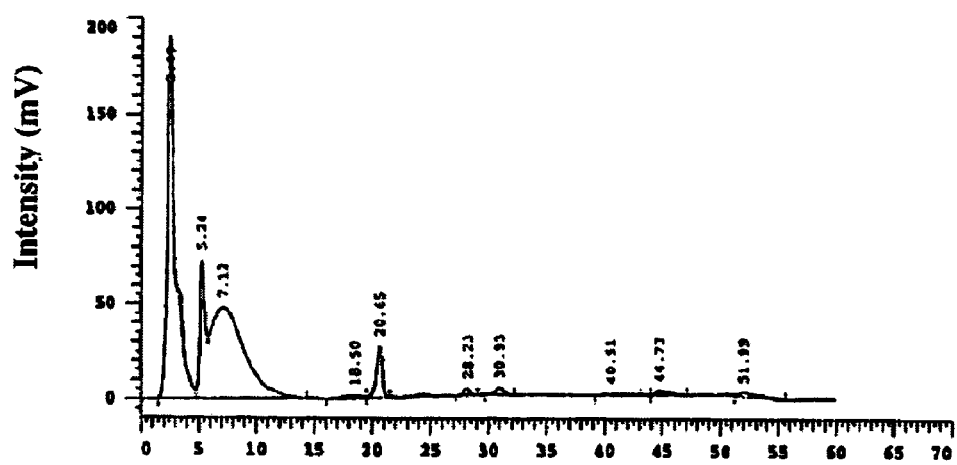
E.
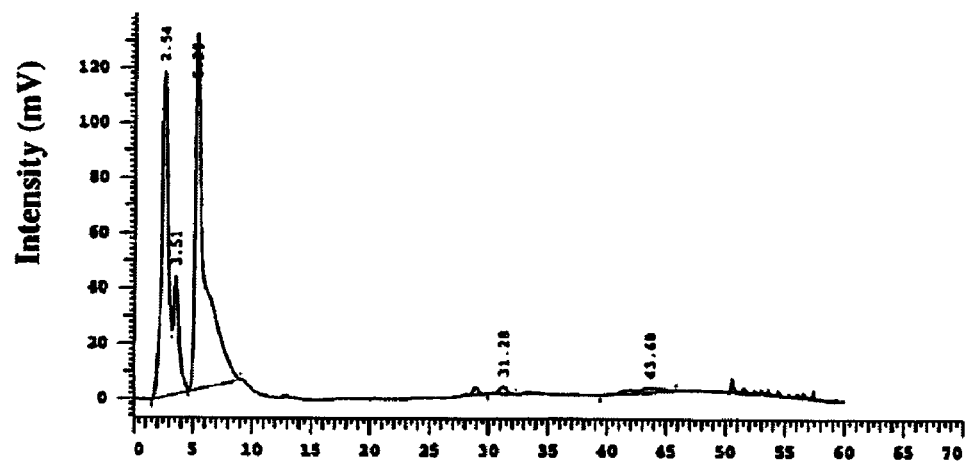
Retention time (minutes)

Figure 9A

```
1    - - - - - - M K V S K R L I - - - - - - - - - - P R R S R L L   PpMNN4A
1    - - - - - - - - - - - - - - - - - - - - - - - - - - - - - -   PpMNN4B
1    - - - - M S G N P F L F S P S N F D F S G L D H Y R S T D K   PpMNN4C
1    - - - - - - - - - - M T L R S A I K A R T S K G L I G A       PpPNO1
1    M L Q R I S S K L H R R F L S G L L R V K H Y P L R R I L L   ScMNN4
1    - - - - - - - - - - - - - - - - - - - - - - - - - - - - - -   NcMNN4A
1    - - - - - - - - - - - - - - - - - - - - - - - - - - - - - -   NcMNN4B
1    - - - - - - - - - - - - - - - - - - - - - - - - - - - - - -   AnMNN4A
1    - - - - - - - - - - - - - - - - - - - - - - - - - - - - - -   AnMNN4B
1    - - - - M S N T I P Q Y F I R I F N L I F S A R R K N F Q L   CaMNN4
1    - - - - - - - - - - - - - - - - - - - - - - - - - - - - - -   PaMNN4

16   I M M M L L V V Y Q L V V L V L G L E S V S E G K L A S L L   PpMNN4A
1    - - - - - - - - - - - - - - - - - - - - - - - - - - - - - -   PpMNN4B
27   D H L A L D V L D Y D K N H F F S R N S P S L K S R I H F Y   PpMNN4C
19   V I I A S I I F F T T V T F Y D E S K I V G I I R V S D T Y   PpPNO1
31   P L I L L Q I I I I T F I W S N S P Q R N G L G R D A D Y L   ScMNN4
1    - - - - - - - - - - - - - - - - - - - - - - - - - - - - - -   NcMNN4A
1    - - - - - - - - - - - - - - - - - - - - - - - - - - - - - -   NcMNN4B
1    - - - - - - - - - - - - - - - - - - - - - - - - - - - - - -   AnMNN4A
1    - - - - - - - - - - - - - - - - - - - - - - - - - - - - - -   AnMNN4B
27   A L I S G L L F F G S F A I L S T T S Y S K K F N Y F D D L   CaMNN4
1    - - - - - - - - - - - - - - - - - - - - - - - - - - - - - -   PaMNN4

46   D L G D W D L - - - - - - - - - - - - - A N S S L S I S D F   PpMNN4A
1    - - - - - - - - - - - - - - - - - - - - - - - - - - - - - -   PpMNN4B
57   R H K L T T R K Q I G - - - - - - - - - L F S G R L K L F V   PpMNN4C
49   T G H S A V S S T F N - - - - - - - - - A S S V V S D N K I   PpPNO1
61   L P N Y N E L - - - - - - - - - - - - - D S D D D S W Y S I   ScMNN4
1    - - - - - - - - - - - - - - - - - - - - - - - - - - - - - -   NcMNN4A
1    - - - - - - - - - - - - - - - - - - - - - - - - - - - - - -   NcMNN4B
1    - - - - - - - - - - - - - - - - - - - - - - - - - - - - - -   AnMNN4A
1    - - - - - - - - - - - - - - - - - - - - - - - - - - - - - -   AnMNN4B
57   I L K I Y D Y N Y L T N N Y N I D Y L A K N D P E A Y F N V   CaMNN4
1    - - - - - - - - - - - - - - - - - - - - - - - - - - - - - -   PaMNN4

63   I K L K L K G Q K T Y H K F D E H V F A A M A R I Q S N - -   PpMNN4A
1    - - - - - - - - - - - - - - - - - - - - - - - - - - - - - -   PpMNN4B
78   L A L F V L I T F S A I H I P I P F S L D I L G S H V K Y L   PpMNN4C
70   N G Y G L P L I D T E S N S R Y E D P D D I S I E N E L R Y   PpPNO1
78   L T S S F K N D R K I Q F A K T L Y E N L K F G T N P K - -   ScMNN4
1    - - - - - - - - - - - - - - - - - - - - - - - - - - - - - -   NcMNN4A
1    - - - - - - - - - - - - - - - - - - - - - - - - - - - - - -   NcMNN4B
1    - - - - - - - - - - - - - - - - - - - - - - - - - - - - - -   AnMNN4A
1    - - - - - - - - - - - - - - - - - - - - - - - - - - - - - -   AnMNN4B
87   K V Q Q I V D E K K Q H D L E S K F W S L D T K I N D D Q A   CaMNN4
1    - - - - - - - - - - - - - - - - - - - - - - - - - - - - - -   PaMNN4
```

Figure 9β

```
91  - - E N G K L A D Y E S T S S K T D V T I Q N V E L W K R L   PpMNN4A
1   - - - - - - - - - - - - - - - - - - - - - - - - - - - - -   PpMNN4B
108 P L R E K V D P E E A L H L H G L D L S V A E L P F F N D D   PpMNN4C
100 R I A Q S T K E E E N M W K L D T T L T E A S L K I P N I Q   PpPNO1
106 - - W V N E Y T L Q N D L L S V K M G P R K G S K L E S V D   ScMNN4
1   - - - - - - - - - - - - - - - - - - - - - - - - - - - - -   NcMNN4A
1   - - - - - - - - - - - - - - - - - - - - - - - - - - - - -   NcMNN4B
1   - - - - - - - - - - - - - - - - - - - - - - - - - - - - -   AnMNN4A
1   - - - - - - - - - - - - - - - - - - - - - - - - - - - - -   AnMNN4B
117 T L Q I P A Y F T Y N K P R D N K N L E D S E Q S S K P V E   CaMNN4
1   - - - - - - - - - - - - - - - - - - - - - - - - - - - - -   PaMNN4

119 S E E E Y T Y E P R I T L A V Y L S Y I H Q R T Y D R Y A T   PpMNN4A
1   - - - - - - - - - - - M F K E T S K N - - - - - - - - - -   PpMNN4B
138 M M S E F N Y D P R L P T A L I L K L V L D H I S V R N G T   PpMNN4C
130 S F E L Q P F K E R L D N S L Y N S K N I G N F Y F Y D P R   PpPNO1
134 E L K F Y D F D P R L T W S V V L N H L Q N N D A D Q P E -   ScMNN4
1   - - - - - - - - - - - M W S S L T P - - - - - - - - - - -   NcMNN4A
1   - - - - - - - - - - - - - - - - - - - - - - - - - - - - -   NcMNN4B
1   - - - - - - - - - - - - - - - - - - - - - - - - - - - - -   AnMNN4A
1   - - - - - - - - - - - - - - - - - - - - - - - - - - - - -   AnMNN4B
147 K P L I Q P F D P R F T L A M Y Y Y Y L D Q Q M T T A H H D   CaMNN4
1   - - - - - - - - - - - - - - - - - - - - - - - - - - - - -   PaMNN4

149 S Y A P - - - Y N L R V P F S W A D W I D L T A L N Q Y L D   PpMNN4A
9   - L F G - - - - - S I N T F N T V E Y V M Y M M L L L T A Y   PpMNN4B
168 F D A K - - - - - F K V P F N W K L W V D L H S R L V P S N   PpMNN4C
160 L T F S - - - - - V Y L K Y I K D K L A S G S T T N L T I P   PpPNO1
163 - - - - - - - - - K L P F S W Y D W T T F H E L N K L I S   ScMNN4
8   - - - - - - - - - A R R Q A T T T S W R D R L L T L L M A -   NcMNN4A
1   - - - - - - - - - - - - - - - - - - - - - - - - - - - - -   NcMNN4B
1   - - - - - - - - M H K K A T L A L A S A I C I T A -   AnMNN4A
1   - - - - - - - - - - - - - - - - - - - - - - - - - - - - -   AnMNN4B
177 S S S S S S G N S I T V P F N W Y D W V D M S V L N K Y L L   CaMNN4
1   - - - - - - - - - - - - - - - - - - - - - - - - - - - - -   PaMNN4

176 K T K - - - - - - - G C E A V F P R E S E A T M K L N N - -   PpMNN4A
33  F - - - - - - - - - - L N H L L H S L D N I N - - - - -   PpMNN4B
193 S W Y - - - - - N R F R L P S G R F E T C D E F K R F F G I   PpMNN4C
185 F N W - - - - - - A H F R D L S S L N P Y L D I K Q E D K V A   PpPNO1
183 I D K T V L P C N F L F Q S A F D K E S L E A I E T E L G E   ScMNN4
28  - - - - - - - - - - L T F V L S S L A S P - - - - -   NcMNN4A
1   - - - - - - - - - - - - - - - - - - - - - - - - - - - - -   NcMNN4B
18  - - - - - - - - - - - - - - - - - - - - - - - - - - - - -   AnMNN4A
1   - - - - - - - - - - - - - - - - - - - - - - - - - - - - -   AnMNN4B
207 A P N K D K P D C S I L D A H E D A R K I E T E K K K M E K   CaMNN4
1   - - - - - - - - - - - - - - - - - - - - - - - - - - - - -   PaMNN4
```

Figure 9C

```
197 - - - - I T - - - - V V D W L E G L C I T D K S L Q N S V N  PpMNN4A
46  - - - - - - - - - - - - - - - H L V E S D V N Y Q - - - - - -  PpMNN4B
218 T K N H F G - - - - - - - T D L D N C V D I E Y D T P E G Y  PpMNN4C
210 C D Y F Y E S S N K D K R K P T G N C I E F K D V R D E - -  PpPNO1
213 P L F L Y E - - - - R P K Y A Q K L W Y K A A R N Q D R I K  ScMNN4
39  - - - - - - - - - - - - L P I E G A V - - - - - - - - - - -  NcMNN4A
1   - - - - - - - - - - - - - - - - - - - - - - - - - - - - -  NcMNN4B
18  - - - - - - - - - - - - - A T G - - - - - - - - - - - - -  AnMNN4A
1   - - - - - - - - - - - - - - - - - - - - - - - - - - - - -  AnMNN4B
237 L A K Q W D E N K R K A E E E K K K A E E D K K K E E E E K  CaMNN4
1   - - - - - - - - - - - - - - - - - - - - - - M L V N S V -  PaMNN4

219 S T Y A E E I N S R D I L S P N F H - - - - - - - - - - - -  PpMNN4A
56  - L L Q R V T N K V K L F D E E A V L P F - - - - - - - - -  PpMNN4B
241 P K F K V L H A E D K A L P Y E A R I I Y G A - - - - - - -  PpMNN4C
238 H L I Q Y G I S S K D H L P G P F I L K S - - - - - - - - -  PpPNO1
239 D S K E L K K H C S K L F T P D G H G S P K G L R F N T Q F  ScMNN4
46  - - - - - - - - - - V K A N N N D A V S - - - - - - - - - -  NcMNN4A
1   - - - - - - - - - - - - - - - - - - - - - - - - - - - - -  NcMNN4B
21  - - - - - - - - - - - - - L P G P - - - - - - - - - - - -  AnMNN4A
1   - - - - - - - - - - - - - - - - - - - - - - - - - - - - -  AnMNN4B
267 K K A E E E E K Q R H E Q E K Q A L E E D K K K L E E E K K  CaMNN4
7   - - - - - - - - - - - - S P - - - - - - - - - - - - - - -  PaMNN4

237 V F G Y S D A K D N P Q Q K I F Q - - - - - - - - - - - - -  PpMNN4A
76  - - - - - - A K N L N R R T E R F D - - - - - - - - - - - -  PpMNN4B
264 S Y L Y H E A Q N P K R L I F L G - - - - - - - - - - - - -  PpMNN4C
259 - L G I P M Q H T A K R L E S N L - - - - - - - - - - - - -  PpPNO1
269 Q I K E L Y D K V R P E V Y Q L Q - - - - - - - - - - - - -  ScMNN4
56  - - - - - - - - - Q P Q A Q A Q - - - - - - - - - - - - -  NcMNN4A
1   - - - - - - - - - - - - - M L L - - - - - - - - - - - - -  NcMNN4B
25  - - - - - - - - - - - - - - - - - - - - - - - - - - - - -  AnMNN4A
1   - - - - - - - - - - - - - - - - - - - - - - - - - - - - -  AnMNN4B
297 K I E E E K N K L Q E Q Q Q Q Q Q Q E E K A N D G N Q E H S  CaMNN4
9   - - - - - - - - - - - - - - - - - - - - - - - - - - - - -  PaMNN4

254 - - - - - - - - - - - - - - - - - - S K S Y I N S K  PpMNN4A
88  - - - - - - - - - - - - - - - - - - P R L P V A A Y  PpMNN4B
281 - - - - - - - - - - - - - - - - - - L G K S N E S L  PpMNN4C
275 - - - - - - - - - - - - - - - - - - Y L L T G A P V  PpPNO1
286 - - - - - - - - - - - - - - - - - - A R N Y I L T T  ScMNN4
63  - - - - - - - - - - - - - - - - - - A K A E V R Q F  NcMNN4A
4   - - - - - - - - - - - - - - - - - - N W L L I V T T  NcMNN4B
25  - - - - - - - - - - - - - - - - - - - V L D S A P K  AnMNN4A
1   - - - - - - - - - - - - - - - - - - M R L S T Y P I  AnMNN4B
327 K F V K R D D E I K M S T S Q D K S D S D A D R A K I D M T  CaMNN4
9   - - - - - - - - - - - - - - - - - - S K S - - - - -  PaMNN4
```

Figure 9D

```
262  L P L P K S L - I F L T D G - - - - - - - - - - - - - -  PpMNN4A
96   L - - - R S L Q D Q Y S E L - - - - - - - - - - - - - -  PpMNN4B
289  I - - - L P V E A N D S S N - - - - - - - - - - - - - -  PpMNN4C
283  P - - - L S L S F M T K K G - - - - - - - - - - - - - -  PpPNO1
294  Q S H P L S I S I I E S D N - - - - - - - - - - - - - -  ScMNN4
71   S - - - A P A Q A Q E A E P - - - - - - - - - - - - - -  NcMNN4A
12   L - - - F P L S T - - - - - - - - - - - - - - - - - - -  NcMNN4B
32   - - - - A S V H G S V H G S - - - - - - - - - - - - - -  AnMNN4A
9    L - - - F A F C G - - - - - - - - - - - - - - - - - - -  AnMNN4B
357  T F F N E A F E K L S D E D K A S V A K D V E D A V K K I T  CaMNN4
12   - - - - - - - - - - - - - - - - - - - - - - - - - - - -  PaMNN4

275  - - - - - - - G S Y A L T V D R T Q N K R I L K S G L - - -  PpMNN4A
107  - - - - - - - - P Q G T D L N D I P P L E V S F H W D D W L  PpMNN4B
300  - - - - - - - - L M Q F N H E Y A R - - - - - - - - - - -  PpMNN4C
294  - - - - - - - - L Y Q V G V D Q T G K L D P N - - - - - -  PpPNO1
308  - - - - - - - S T Y Q V P L Q T E K S K N L V Q S G L - - -  ScMNN4
82   - - - - - - - - A T A T T S D D T T - - - - - - - - - - -  NcMNN4A
18   - - - - - - - - C A P I E H E D A - - - - - - - - - - - -  NcMNN4B
42   - - - - - - - - I L G T A A D I N - - - D P - - - - - - -  AnMNN4A
15   - - - - - - - - L A S V R G E G E - - - - - - - - - - - -  AnMNN4B
387  Q P S S W C V P N A K L S I D H S - D K Q I V H P G F N V F  CaMNN4
12   - - - - - - - - - - - E L D F D - - - - - - - - - - - - -  PaMNN4

295  - - - - - - - - - - - - - - - - - - - - - - - - - - L S  PpMNN4A
129  S - - - - - - - - - - - - - - - - - L G I A S T F W D A F  PpMNN4B
310  - - - - - - - - - - - - - - - - - - - - - - - - - - - -  PpMNN4C
309  - - - - - - - - - - - - - - - - - - I A R - - T E L W    PpPNO1
328  - - - - - - - - - - - - - - - - - - - - - - - - - - L Q  ScMNN4
92   - - - - - - - - - - - - - - - - - - - - - - - - - - - -  NcMNN4A
27   - - - - - - - - - - - - - - - - - - - - - - - - - - - -  NcMNN4B
53   - - - - - - - - - - - - - - - - - - - - - - - S Y L W    AnMNN4A
24   - - - - - - - - - - - - - - - - - - - - - - - - - - - -  AnMNN4B
416  K S P G R T T P Q K A I I A G K S F L Y S Y A P P P S S I L  CaMNN4
17   - - - - - - - - - - - - - - - - - - - - - - - - - - - S  PaMNN4

297  H F F S K - - - - - - - - - - - - - - K K K E H N L P    PpMNN4A
141  D N Y N K R Q G E N A I S Y E Q L Q A I L V N D L E D F S P  PpMNN4B
310  - S F N D Q P - - - - - - - - - - - - F V S L E E L V K  PpMNN4C
316  E F Y K N G K - - - - - - - E N L Q - - - F N A Q E E L S H  PpPNO1
330  E Y I N D N - - - - - - - - - - - - - - - I N S T N K R K  ScMNN4
92   - N T N - - - - - - - - - - - - - - - - - T D D D D P    NcMNN4A
27   - - - - - - - - - - - - - - - - - - - - I A I E G M A D  NcMNN4B
57   T M Y G - - - - - - - - - - - - - - - L N T S E E Y - -  AnMNN4A
24   - - - - - - - - - - - - - - - - - - - I T F E D V R D    AnMNN4B
446  F L T S E G S - - - - - - - - - - - - Y S V N V Q H S A P  CaMNN4
18   L F T A E - - - - - - - - - - - - - - - K N Y E F V I P  PaMNN4
```

Figure 9E

```
310 Q D Q K T F - - T F D P V Y E F N R L K S Q V K P - R P I S  PpMNN4A
171 Y - - - - - - - - - - - - - - - - - - - - - - - - - - - -  PpMNN4B
325 K V S L T L - - - - - - - - - - - - - - - N L N S D K V    PpMNN4C
336 L I E T V P - - - - - - - - - - - - - - - S S S N S S S    PpPNO1
344 K N K Q D V - - E F N H N R L F Q E F V N N D Q V N S L Y K ScMNN4
101 - - - - - - - - - - - - - - - - - - - - - - - - - - - - -  NcMNN4A
35  Q - - - - - - - - - - - - - - - - - - - - - - - - - - - -  NcMNN4B
68  - - - - - - - - - - - - - - - - - - - - - - - - - - - - -  AnMNN4A
32  K L - - - - - - - - - - - - - - - - - - - - - - - - - - -  AnMNN4B
463 L L R N G I P E S Y L A N N N F D V S L N V L Q Q L H K L K CaMNN4
31  P D R - - - - - - - - - - - F N - - - - - - - - - - - - -  PaMNN4

337 S E P S I D S A L K E N D Y K L K L E S S F I F N Y G R I  PpMNN4A
172 - - - - - T A H I L H S N V E V Y K Y R - - - T I P Q K I V PpMNN4B
338 L P I N E L D V I K D T P R L M N H N N Q G L S I D K S S F PpMNN4C
349 G E G Y F T T E L K E N N F E L P L S K N D F T F D D S E V PpPNO1
372 L E I E E T D K F T F D K D L V Y L S P S D F K F D A S K K ScMNN4
101 - - - - - - - - - - - - - - - - - - - - - - - - - - - - -  NcMNN4A
36  - - - - - - - - - - - - - - - - - - - - - - - - - - - - -  NcMNN4B
68  - - - - - - - - - - - - - - - - - - - - - - - - - - - - -  AnMNN4A
34  - - - - - - - - - - - - - - - - - - - - - - - - - - - - -  AnMNN4B
493 K N H K P D T A K V I N D Y L L H I P K E S F K Y D P D S I CaMNN4
36  - - - - - - - - - - - - - - - - - - - - - - Y S Y D Q I    PaMNN4

367 L S N Y E E R - - - - L E S L N D F E K S H Y E S L A Y S S PpMNN4A
194 Y M S N K G Y F E L - - - - L V T E K E K L S - - - - - - -  PpMNN4B
368 Q W D L E R E L Q L - L E H R T S Q V N D V E G L D A G I Y PpMNN4C
379 E S L I K G L S E Q - D L D L H T Q R Y K E S L Q Y S - - -  PpPNO1
402 I E E L E Q K K L Y P D K F S A H N E N Y L N S L K N S V   ScMNN4
101 - - - - - - - - - - - - L L P E R K - - - - - - - - - - -  NcMNN4A
36  - - - - - - - - - - K D M S G K A G D P P - - - - - - - -  NcMNN4B
68  - - - - - - - - - - - - - - - - - - - - - - - - - - - - -  AnMNN4A
34  - - - - - - - - - - P K T Y S G Q G G E P G - - - - - - -  AnMNN4B
523 I F D Y T K R L D K - G E K L T I K E L K Y L Q S L E Y S K CaMNN4
42  I E N Y E K R - - - - I D E L D E K Q L R H L Q T L K Y S R PaMNN4

393 - - - - - - - L L E A R K L P K Y F G E V I L K N P - - - - - PpMNN4A
213 - - - - - - - - - - N E G L W S I F H Q K Q G G L N E F S S L PpMNN4B
397 S T I Q C E M R S M Y D F S K Y F H E - - - - - - - - - - -  PpMNN4C
405 - - - - - F A T R E N D V K K Y F Y E A R M I I N - - - - -  PpPNO1
432 - - - - - K T S P A L Q R K F F Y E A G A V K Q - - - - - -  ScMNN4
107 - - - - - - - - - - - - - - Y F H E - - - - - - - - - - - -  NcMNN4A
47  - - - - - - - - - - - - Q K Y F H E - - - - - - - - - - - -  NcMNN4B
68  - - - - - - - - - - - - - K Y F Q E P - - - - - - - - - - -  AnMNN4A
46  - - - - - - - - - - - P K Y F K E - - - - - - - - - - - - -  AnMNN4B
552 D - - - - - K V A H G G P P K Y F A E S R L I G T - - - - -  CaMNN4
68  - - - - - - S I P S T K L K K S F R E V N I N W P A T Y - - PaMNN4
```

Figure 9F

```
412  - - - - - - - - - - - - - - - - - - Q - - - - - - - - -  PpMNN4A
234  N L I E E V D A L D E I Y D S K G L P A W D P P F P E E L D  PpMNN4B
416  - - - - - - - - - - - - - - - - - - - - - - - - - - - - -  PpMNN4C
425  - - - - - - - - - - - - - - - - - - T V N - - - - - - - -  PpPNO1
451  - - - - - - - - - - - - - - - - - - Y K - - - - - - - - -  ScMNN4
111  - - - - - - - - - - - - - - - - - - P G W - - - - - - - -  NcMNN4A
 53  - - - - - - - - - - - - - - - - - - - - - - - - - - - - -  NcMNN4B
 74  - - - - - - - - - - - - - - - - - - G N - - - - - - - - -  AnMNN4A
 52  - - - - - - - - - - - - - - - - - - - - - - - - - - - - -  AnMNN4B
572  - - - - - - - - - - - - - - - - - - - - - - - - - - - - -  CaMNN4
 90  N - - - - - - - - - - - - - - - - - G H K V - - - - - - -  PaMNN4

413  - - - - - - - - - - - - - D G G I H Y D Y R - - - - - - - F F  PpMNN4A
264  A S D E D F K F N A T E E L A K V E Q I K E P K L E D I F Y  PpMNN4B
416  - - - - - - - - - - - S K V S G K Y L P S G E - H Y D W R F F  PpMNN4C
428  - - - - - - - - - - - K E G G A H Y D W R - - - - - - - F F  PpPNO1
453  - - - - - - - - - - - - G M G F H R D K R - - - - - - - F F  ScMNN4
114  - - - - - - - - - - - T E E L S H Y D T R - - - - - - - F F  NcMNN4A
 53  - - - - - - - - - - - S T F A E K A L G - - - - - - - - -  NcMNN4B
 76  - - - - - - - - - - - D E I H A H Y D S R - - - - - - - F F  AnMNN4A
 52  - - - - - - - - - - - S S F A E S V L P - - - - - - - - -  AnMNN4B
572  - - - - - - - - - - - T V G D H Y D W R - - - - - - - F F  CaMNN4
 95  - - - - - - - - - - - T E N G G H Y D F R - - - - - - - F F  PaMNN4

424  S G - - - - - - - - - - - - - - - - - L I D K - - - T Q I N  PpMNN4A
294  Q E G L Q H G I Q T L P S D A S V Y F P V N Y V E N D P G L  PpMNN4B
435  N G - - - - - - - - - - - - - - - - - - F Y L - - S - - -  PpMNN4C
440  N G - - - - - - - - - - - - - - - - - A M N H E - - S S G F  PpPNO1
464  N - - - - - - - - - - - - - - - - - - - V D - - - T L I N  ScMNN4
126  T S - - - - - - - - - - - - - - - - - P V P Y - - - D P - -  NcMNN4A
 62  - - - - - - - - - - - - - - - - - - - - - - - - - - - - -  NcMNN4B
 88  K D - - - - - - - - - - - - - - - - - P V P K E - - H - -  AnMNN4A
 61  - - - - - - - - - - - - - - - - - - - - - - - - - - - - -  AnMNN4B
583  N G - - - - - - - - - - - - - - - - - - - - - - V Q F G  CaMNN4
107  N G - - - - - - - - - - - - - - - - - F V T E - - - S K L N  PaMNN4

434  H F E D E T E R K - - - - - - - - - - K I I M R R L L R T W  PpMNN4A
324  Q S H H L H F P F F S G M V L P R E I H S S V H H M N K A F  PpMNN4B
441  - - Q Q E N L - - - - - - - - - - - - A V L H R L G R A W  PpMNN4C
451  T E E R Q L - - - - - - - - - - R K R S V L H R L L R N W  PpPNO1
471  D K Q E Y Q A R - - - - - - - - - - - - L N S M I R T F  ScMNN4
134  - - H L V H L - - - - - - - - - - - - - - R H L I R S Y  NcMNN4A
 62  - - Y Q E Q K - - - - - - - - - - - - A A L K N L V R T F  NcMNN4B
 96  - - - - - - - - - - - - - - - - - - R S Q V L T H I I H S Y  AnMNN4A
 61  - - E E E T L - - - - - - - - - - - - P H L S A L I Q T Y  AnMNN4B
589  T V D Q S - L T - - - - - - - - - - - - - L H R L I R T W  CaMNN4
117  E Y D D V N E K R - - - - - - - - - - K I M L H R I I H T W  PaMNN4
```

Figure 9G

```
454 Q Y F T Y H N N I I N W I S H G S L L S W Y W D G L S F P W  PpMNN4A
354 F L F A R Q H G Y V V W F F Y G N L I G W Y Y N G N N H P W  PpMNN4B
456 L R F S R A A G L H T W I A H G T L L G W Y W N G L I L P W  PpMNN4C
471 L V F N Y Q Q G S P T W L A H G T L L S W Y W N S L M F P W  PpPNO1
487 Q K F T K A N G I I S W L S H G T L Y G Y L Y N G M A F P W  ScMNN4
146 L L M T S S R S L T T W L A H G T L L G W Y W N G A I M P W  NcMNN4A
 77 L E T M R D L G I E T W L M H G S L L G W W W N K Q I M P W  NcMNN4B
108 F E F F N S H N L E T W L A H G T L L G W W W N G R I M P W  AnMNN4A
 76 L S T M A D L G A E T W I M H G S L L A W W W N Q K I F P W  AnMNN4B
604 L S F T R K S G I T T W I A H G S L L S W Y W N G M A F P W  CaMNN4
137 L Q F T Y K E G I V S F L A H G T L L S W Y W N A L V F E W  PaMNN4

484 D N D I D V Q M P I M E L N N F C K Q F N - - - - - - - S  PpMNN4A
384 D S D I D A I M P M A E M A R M A H H H N N - - - - - - - T  PpMNN4B
486 D Q D L D V Q M T V Q S L Y L L G R N F N S S - - - - L V T  PpMNN4C
501 D Y D I D V Q M P I K S L N N L C A N F N Q - - - - - - - S  PpPNO1
517 D N D F D L Q M P I K H L Q L L S Q Y F N Q - - - - - - - S  ScMNN4
176 D Y D L D V Q V S N I T L G Q M A R D W N Q T T F D Y V Y T  NcMNN4A
107 D S D A D V Q V T E A S M Y F L A T Y Y N - - - - - - - M S  NcMNN4B
138 D W D I D T Q V S E A T L F R L A D E F N G - - - - - - - T  AnMNN4A
106 D N D L D V Q I N E P T I H F L A D Y Y N - - - - - - - M T  AnMNN4B
634 D N D I D V Q V P I M D L H K L S L Q F N Q - - - - - - - T  CaMNN4
167 D N D I D V Q M P I M D F D R F C M K Y N N - - - - - - - S  PaMNN4

507 L V E D V S - - Q G F G - - - - - - - - - R Y Y V D C T S F  PpMNN4A
407 L I I E N P H - - D G Y G - - - - - - - - T Y L L T I S P W  PpMNN4B
512 D V S I E D G Y S S A L G - - - - - - - - H Y Y I D V G S S  PpMNN4C
524 L I I E D L T - - E G Y S - - - - - - - - S F F L D C G S S  PpPNO1
540 L I L E D P R - - Q G N G - - - - - - - - R Y F L D V S D S  ScMNN4
206 L S E E E K - - E G L G K Q G E V T V K K Y L L D V N P Y  NcMNN4A
130 V F H Y K T P R L P A G R - - - - - - - - N Y M L E V N P N  NcMNN4B
161 V A Q Y N T T N P D T Q H - - - - - - - - S Y L L D V N P W  AnMNN4A
129 E H H F D L P D V E G G R - - - - - - - - T Y L L E I N P N  AnMNN4B
657 I V V E D P E - - D G F G - - - - - - - - R Y F L D I G S F  CaMNN4
190 L I V E D V Q - - H G Y G - - - - - - - - K Y Y V D C G P Y  PaMNN4

527 L A Q R T R G N G N N N I D A R F I D V S S G L F I D I T G  PpMNN4A
427 F T K K T R - - G G N H I D G R F V D V K R G T Y I D L S A  PpMNN4B
534 F F V R D K L N G N N A I D A R F V D T E T G L Y V D I T A  PpMNN4C
544 I T H R T K G K G L N F I D A R F I N V E T G L Y I D I T G  PpPNO1
560 L T V R I N G N G K N N I D A R F I D V D T G L Y I D I T G  ScMNN4
234 W A Q R T R L E G M N V I D A R W I D M E N G M Y V D I T G  NcMNN4A
152 F S N G D Q S D W L N V I D A R W I D T E S G L F I D I T T  NcMNN4B
183 A R Q R D R G K G L N I I D A R W I D M Q T G L Y I D I T G  AnMNN4A
151 Y V V R S K L D K A N V I D G R W I D T S S G L F I D I T A  AnMNN4B
677 I T L R E K G N G N N N I D A R F I D I D T G L Y I D I T A  CaMNN4
210 P T H R T K G N G R N N I D A R F I D V D S G M Y I D I T G  PaMNN4
```

Figure 9H

```
557  L A L T G S T M - - - - - P K R - - - - - - - - - - - - - -   PpMNN4A
455  I S A M H - - - - - - - - - - - - - - - - - - - - - - - - -   PpMNN4B
564  L A F T D H L K L T T K E K V E L Q K V M D P N V K E K       PpMNN4C
574  L S T S Q - - - - - - - - - - - - - - - - - - - - - - - - -   PpPNO1
590  L A S T S A P - - - - - - - S R D - - - - - - - - - - - - -   ScMNN4
264  L S - - - - - - - - - - - - - - - - - - - - - - - - - - - -   NcMNN4A
182  A R Y N L - - - - - - - - - - - - - - - - - - - - - - - - -   NcMNN4B
213  L S K L N - - - - - - - - - - - - - - - - - - - - - - - - -   AnMNN4A
181  V R A D D - - - - - - - - - - - - - - - - - - - - - - - - -   AnMNN4B
707  L A L S N S E T - - - - - - P K - - - - - - - - - - - - - -   CaMNN4
240  L A L T D T - - - - - - - - - - - - - - - - - - - - - - - -   PaMNN4

568  Y S N K L I K Q - - - - - - - - - - - - - - - - - - - - - -   PpMNN4A
460  - - - - - G I Y - - - - - - - - - - - - - - - - - - - - - -   PpMNN4B
594  L Q W I K N K Y - - - - - - - - - - - - - - - - - - - - - -   PpMNN4C
579  - - - - - S A R - - - - - - - - - - - - - - - - - - - - - -   PpPNO1
600  Y L N S Y I E E R L Q E E H L D I N N I P E S N G E T A T L   ScMNN4
266  - - - - - - - - - - - - - - - - - - - - - - - - - - - - - -   NcMNN4A
187  - - - - - - T H - - - - - - - - - - - - - - - - - - - - - -   NcMNN4B
218  - - - - - E E K - - - - - - - - - - - - - - - - - - - - - -   AnMNN4A
186  - - - - - - E R - - - - - - - - - - - - - - - - - - - - - -   AnMNN4B
717  - - S D L A E L - - - - - - - - - - - - - - - - - - - - - -   CaMNN4
246  - - - - - I K I - - - - - - - - - - - - - - - - - - - - - -   PaMNN4

576  P K K S T D - - - - - - - - - - - - - - - - - - - - - - - -   PpMNN4A
463  P D W V R D - - - - - - - - - - - - - - - - - - - - - - - -   PpMNN4B
602  S T A T L P - - - - - - - - - - - - - - - - - - - - - - - -   PpMNN4C
582  P P R F S N - - - - - - - - - - - - - - - - - - - - - - - -   PpPNO1
630  P D K V D D G L V N M A T L N I T E L R D Y I T S D E N K N   ScMNN4
266  E D R E E T - - - - - - - - - - - - - - - - - - - - - - - -   NcMNN4A
189  P A G - - E - - - - - - - - - - - - - - - - - - - - - - - -   NcMNN4B
221  P N E W G - - - - - - - - - - - - - - - - - - - - - - - - -   AnMNN4A
188  R A N G Q P - - - - - - - - - - - - - - - - - - - - - - - -   AnMNN4B
723  P K N - - - - - - - - - - - - - - - - - - - - - - - - - - -   CaMNN4
249  P - - - - - - - - - - - - - - - - - - - - - - - - - - - - -   PaMNN4

582  - - - - - - - - - - - - - - - - - S T G S T P E N G           PpMNN4A
469  - - - - - - - - - - - - - - - - - - - - - G V K E N P         PpMNN4B
608  - - - - - - - - - - - - - - - - - - - - - G V I E T D         PpMNN4C
588  - - - - - - - - - - - - - - - - - - - - - A S K K D P         PpPNO1
660  H K R V P T D T D L K D L L K K E L E E L P K S K T I E N K   ScMNN4
272  - - - - - - - - - - - - - - - - - - - - - G T R Q G -         NcMNN4A
193  - - - - - - - - - - - - - - - - - - - - - G M M S - -         NcMNN4B
226  - - - - - - - - - - - - - - - - - - - - - - - - - - -         AnMNN4A
194  - - - - - - - - - - - - - - - - - - - - - G A L M - -         AnMNN4B
726  - - - - - - - - - - - - - - - - - - - - F E I K D N N         CaMNN4
250  - - - - - - - - - - - - - - - - - - - - - - - - - - -         PaMNN4
```

Figure 9I

```
591  L T R N L R Q N L - - - - - - - - - - - - N A Q V Y N C R N  PpMNN4A
475  K N L - - - - - - - - - - - - - - - - - - - A L A D K N     PpMNN4B
614  R N K V S D A L E K Q F H D F K F D N F V N K E L F H C R N  PpMNN4C
594  - - - - - - - - - - - - - - - - - - - - - - - - I Y N C R N  PpPNO1
690  L N P K Q R Y F L N - - - - - - - - - - - E K L K L Y N C R N ScMNN4
277  - - - - - - - - - - - - - - - - - - - - - - - - V W S D K N  NcMNN4A
197  - - - - - - - - - - - - - - - - - - - - - - - - - - - C K D  NcMNN4B
226  - - - - - - - - - - - - - - - - - - - - - - - - - - - C K N  AnMNN4A
198  - - - - - - - - - - - - - - - - - - - - - - - - - - - C K D  AnMNN4B
733  Y K P A N - - - - - - - - - - - - - - - - E L L Q I Y N C R N CaMNN4
250  - - - - - - - - - - - - - - - - - - - - - - - - - - - - - -  PaMNN4

609  G H F Y Q Y S E L S P L K L S I V E G A L T L I P N D F V T  PpMNN4A
484  G N W Y L T R D I L P L R R T I F E G S R S Y T V K D I E D  PpMNN4B
644  N H F Y K G E V G R L R S T M F E G V P A L I P F E F E S    PpMNN4C
600  N H F Y S H N N I A P L K Y T L M E G V P S F I P Q Q Y E E  PpPNO1
710  N H F N S F E E L S P L I N T V F H G V P A L I P H R H T Y  ScMNN4
283  Y H G Y G T R Q I W P L R R T E F E G V E A W V P W D V E E  NcMNN4A
200  G H E F R V T I S T S V K S S - - - - - - - - - - - - - - -  NcMNN4B
229  N H N Y M L S D I Y P L R A S F F E G V A A K V P Y R Y E S  AnMNN4A
201  R H N F D E S E I Y P L R N S Y F E D V P A K I P Y A Y T K  AnMNN4B
748  N H F N S Y D E L S P L M K S S V E G E I G Y I P S R Y S T  CaMNN4
250  - - - - - - - - - - - - - - - - - - - - - - - - - - - - - -  PaMNN4

639  I L E T E Y Q R R G - L E K N T Y A K Y L Y V P E L R L W M  PpMNN4A
514  T L L R N Y G - D K V L I N T E L A D H E W H D D W K M W V  PpMNN4B
674  I L K R E Y - - P K G L T L K H F S N H F W D P V N R L W V  PpMNN4C
630  I L R E E Y - - T T G L T S K H Y N G N F F M T Q L N L W L  PpPNO1
740  C L H N E Y H V P D R Y A F D A Y K N T A Y L P E F R F W F  ScMNN4
313  I L K E E Y G - V K S L T E E S F A G H Q F D H G R K Q W V  NcMNN4A
215  - - - - - - - G G G - - - - - - - - - - - - - - - - - - - -  NcMNN4B
259  V L I D E Y G - E K A L S E T H Y N D Y T W V S K Q E E W V  AnMNN4A
231  L L Q D E Y - - G A K A L T K T N Y - - - - - - - - - - - -  AnMNN4B
778  I L T R E Y R S G - - L S S N S H G G Y I F I A K L R L W V  CaMNN4
250  - - - - - - - - - - - - - - - - - - - - - - - - - - - - - -  PaMNN4

668  S Y N D I Y D I L Q G T N S H G R P L S A K T M A T I F P R  PpMNN4A
543  Q K K K - - - - - - - - - - - - - - - - - - - Y C T Y E E F  PpMNN4B
702  P - - - - - - - - - - - - - - - - - - - - - - - - - - - - -  PpMNN4C
658  E R D P - - - - - - - - - - - - - - - - - - - - M L A L V P S PpPNO1
770  D Y D G - - - L K K C S N I N S W Y P N I P S I N S W N P N  ScMNN4
342  K T - - - - - - - - - - - - - - - - - - - - - - - - - - E L  NcMNN4A
217  - - - - - - - - - - - - - - - - - - - - - - - - - - - - - -  NcMNN4B
288  S - - - - - - - - - - - - - - - - - - - - - - - - - - - - -  AnMNN4A
247  - - - - - - - - - - - - - - - - - - - - - - - - - - - - - -  AnMNN4B
806  K E E D L Y Y F I K H R D Q W T K Y H S F N T K L S Q D P S  CaMNN4
250  - - - - - - - - - - - - - - - - - - - - - - - - - - - P R    PaMNN4
```

Figure 9U

```
698  L N S D I N L K K F L R N D H - - - - - - - - - - - - - - - - -  PpMNN4A
554  E D Y L S A H G G V E Y - - - - - - - - - - - - - - - - - - - -  PpMNN4B
703  - - - - - - - - - - - - - - - - - - - - - - - - - - - - - - - -  PpMNN4C
669  S K Y E I E G G G V D H N K I - - - - - - - - - - - - - - - - -  PpPNO1
797  L L K E I S S T K F E S K L F D S N K V S E Y S F K N L S M      ScMNN4
346  A                                                                NcMNN4A
217                                                                   NcMNN4B
289  - - - - - - - - - - - - - - - - - - - - - - - - - - - - - - - -  AnMNN4A
247  - - - - - - - - - - - - - - - - - - - - - - - - - - - - - - - -  AnMNN4B
836  N T L L Q D Y S Y L M S E Q - - - - - - - - - - - - - - - - - -  CaMNN4
252  L - - - - - - - - - - - - - - - - - - - - - - - - - - - - - - -  PaMNN4

713  - - - - - - - - - - - - - - - - T F K N I Y S T F N V T R        PpMNN4A
566  - - - - - - - - - - - - - - - - - - - - D E D G V L T            PpMNN4B
703  - - - - - - - - - - - - - - - - - - - - - - - - - - - -          PpMNN4C
684  - - - - - - - - - - - - - - - - - I K S I L E L S N I K K        PpPNO1
827  D D V R L I Y K N I P K A G F I E V F T N L Y N S F N V T A      ScMNN4
346                                                                   NcMNN4A
217                                                                   NcMNN4B
289  - - - - - - - - - - - - - - - - - - - - - - - - - - - - -        AnMNN4A
247  - - - - - - - - - - - - - - - - - - - - - - - - - - - - -        AnMNN4B
850  - - - - - - - - - - - - - - - - E Y E N L Q Y S T D L E H        CaMNN4
253  - - - - - - - - - - - - - - - - - - - - - - - - - - - - -        PaMNN4

726  V H E E E L K H L I V N - - - - - - - - - - - - - - - - - - - -  PpMNN4A
573  - - - - - - - - - - - - - - - - - - - - - - - - - - - - - - - -  PpMNN4B
703  - - - - - - - - - - - - - - - - - - - - - - - - - - - - - - - -  PpMNN4C
696  - - - - - - - - - - - - - - - - - - - - - - - - - - - - - - - -  PpPNO1
857  Y R Q K E L E I Q Y C Q N L T F I E K K K L L H Q L R I N V      ScMNN4
346                                                                   NcMNN4A
217                                                                   NcMNN4B
289  - - - - - - - - - - - - - - - - - - - - - - - - - - - - - - - -  AnMNN4A
247  - - - - - - - - - - - - - - - - - - - - - - - - - - - - - - - -  AnMNN4B
863  D N P F K K T K K P L E L K - - - - - - - - - - - - - - - - - -  CaMNN4
253  - - - - - - - - - - - - - - - - - - - - - - - - - - - - - - - -  PaMNN4

738  - - - - - - - - - - - - - - - - - - - - - - - - - - - - - - - -  PpMNN4A
573  - - - - - - - - - - - - - - - - - - - - - - - - - - - - - - - -  PpMNN4B
703  - - - - - - - - - - - - - - - - - - - - - - - - - - - - - - - -  PpMNN4C
696  - - - - - - - - - - - - - - - - - - - - - - - - - - - - - - - -  PpPNO1
887  A P K L S S P A K D P F L F G Y E K A M W K D L S K S M N Q      ScMNN4
346                                                                   NcMNN4A
217                                                                   NcMNN4B
289  - - - - - - - - - - - - - - - - - - - - - - - - - - - - - - - -  AnMNN4A
247  - - - - - - - - - - - - - - - - - - - - - - - - - - - - - - - -  AnMNN4B
877  - - - - - - - - - - - - - - - - - - - - - - - - - - - - - - - -  CaMNN4
253  - - - - - - - - - - - - - - - - - - - - - - - - - - - - - - - -  PaMNN4
```

Figure 9K

```
738   - - - - - - - - - - - - - - - - - - - - - - - - - - - - - -   PpMNN4A
573   - - - - - - - - - - - - - - - - - - - - - - - - - - - - - -   PpMNN4B
703   - - - - - - - - - - - - - - - - - - - - - - - - - - - - - -   PpMNN4C
696   - - - - - - - - - - - - - - - - - - - - - - - - - - - - - -   PpPNO1
917   T T L D Q V T K I V H E E Y V G K I I D L S E S L K Y R N F   ScMNN4
346                                                                 NcMNN4A
217                                                                 NcMNN4B
289   - - - - - - - - - - - - - - - - - - - - - - - - - - - - - -   AnMNN4A
247   - - - - - - - - - - - - - - - - - - - - - - - - - - - - - -   AnMNN4B
877   - - - - - - - - - - - - - - - - - - - - - - - - - - - - - -   CaMNN4
253   - - - - - - - - - - - - - - - - - - - - - - - - - - - - - -   PaMNN4

738   - - - - - - - - - - - - - - - - - - - Y D Q N K R K S A E   PpMNN4A
573   - - - - - - - - - - - - - - - - - - - - - - - - - - - - - -   PpMNN4B
703   - - - - - - - - - - - - - - - - - - - - - - - - - - - - - -   PpMNN4C
696   - - - - - - - - - - - - - - - - - - - - - - - - - - - - - -   PpPNO1
947   S L F N I T F D E T G T T L D D N T E D Y T P A N T V E V N   ScMNN4
346                                                                 NcMNN4A
217                                                                 NcMNN4B
289   - - - - - - - - - - - - - - - - - - - - - - - - - - - - - -   AnMNN4A
247   - - - - - - - - - - - - - - - - - - - - - - - - - - - - - -   AnMNN4B
877   - - - - - - - - - - - - - - - - - - - N S E L E K L K         CaMNN4
253   - - - - - - - - - - - - - - - - - - - - - - - - - - - - - -   PaMNN4

748   Y R Q F L E N L R F M N P I R K D L V T Y - - - - - - - - -   PpMNN4A
573   - - - - - - - - - - - - - - - - - - - - - - - - - - - - - -   PpMNN4B
703   - - - - - - - - - - - - - - - - - - - - - - - - - - - - - -   PpMNN4C
696   - - - - - - - - - - - - - - - - - - - - - - - - - - - - - -   PpPNO1
977   P V D F K S N L N F S S N S F L D L N S Y G L D L F A P T L   ScMNN4
346                                                                 NcMNN4A
217                                                                 NcMNN4B
289   - - - - - - - - - - - - - - - - - - - - - - - - - - - - - -   AnMNN4A
247   - - - - - - - - - - - - - - - - - - - - - - - - - - - - - -   AnMNN4B
885   H M N E S E L L Q F L N N D - - - - - - - - - - - - - - - -   CaMNN4
253   - - - - - - - - - - - - - - - - - - - - - - - - - - - - - -   PaMNN4

769   - - - - E S R L K A L D - - - - - - - - - G Y N E V E E L     PpMNN4A
573   - - - - - - - - - - - - - - - - - - - - - - - - - - L E G     PpMNN4B
703   - - - - - - - - - - - - - - - - - - - - - - - - - - - - - -   PpMNN4C
696   - - - - - - - - - - - - - - - - - - - - - - - - - - L E L     PpPNO1
1007  S D V N R K G I Q M F D K D P I I V Y E D Y A Y A K L L E E   ScMNN4
346                                                                 NcMNN4A
217                                                                 NcMNN4B
289   - - - - - - - - - - - - - - - - - - - - - - - - - - - - - -   AnMNN4A
247   - - - - - - - - - - - - - - - - - - - - - - - - - - - - - -   AnMNN4B
899   - - - - D I L I Q F F N - - - - - - - A K E F T S F H E S     CaMNN4
253   - - - - - - - - - - - - - - - - - - - - - - - - - - - - - -   PaMNN4
```

Figure 9L

```
785  EKKQENREKERKEKKEKEEKEKKEKEE--K      PpMNN4A
576  ACGFEEVRQDWIITRESVNLHMKEWEAIQR      PpMNN4B
703  EKKKKIRHIEFSLTKEVTESHKKELAQIHG      PpMNN4C
699  LDDNPDILEEVIRTYELTSIHHKEMQYLSS      PpPNO1
1037 RKRREKKKKEEEKKKKEEEKKKKEEEEK        ScMNN4
346                                      NcMNN4A
217                                      NcMNN4B
289  --------DEIIAAEEKK------------K     AnMNN4A
247  QGCVILQEVEFVVST                     AnMNN4B
917  EIMQLTFGKSTAKLMSSAIDFPPIKYEPYL      CaMNN4
253  ---------ERLDRQRKANNEQGKSED--A      PaMNN4

813  EKKEKEEKEKKEKEEKERKEKEKEEYEE-       PpMNN4A
606  NESTTEYTAKDLPRYRPDSFKNLLDGVSN-      PpMNN4B
733  NETGITSDFAYSP----------------       PpMNN4C
729  VKPDGDRSMQSND--ITSSYQEFLASLKKF      PpPNO1
1067 KKKEEEEKKKKEEEEKKKKEEEEKKKQEE-      ScMNN4
346                                      NcMNN4A
217                                      NcMNN4B
300  AK-EGD-----------------------       AnMNN4A
261                                      AnMNN4B
947  YKLNHDLDTFENKVDRYLALQDAYQQEHN-      CaMNN4
272  LPAEQTEGLSDPGASRNVKRAPVK------      PaMNN4

842  -DDNEGEQPTEQKSQQEAKE                PpMNN4A
635  -HGNGNVGKIEHVKLEHND                 PpMNN4B
746  -FRIDPWLSRYRKKMTRSQ                 PpMNN4C
757  QPLRKDLFQFERIDLSKHRKQ               PpPNO1
1096 -EEKKKKEEEEKKKQEEGEKMKNEDEENKK      ScMNN4
346                                      NcMNN4A
217                                      NcMNN4B
305  ----KDGRQYE                         AnMNN4A
261                                      AnMNN4B
976  -NSPSGGSDNGFMEIEEDLDFAF             CaMNN4
296  --SNKGPEVS                          PaMNN4

860                                      PpMNN4A
652                                      PpMNN4B
763                                      PpMNN4C
777                                      PpPNO1
1125 NEDEEKKKNEEEEKKKQEEKNKKNEDEEKK      ScMNN4
346                                      NcMNN4A
217                                      NcMNN4B
311                                      AnMNN4A
261                                      AnMNN4B
997                                      CaMNN4
303                                      PaMNN4
```

Figure 9M

| | | |
|---|---|---|
| 860 | | PpMNN4A |
| 652 | | PpMNN4B |
| 763 | | PpMNN4C |
| 777 | | PpPNO1 |
| 1155 | K Q E E E E K K K N E E E E K K K Q E E G H S N | ScMNN4 |
| 346 | | NcMNN4A |
| 217 | | NcMNN4B |
| 311 | | AnMNN4A |
| 261 | | AnMNN4B |
| 997 | | CaMNN4 |
| 303 | | PaMNN4 |

SEQUENCE LISTING

<160> NUMBER OF SEQ ID NOS: 29

<210> SEQ ID NO 1
<211> LENGTH: 2583
<212> TYPE: DNA
<213> ORGANISM: Pichia pastoris

<400> SEQUENCE: 1

| | | | | | |
|---|---|---|---|---|---|
| atgaaagtat | caaagcggtt | gataccgagg | agatctcgtc | tcctcattat | gatgatgcta | 60 |
| ctggttgttt | accagctggt | ggttttggtc | ctaggattgg | agagcgtctc | tgaaggaaaa | 120 |
| ttagcaagct | tgcttgactt | gggcgattgg | gatctagcta | actcctcgct | atctatatcc | 180 |
| gatttcataa | agctgaagct | caaaggccaa | aagacttatc | acaaatttga | tgaacatgtc | 240 |
| ttcgccgcaa | tggcaagaat | tcaaagtaat | gagaatggca | agttggcgga | ttacgagtct | 300 |
| acttcatcga | agactgacgt | aaccattcaa | aatgttgaac | tttggaagag | attgagcgaa | 360 |
| gaagaataca | cttacgaacc | gcggataact | ttggctgtgt | atctgagcta | cattcatcag | 420 |
| aggacttatg | acaggtacgc | gactagttac | gctccttata | acttgcgggt | gccttttttcg | 480 |
| tgggctgact | ggatagatct | gacggcccta | aatcaatact | tggataaaac | gaaaggctgc | 540 |
| gaggcagttt | tccctagaga | aagtgaggca | actatgaagc | ttaacaatat | cactgttgtg | 600 |
| gactggcttg | agggcctttg | cataactgat | aaatcacttc | aaaattccgt | aaactccaca | 660 |
| tatgcggaag | agattaatag | tcgggacatc | ttgtctccta | acttccatgt | gtttggttat | 720 |
| tctgatgcta | agataatcc | tcagcaaaaa | atctttcaat | ctaaatctta | tatcaactca | 780 |
| aagctgccgc | tcccaaaaag | tttgatattt | ttaacagatg | gaggtagtta | cgctttgaca | 840 |
| gtcgaccgaa | ctcaaaataa | aagaattcta | aaatctggcc | tgctttcaca | cttttttctca | 900 |
| aagaaaaaga | aggaacacaa | tctgcctcaa | gaccaaaaaa | cttttcacgtt | tgaccccgta | 960 |
| tacgaattca | atagactgaa | atctcaggtc | aagccccgtc | caatatcttc | agaacctagt | 1020 |
| attgattctg | ctttgaagga | aaatgactac | aagcttaaac | tgaaagagtc | gtcgtttatt | 1080 |
| tttaattacg | gaaggattct | ttcgaactat | gaagagcggc | ttgagagtct | aaatgacttc | 1140 |
| gagaaatcgc | actacgagtc | cttagcttat | tcctccttgt | tagaggcaag | aaagttgccc | 1200 |
| aagtattttg | gcgaagttat | attgaagaac | ccacaagatg | gtggaattca | ttatgattac | 1260 |
| agattcttca | gcggactcat | tgataaaact | cagataaatc | attttgagga | tgagactgaa | 1320 |
| agaaagaaaa | taatcatgcg | tagacttctt | cgaacttggc | agtacttcac | gtatcacaat | 1380 |
| aacattatca | attggatctc | gcacggttct | ttactgtcat | ggtattggga | tggactttct | 1440 |
| tttccatggg | acaatgacat | tgacgtacaa | atgcccataa | tggagctgaa | taacttctgc | 1500 |
| aaacagttca | acaattctct | ggtcgtggag | gatgtttctc | aagggtttgg | cagatactac | 1560 |
| gttgattgca | cgagcttcct | ggcccagaga | acgcgaggta | atggtaacaa | caacattgat | 1620 |
| gcccgttttta | ttgatgtgtc | gtctggtctc | ttcattgaca | ttacggggttt | ggctttgact | 1680 |
| ggatcaacaa | tgcccaaaag | atactccaat | aagctgataa | acaaccgaa | aaaatctacc | 1740 |
| gactcaacag | gatcgactcc | tgagaacgga | ctcactagaa | acttgaggca | aaatttgaat | 1800 |
| gcacaagttt | acaactgtag | aaacggtcat | ttttaccaat | actcggagct | atctcctttg | 1860 |
| aagttgtcga | tagtagaagg | tgcactcacc | ctaataccca | acgattttgt | tactatattg | 1920 |
| gaaactgagt | accaaggag | aggtcttgaa | aagaacacat | atgcgaagta | tctctacgtt | 1980 |
| ccagagcttc | gactttggat | gtcatacaat | gacatctatg | atatcttgca | aggtactaat | 2040 |

-continued

```
agtcatggcc gtcctttatc tgcaaagaca atggcgacta tctttcctcg gttaaactct      2100
gacattaatc taaaaaagtt tttgcgcaat gatcatactt ttaagaacat ttattctact      2160
ttcaacgtga cacgagtgca cgaggaggaa ctgaagcatt tgatagtaaa ctatgaccaa      2220
aataaacgga agtcggctga gtacaggcag ttcttggaaa acttgcggtt tatgaatcca      2280
atcagaaaag atctggtgac ttacgagagt aggttgaagg ctcttgatgg atacaatgag      2340
gtcgaagaat tagaaaagaa gcaagagaat agggaaaaag aaagaaagga gaagaaggaa      2400
aaggaggaaa aagagaagaa ggaaaaggag gaaaaagaga agaaggaaaa ggaagaaaag      2460 gaaagaagg aaaaggaaga aaaggagagg aaagagaagg aagaaaagga agaatatgaa       2520
gaagacgata atgagggcga acaaccaaca gaacaaaaga gccagcagga ggctaaagaa      2580
tag                                                                    2583
```

<210> SEQ ID NO 2
<211> LENGTH: 860
<212> TYPE: PRT
<213> ORGANISM: Pichia pastoris

<400> SEQUENCE: 2

```
Met Lys Val Ser Lys Arg Leu Ile Pro Arg Arg Ser Arg Leu Leu Ile
 1               5                  10                  15

Met Met Met Leu Leu Val Val Tyr Gln Leu Val Leu Val Leu Val Gly
             20                  25                  30

Leu Glu Ser Val Ser Glu Gly Lys Leu Ala Ser Leu Leu Asp Leu Gly
         35                  40                  45

Asp Trp Asp Leu Ala Asn Ser Ser Leu Ser Ile Ser Asp Phe Ile Lys
     50                  55                  60

Leu Lys Leu Lys Gly Gln Lys Thr Tyr His Lys Phe Asp Glu His Val
 65                  70                  75                  80

Phe Ala Ala Met Ala Arg Ile Gln Ser Asn Glu Asn Gly Lys Leu Ala
                 85                  90                  95

Asp Tyr Glu Ser Thr Ser Ser Lys Thr Asp Val Thr Ile Gln Asn Val
            100                 105                 110

Glu Leu Trp Lys Arg Leu Ser Glu Glu Glu Tyr Thr Tyr Glu Pro Arg
        115                 120                 125

Ile Thr Leu Ala Val Tyr Leu Ser Tyr Ile His Gln Arg Thr Tyr Asp
    130                 135                 140

Arg Tyr Ala Thr Ser Tyr Ala Pro Tyr Asn Leu Arg Val Pro Phe Ser
145                 150                 155                 160

Trp Ala Asp Trp Ile Asp Leu Thr Ala Leu Asn Gln Tyr Leu Asp Lys
                165                 170                 175

Thr Lys Gly Cys Glu Ala Val Phe Pro Arg Glu Ser Glu Ala Thr Met
            180                 185                 190

Lys Leu Asn Asn Ile Thr Val Asp Trp Leu Glu Gly Leu Cys Ile
        195                 200                 205

Thr Asp Lys Ser Leu Gln Asn Ser Val Asn Ser Thr Tyr Ala Glu Glu
    210                 215                 220

Ile Asn Ser Arg Asp Ile Leu Ser Pro Asn Phe His Val Phe Gly Tyr
225                 230                 235                 240

Ser Asp Ala Lys Asp Asn Pro Gln Gln Lys Ile Phe Gln Ser Lys Ser
                245                 250                 255

Tyr Ile Asn Ser Lys Leu Pro Leu Pro Lys Ser Leu Ile Phe Leu Thr
            260                 265                 270
```

```
Asp Gly Gly Ser Tyr Ala Leu Thr Val Asp Arg Thr Gln Asn Lys Arg
        275                 280                 285

Ile Leu Lys Ser Gly Leu Leu Ser His Phe Phe Ser Lys Lys Lys
290                 295                 300

Glu His Asn Leu Pro Gln Asp Gln Lys Thr Phe Thr Phe Asp Pro Val
305                 310                 315                 320

Tyr Glu Phe Asn Arg Leu Lys Ser Gln Val Lys Pro Arg Pro Ile Ser
                325                 330                 335

Ser Glu Pro Ser Ile Asp Ser Ala Leu Lys Glu Asn Asp Tyr Lys Leu
            340                 345                 350

Lys Leu Lys Glu Ser Ser Phe Ile Phe Asn Tyr Gly Arg Ile Leu Ser
        355                 360                 365

Asn Tyr Glu Glu Arg Leu Glu Ser Leu Asn Asp Phe Glu Lys Ser His
    370                 375                 380

Tyr Glu Ser Leu Ala Tyr Ser Ser Leu Leu Glu Ala Arg Lys Leu Pro
385                 390                 395                 400

Lys Tyr Phe Gly Glu Val Ile Leu Lys Asn Pro Gln Asp Gly Gly Ile
                405                 410                 415

His Tyr Asp Tyr Arg Phe Phe Ser Gly Leu Ile Asp Lys Thr Gln Ile
            420                 425                 430

Asn His Phe Glu Asp Glu Thr Glu Arg Lys Lys Ile Ile Met Arg Arg
        435                 440                 445

Leu Leu Arg Thr Trp Gln Tyr Phe Thr Tyr His Asn Asn Ile Ile Asn
    450                 455                 460

Trp Ile Ser His Gly Ser Leu Leu Ser Trp Tyr Trp Asp Gly Leu Ser
465                 470                 475                 480

Phe Pro Trp Asp Asn Asp Ile Asp Val Gln Met Pro Ile Met Glu Leu
                485                 490                 495

Asn Asn Phe Cys Lys Gln Phe Asn Asn Ser Leu Val Val Glu Asp Val
            500                 505                 510

Ser Gln Gly Phe Gly Arg Tyr Tyr Val Asp Cys Thr Ser Phe Leu Ala
        515                 520                 525

Gln Arg Thr Arg Gly Asn Gly Asn Asn Asn Ile Asp Ala Arg Phe Ile
    530                 535                 540

Asp Val Ser Ser Gly Leu Phe Ile Asp Ile Thr Gly Leu Ala Leu Thr
545                 550                 555                 560

Gly Ser Thr Met Pro Lys Arg Tyr Ser Asn Lys Leu Ile Lys Gln Pro
                565                 570                 575

Lys Lys Ser Thr Asp Ser Thr Gly Ser Thr Pro Glu Asn Gly Leu Thr
            580                 585                 590

Arg Asn Leu Arg Gln Asn Leu Asn Ala Gln Val Tyr Asn Cys Arg Asn
        595                 600                 605

Gly His Phe Tyr Gln Tyr Ser Glu Leu Ser Pro Lys Leu Ser Ile
    610                 615                 620

Val Glu Gly Ala Leu Thr Leu Ile Pro Asn Asp Phe Val Thr Ile Leu
625                 630                 635                 640

Glu Thr Glu Tyr Gln Arg Arg Gly Leu Glu Lys Asn Thr Tyr Ala Lys
                645                 650                 655

Tyr Leu Tyr Val Pro Glu Leu Arg Leu Trp Met Ser Tyr Asn Asp Ile
            660                 665                 670

Tyr Asp Ile Leu Gln Gly Thr Asn Ser His Gly Arg Pro Leu Ser Ala
        675                 680                 685
```

```
Lys Thr Met Ala Thr Ile Phe Pro Arg Leu Asn Ser Asp Ile Asn Leu
        690                 695                 700

Lys Lys Phe Leu Arg Asn Asp His Thr Phe Lys Asn Ile Tyr Ser Thr
705                 710                 715                 720

Phe Asn Val Thr Arg Val His Glu Glu Glu Leu Lys His Leu Ile Val
                725                 730                 735

Asn Tyr Asp Gln Asn Lys Arg Lys Ser Ala Glu Tyr Arg Gln Phe Leu
            740                 745                 750

Glu Asn Leu Arg Phe Met Asn Pro Ile Arg Lys Asp Leu Val Thr Tyr
        755                 760                 765

Glu Ser Arg Leu Lys Ala Leu Asp Gly Tyr Asn Glu Val Glu Glu Leu
770                 775                 780

Glu Lys Lys Gln Glu Asn Arg Glu Lys Glu Arg Lys Glu Lys Lys Glu
785                 790                 795                 800

Lys Glu Glu Lys Glu Lys Lys Glu Lys Glu Lys Lys Glu
                805                 810                 815

Lys Glu Glu Lys Glu Lys Lys Glu Lys Glu Lys Glu Arg Lys Glu
            820                 825                 830

Lys Glu Glu Lys Glu Glu Tyr Glu Glu Asp Asp Asn Glu Gly Glu Gln
            835                 840                 845

Pro Thr Glu Gln Lys Ser Gln Gln Glu Ala Lys Glu
        850                 855                 860

<210> SEQ ID NO 3
<211> LENGTH: 1959
<212> TYPE: DNA
<213> ORGANISM: Pichia pastoris

<400> SEQUENCE: 3
```

| | |
|---|---|
| atgttcaaag aaacgtcaaa gaacttgttt ggttcgataa ataccttcaa tacggtggag | 60 |
| tatgtcatgt atatgatgct actactgact gcgtattttt tgaaccacct gttgcatagt | 120 |
| ttggataaca tcaatcattt ggttgagtct gatgttaatt atcaactact caaagggta | 180 |
| acaaataaag tcaagctttt tgatgaggaa gcagtcttgc cctttgctaa gaatctcaat | 240 |
| agaagaactg aacgctttga tccaaggttg cctgtagctg catacttcg aagccttcaa | 300 |
| gatcagtatt cggagcttcc acaaggtacc gacctgaatg atattccgcc cctgaggtt | 360 |
| tctttccact gggatgactg gttaagtttg gaattgcat caaccttttg ggacgccttc | 420 |
| gacaattaca caagagaca aggagaaaat gcaatttctt acgagcagct ccaagcaata | 480 |
| cttgttaatg atttggaaga ttttttctccc tacaccgcac atattcttca cagtaacgtg | 540 |
| gaagtctaca aatacagaac gattcctcaa aagatcgtct atatgtcaaa caagggctat | 600 |
| tttgaactct tggtaaccga aaaggaaaaa ctatccaatg agggtctctg gagcattttc | 660 |
| catcagaaac aaggtggact taacgaattc agtagtctca atctcataga ggaggttgat | 720 |
| gcgttggatg aaatctatga ttccaaaggg ttgcctgctt gggatcctcc cttccctgag | 780 |
| gaacttgatg cttcagatga agatttcaag ttcaatgcca cagaagaact ggcaaaggta | 840 |
| gagcaaatca agaaccaaa gctggaagac atattctatc aggaaggact gcaacacggg | 900 |
| attcaaacat tgccttcaga tgcaagtgtt tattttcctg tgaattacgt tgaaaacgac | 960 |
| cctggattac agtcccatca cttacacttc ccatttttca gtggaatggt cttaccaaga | 1020 |
| gaaatccatt cttcagtgca tcacatgaat aaggcgtttt tcttgtttgc aagacagcac | 1080 |
| ggttatgttg tttggttctt ttatggtaac ttaattggat ggtattacaa tgaaaataac | 1140 |

```
caccettggg attcggacat cgatgccata atgcccatgg cggagatggc aagaatggct   1200
catcaccata acaacacact aataatagag accccacg atggatatgg aacctattta    1260
ctgactattt ctccttggtt cacgaagaag acaagaggtg gtaaccatat tgatggtcgt   1320
tttgtggacg ttaagagggg tacctacatc gacctcagtg caatttcagc tatgcacgga   1380
atatatcctg actgggttag agatggtgtg aaagaaaacc ctaagaatct ggctctggcc   1440
gacaagaacg gtaattggta ccttactaga gatattctcc cattgaggag aacaatattc   1500
gaaggttctc gatcctacac cgttaaagac attgaagata ccctgcttag aaactatgga   1560
gataaagtac tgataaacac agaactggca gaccatgaat ggcatgatga ctggaaaatg   1620
tgggtacaaa aaagaaata ctgcacttat gaggaatttg aagattacct gagtgctcat    1680 ggagggttg aatacgacga agatggagta ttgaccttgg aaggagcttg tggatttgaa    1740
gaagtccgac aagattggat cattacccgt gaaagtgtaa atcttcatat gaaggaatgg   1800
gaagctatcc agaggaacga atcaaccaca gagtatactg ctaaggatct tcctcgttac   1860
aggccagatt ccttcaaaaa tctattggat ggagtttcca atcatggaaa tggaaatgtt   1920
ggtaagatag agcatgtcaa acttgaacac aacgactag                          1959
```

<210> SEQ ID NO 4
<211> LENGTH: 652
<212> TYPE: PRT
<213> ORGANISM: Pichia pastoris

<400> SEQUENCE: 4

```
Met Phe Lys Glu Thr Ser Lys Asn Leu Phe Gly Ser Ile Asn Thr Phe
 1               5                  10                  15

Asn Thr Val Glu Tyr Val Met Tyr Met Met Leu Leu Leu Thr Ala Tyr
            20                  25                  30

Phe Leu Asn His Leu Leu His Ser Leu Asp Asn Ile Asn His Leu Val
        35                  40                  45

Glu Ser Asp Val Asn Tyr Gln Leu Leu Gln Arg Val Thr Asn Lys Val
    50                  55                  60

Lys Leu Phe Asp Glu Glu Ala Val Leu Pro Phe Ala Lys Asn Leu Asn
65                  70                  75                  80

Arg Arg Thr Glu Arg Phe Asp Pro Arg Leu Pro Val Ala Ala Tyr Leu
                85                  90                  95

Arg Ser Leu Gln Asp Gln Tyr Ser Glu Leu Pro Gln Gly Thr Asp Leu
            100                 105                 110

Asn Asp Ile Pro Pro Leu Glu Val Ser Phe His Trp Asp Asp Trp Leu
        115                 120                 125

Ser Leu Gly Ile Ala Ser Thr Phe Trp Asp Ala Phe Asp Asn Tyr Asn
    130                 135                 140

Lys Arg Gln Gly Glu Asn Ala Ile Ser Tyr Glu Gln Leu Gln Ala Ile
145                 150                 155                 160

Leu Val Asn Asp Leu Glu Asp Phe Ser Pro Tyr Thr Ala His Ile Leu
                165                 170                 175

His Ser Asn Val Glu Val Tyr Lys Tyr Arg Thr Ile Pro Gln Lys Ile
            180                 185                 190

Val Tyr Met Ser Asn Lys Gly Tyr Phe Glu Leu Leu Val Thr Glu Lys
        195                 200                 205

Glu Lys Leu Ser Asn Glu Gly Leu Trp Ser Ile Phe His Gln Lys Gln
    210                 215                 220

Gly Gly Leu Asn Glu Phe Ser Ser Leu Asn Leu Ile Glu Glu Val Asp
```

-continued

```
            225                 230                 235                 240
Ala Leu Asp Glu Ile Tyr Asp Ser Lys Gly Leu Pro Ala Trp Asp Pro
                245                 250                 255
Pro Phe Pro Glu Glu Leu Asp Ala Ser Asp Glu Asp Phe Lys Phe Asn
                260                 265                 270
Ala Thr Glu Glu Leu Ala Lys Val Glu Gln Ile Lys Glu Pro Lys Leu
                275                 280                 285
Glu Asp Ile Phe Tyr Gln Glu Gly Leu Gln His Gly Ile Gln Thr Leu
            290                 295                 300
Pro Ser Asp Ala Ser Val Tyr Phe Pro Val Asn Tyr Val Glu Asn Asp
305                 310                 315                 320
Pro Gly Leu Gln Ser His His Leu His Phe Pro Phe Phe Ser Gly Met
                325                 330                 335
Val Leu Pro Arg Glu Ile His Ser Ser Val His His Met Asn Lys Ala
                340                 345                 350
Phe Phe Leu Phe Ala Arg Gln His Gly Tyr Val Val Trp Phe Phe Tyr
                355                 360                 365
Gly Asn Leu Ile Gly Trp Tyr Tyr Asn Gly Asn Asn His Pro Trp Asp
            370                 375                 380
Ser Asp Ile Asp Ala Ile Met Pro Met Ala Glu Met Ala Arg Met Ala
385                 390                 395                 400
His His His Asn Asn Thr Leu Ile Ile Glu Asn Pro His Asp Gly Tyr
                405                 410                 415
Gly Thr Tyr Leu Leu Thr Ile Ser Pro Trp Phe Thr Lys Lys Thr Arg
            420                 425                 430
Gly Gly Asn His Ile Asp Gly Arg Phe Val Asp Val Lys Arg Gly Thr
            435                 440                 445
Tyr Ile Asp Leu Ser Ala Ile Ser Ala Met His Gly Ile Tyr Pro Asp
            450                 455                 460
Trp Val Arg Asp Gly Val Lys Glu Asn Pro Lys Asn Leu Ala Leu Ala
465                 470                 475                 480
Asp Lys Asn Gly Asn Trp Tyr Leu Thr Arg Asp Ile Leu Pro Leu Arg
                485                 490                 495
Arg Thr Ile Phe Glu Gly Ser Arg Ser Tyr Thr Val Lys Asp Ile Glu
                500                 505                 510
Asp Thr Leu Leu Arg Asn Tyr Gly Asp Lys Val Leu Ile Asn Thr Glu
            515                 520                 525
Leu Ala Asp His Glu Trp His Asp Asp Trp Lys Met Trp Val Gln Lys
            530                 535                 540
Lys Lys Tyr Cys Thr Tyr Glu Glu Phe Glu Asp Tyr Leu Ser Ala His
545                 550                 555                 560
Gly Gly Val Glu Tyr Asp Glu Asp Gly Val Leu Thr Leu Glu Gly Ala
                565                 570                 575
Cys Gly Phe Glu Glu Val Arg Gln Asp Trp Ile Ile Thr Arg Glu Ser
                580                 585                 590
Val Asn Leu His Met Lys Glu Trp Glu Ala Ile Gln Arg Asn Glu Ser
            595                 600                 605
Thr Thr Glu Tyr Thr Ala Lys Asp Leu Pro Arg Tyr Arg Pro Asp Ser
            610                 615                 620
Phe Lys Asn Leu Leu Asp Gly Val Ser Asn His Gly Asn Gly Asn Val
625                 630                 635                 640
Gly Lys Ile Glu His Val Lys Leu Glu His Asn Asp
                645                 650
```

<210> SEQ ID NO 5
<211> LENGTH: 2292
<212> TYPE: DNA
<213> ORGANISM: Pichia pastoris

<400> SEQUENCE: 5

| | | | | | |
|---|---|---|---|---|---|
| atgagtggca | atccttttct | gttctctcct | tcaaattttg | acttttctgg | tttggatcat | 60 |
| tatagatcca | ctgataaaga | tcacttagct | ctagatgttc | tcgattatga | caaaaatcac | 120 |
| ttcttctcca | gaaactcccc | cagtttgaaa | tctcgtattc | acttttatcg | acataaattg | 180 |
| accactagaa | agcaaattgg | acttttcagc | ggcagactga | agcttttgt | gcttgctctc | 240 |
| tttgtgttga | tcacattttc | tgcaatccac | attccaatcc | ctttctcttt | ggatattcta | 300 |
| ggttcccatg | tcaaataccl | gcccttacga | gagaaagtcg | atccggaaga | ggcactccat | 360 |
| ctgcacggac | tggatctctc | ggtagcagag | ctaccttttt | tcaatgatga | catgatgtct | 420 |
| gaatttaact | acgatcctag | actacccacc | gctttgattt | tgaagttagt | gttagatcat | 480 |
| ataagtgtgc | gtaatggaac | gtttgatgct | aagtttaagg | tccccttaa | ctggaaactt | 540 |
| tgggtggatt | tgcattcaag | gttagttcca | tctaatagtt | ggtataatcg | atttcgatta | 600 |
| ccctcaggtc | gtttcgaaac | atgcgatgaa | tttaagaggt | ttttcggaat | cactaagaat | 660 |
| cactttggaa | cagaccttga | taattgcgtt | gatatcgagt | atgatactcc | ggaaggttat | 720 |
| ccaaagttca | agttttgca | tgcggaagat | aaagctcttc | cttatgaagc | acgtatcatt | 780 |
| tatggtgctt | cttaccttta | ccacgaagca | cagaatccta | aaaggttgat | attttagga | 840 |
| ttgggcaagt | ccaatgagtc | tttgatctta | ccagttgagg | caaatgacag | ttccaactta | 900 |
| atgcaattca | ccacgaata | tgcaagaagc | tttaacgatc | aacctttcgt | ttctcttgag | 960 |
| gaacttgtca | agaaggtttc | actgaccttg | aatttgaata | gtgataaggt | gctaccaatc | 1020 |
| aatgaactgg | acgttatcaa | agacaccccg | cgcttaatga | atcacaacaa | ccagggactg | 1080 |
| agcatagaca | agagctcatt | tcaatgggat | ctggaaaggg | aattacagtt | gttagaacat | 1140 |
| agaaccagtc | aagttaatga | cgtggaaggc | cttgatgcgg | gtatttattc | aacaattcaa | 1200 |
| tgtgaaatgc | gctctatgta | cgattttca | aaatacttcc | atgaatcaaa | agtctctggt | 1260 |
| aaatatcttc | cttctggaga | gcactatgac | tggcgatttt | ttaatggttt | ttacctttct | 1320 |
| cagcaggaga | atctagctgt | cctgcacagg | ttaggaagag | catggctacg | cttttctcgt | 1380 |
| gctgctggtt | tacatacatg | gattgctcac | gggacactgt | tgggttggta | ttggaatggt | 1440 |
| ctgattctgc | cgtgggatca | ggatcttgat | gttcaaatga | ctgtacaatc | attgtatctg | 1500 |
| ttgggaagga | atttcaacag | ctctcttgta | actgatgtta | gtattgaaga | tggctacagc | 1560 |
| tcagcattgg | gacattacta | tattgacgtt | ggatcctcct | tctttgttag | ggataaacta | 1620 |
| aatggtaaca | atgctataga | tgcacgtttc | gttgatactg | agaccgggtt | gtatgttgat | 1680 |
| ataactgcat | tggcttttac | agatcactta | aaactaaaac | tcactaccaa | agagaaagtt | 1740 |
| gagctacaga | aggttatgga | tccaaatgta | aggaaaaat | tgcagtggat | caaaaataaa | 1800 |
| tattcaacgg | ccacgctacc | gggtgtgata | gaaacagata | ggaataaagt | atctgatgcg | 1860 |
| ctagagaagc | aatttcatga | tttcaagttc | gacaattttg | tcaacaaaga | gttgtttcac | 1920 |
| tgtcgaaata | accatttcta | caaatatgga | gaggttggcc | gattacggag | cactatgttt | 1980 |
| gagggcgttc | ctgcccttat | accatttgaa | tttgagtcca | tactgaaacg | agaatatcct | 2040 |
| aaaggtctaa | ctttgaagca | tttctccaat | cattttggg | atccagtgaa | ccgattgtgg | 2100 |

-continued

```
gtaccagaaa agaagaaaaa aattagacac atagagtttt cacttacgaa ggaagttaca    2160
gaaagccaca agaaagaact tgcacagatc catgggaacg aaacgggtat aacctccgac    2220
ttcgcatatt ctcctttcag aatagatccc tggctgtctc gatacaggaa aaaaatgact    2280
aggagccaat aa                                                        2292
```

<210> SEQ ID NO 6
<211> LENGTH: 763
<212> TYPE: PRT
<213> ORGANISM: Pichia pastoris

<400> SEQUENCE: 6

```
Met Ser Gly Asn Pro Phe Leu Phe Ser Pro Ser Asn Phe Asp Phe Ser
1               5                   10                  15

Gly Leu Asp His Tyr Arg Ser Thr Asp Lys Asp His Leu Ala Leu Asp
                20                  25                  30

Val Leu Asp Tyr Asp Lys Asn His Phe Phe Ser Arg Asn Ser Pro Ser
            35                  40                  45

Leu Lys Ser Arg Ile His Phe Tyr Arg His Lys Leu Thr Thr Arg Lys
        50                  55                  60

Gln Ile Gly Leu Phe Ser Gly Arg Leu Lys Leu Phe Val Leu Ala Leu
65                  70                  75                  80

Phe Val Leu Ile Thr Phe Ser Ala Ile His Ile Pro Ile Pro Phe Ser
                85                  90                  95

Leu Asp Ile Leu Gly Ser His Val Lys Tyr Leu Pro Leu Arg Glu Lys
                100                 105                 110

Val Asp Pro Glu Glu Ala Leu His Leu His Gly Leu Asp Leu Ser Val
            115                 120                 125

Ala Glu Leu Pro Phe Phe Asn Asp Asp Met Met Ser Glu Phe Asn Tyr
        130                 135                 140

Asp Pro Arg Leu Pro Thr Ala Leu Ile Leu Lys Leu Val Leu Asp His
145                 150                 155                 160

Ile Ser Val Arg Asn Gly Thr Phe Asp Ala Lys Phe Lys Val Pro Phe
                165                 170                 175

Asn Trp Lys Leu Trp Val Asp Leu His Ser Arg Leu Val Pro Ser Asn
                180                 185                 190

Ser Trp Tyr Asn Arg Phe Arg Leu Pro Ser Gly Arg Phe Glu Thr Cys
            195                 200                 205

Asp Glu Phe Lys Arg Phe Gly Ile Thr Lys Asn His Phe Gly Thr
        210                 215                 220

Asp Leu Asp Asn Cys Val Asp Ile Glu Tyr Asp Thr Pro Glu Gly Tyr
225                 230                 235                 240

Pro Lys Phe Lys Val Leu His Ala Glu Asp Lys Ala Leu Pro Tyr Glu
                245                 250                 255

Ala Arg Ile Ile Tyr Gly Ala Ser Tyr Leu Tyr His Glu Ala Gln Asn
            260                 265                 270

Pro Lys Arg Leu Ile Phe Leu Gly Leu Gly Lys Ser Asn Glu Ser Leu
        275                 280                 285

Ile Leu Pro Val Glu Ala Asn Asp Ser Ser Asn Leu Met Gln Phe Asn
        290                 295                 300

His Glu Tyr Ala Arg Ser Phe Asn Asp Gln Pro Phe Val Ser Leu Glu
305                 310                 315                 320

Glu Leu Val Lys Lys Val Ser Leu Thr Leu Asn Leu Asn Ser Asp Lys
                325                 330                 335
```

```
Val Leu Pro Ile Asn Glu Leu Asp Val Ile Lys Asp Thr Pro Arg Leu
            340                 345                 350

Met Asn His Asn Asn Gln Gly Leu Ser Ile Asp Lys Ser Ser Phe Gln
            355                 360                 365

Trp Asp Leu Glu Arg Glu Leu Gln Leu Leu Glu His Arg Thr Ser Gln
            370                 375                 380

Val Asn Asp Val Glu Gly Leu Asp Ala Gly Ile Tyr Ser Thr Ile Gln
385                 390                 395                 400

Cys Glu Met Arg Ser Met Tyr Asp Phe Ser Lys Tyr Phe His Glu Ser
                405                 410                 415

Lys Val Ser Gly Lys Tyr Leu Pro Ser Gly Glu His Tyr Asp Trp Arg
                420                 425                 430

Phe Phe Asn Gly Phe Tyr Leu Ser Gln Gln Glu Asn Leu Ala Val Leu
            435                 440                 445

His Arg Leu Gly Arg Ala Trp Leu Arg Phe Ser Arg Ala Ala Gly Leu
        450                 455                 460

His Thr Trp Ile Ala His Gly Thr Leu Leu Gly Trp Tyr Trp Asn Gly
465                 470                 475                 480

Leu Ile Leu Pro Trp Asp Gln Asp Leu Asp Val Gln Met Thr Val Gln
                485                 490                 495

Ser Leu Tyr Leu Leu Gly Arg Asn Phe Asn Ser Ser Leu Val Thr Asp
            500                 505                 510

Val Ser Ile Glu Asp Gly Tyr Ser Ser Ala Leu Gly His Tyr Tyr Ile
        515                 520                 525

Asp Val Gly Ser Ser Phe Phe Val Arg Asp Lys Leu Asn Gly Asn Asn
    530                 535                 540

Ala Ile Asp Ala Arg Phe Val Asp Thr Glu Thr Gly Leu Tyr Val Asp
545                 550                 555                 560

Ile Thr Ala Leu Ala Phe Thr Asp His Leu Lys Leu Lys Leu Thr Thr
                565                 570                 575

Lys Glu Lys Val Glu Leu Gln Lys Val Met Asp Pro Asn Val Lys Glu
            580                 585                 590

Lys Leu Gln Trp Ile Lys Asn Lys Tyr Ser Thr Ala Thr Leu Pro Gly
        595                 600                 605

Val Ile Glu Thr Asp Arg Asn Lys Val Ser Asp Ala Leu Glu Lys Gln
    610                 615                 620

Phe His Asp Phe Lys Phe Asp Asn Phe Val Asn Lys Glu Leu Phe His
625                 630                 635                 640

Cys Arg Asn Asn His Phe Tyr Lys Tyr Gly Glu Val Gly Arg Leu Arg
                645                 650                 655

Ser Thr Met Phe Glu Gly Val Pro Ala Leu Ile Pro Phe Glu Phe Glu
            660                 665                 670

Ser Ile Leu Lys Arg Glu Tyr Pro Lys Gly Leu Thr Leu Lys His Phe
        675                 680                 685

Ser Asn His Phe Trp Asp Pro Val Asn Arg Leu Trp Val Pro Glu Lys
    690                 695                 700

Lys Lys Lys Ile Arg His Ile Glu Phe Ser Leu Thr Lys Glu Val Thr
705                 710                 715                 720

Glu Ser His Lys Lys Glu Leu Ala Gln Ile His Gly Asn Glu Thr Gly
                725                 730                 735

Ile Thr Ser Asp Phe Ala Tyr Ser Pro Phe Arg Ile Asp Pro Trp Leu
            740                 745                 750

Ser Arg Tyr Arg Lys Lys Met Thr Arg Ser Gln
```

```
               755                 760
```

<210> SEQ ID NO 7
<211> LENGTH: 33
<212> TYPE: DNA
<213> ORGANISM: Artificial
<220> FEATURE:
<223> OTHER INFORMATION: degenerate oligonucleotide primer

<400> SEQUENCE: 7
catagcccac tgctaagcca gaattctaat atg                          33

<210> SEQ ID NO 8
<211> LENGTH: 51
<212> TYPE: DNA
<213> ORGANISM: Artificial
<220> FEATURE:
<223> OTHER INFORMATION: degenerate oligonucleotide primer

<400> SEQUENCE: 8
gcagcgtacg aagcttcagc tagaattgta aagtgaatta tcaagtcttt c      51

<210> SEQ ID NO 9
<211> LENGTH: 52
<212> TYPE: DNA
<213> ORGANISM: Artificial
<220> FEATURE:
<223> OTHER INFORMATION: degenerate oligonucleotide primer

<400> SEQUENCE: 9
cagatccact agtggcctat gcaacaatat agcacctctc aaatacacgt tg     52

<210> SEQ ID NO 10
<211> LENGTH: 32
<212> TYPE: DNA
<213> ORGANISM: Artificial
<220> FEATURE:
<223> OTHER INFORMATION: degenerate oligonucleotide primer

<400> SEQUENCE: 10
tcttgaagta gatttggaga ttttgcgcta tg                           32

<210> SEQ ID NO 11
<211> LENGTH: 21
<212> TYPE: DNA
<213> ORGANISM: Artificial
<220> FEATURE:
<223> OTHER INFORMATION: degenerate oligonucleotide primer

<400> SEQUENCE: 11
agctgaagct tcgtacgctg c                                       21

<210> SEQ ID NO 12
<211> LENGTH: 22
<212> TYPE: DNA
<213> ORGANISM: Artificial
<220> FEATURE:
<223> OTHER INFORMATION: degenerate oligonucleotide primer

<400> SEQUENCE: 12
gcataggcca ctagtggatc tg                                      22

<210> SEQ ID NO 13
<211> LENGTH: 22
<212> TYPE: DNA
<213> ORGANISM: Artificial

```
<220> FEATURE:
<223> OTHER INFORMATION: degenerate oligonucleotide primer

<400> SEQUENCE: 13
ttcaacgagt gaccaatgta ga                                        22

<210> SEQ ID NO 14
<211> LENGTH: 45
<212> TYPE: DNA
<213> ORGANISM: Artificial
<220> FEATURE:
<223> OTHER INFORMATION: degenerate oligonucleotide primer

<400> SEQUENCE: 14
ccatccagtg tcgaaaacga gctggcgaac ttttctgggt cgaag               45

<210> SEQ ID NO 15
<211> LENGTH: 21
<212> TYPE: DNA
<213> ORGANISM: Artificial
<220> FEATURE:
<223> OTHER INFORMATION: degenerate oligonucleotide primer

<400> SEQUENCE: 15
tgaagacgtc ccctttgaac a                                         21

<210> SEQ ID NO 16
<211> LENGTH: 44
<212> TYPE: DNA
<213> ORGANISM: Artificial
<220> FEATURE:
<223> OTHER INFORMATION: degenerate oligonucleotide primer

<400> SEQUENCE: 16
acgaggcaag ctaaacagat ctagttgttt tttctatata aaac                44

<210> SEQ ID NO 17
<211> LENGTH: 45
<212> TYPE: DNA
<213> ORGANISM: Artificial
<220> FEATURE:
<223> OTHER INFORMATION: degenerate oligonucleotide primer

<400> SEQUENCE: 17
cttcgaccca gaaaagttcg ccagctcgtt ttcgacactg gatgg               45

<210> SEQ ID NO 18
<211> LENGTH: 44
<212> TYPE: DNA
<213> ORGANISM: Artificial
<220> FEATURE:
<223> OTHER INFORMATION: degenerate oligonucleotide primer

<400> SEQUENCE: 18
gttttatata gaaaaaacaa ctagatctgt ttagcttgcc tcgt                44

<210> SEQ ID NO 19
<211> LENGTH: 27
<212> TYPE: DNA
<213> ORGANISM: Artificial
<220> FEATURE:
<223> OTHER INFORMATION: degenerate oligonucleotide primer

<400> SEQUENCE: 19
tagtccaagt acgaaacgac actatcg                                   27
```

-continued

<210> SEQ ID NO 20
<211> LENGTH: 27
<212> TYPE: DNA
<213> ORGANISM: Artificial
<220> FEATURE:
<223> OTHER INFORMATION: degenerate oligonucleotide primer

<400> SEQUENCE: 20
acgacggtga gttcaaacag tttggtt                                            27

<210> SEQ ID NO 21
<211> LENGTH: 26
<212> TYPE: DNA
<213> ORGANISM: Artificial
<220> FEATURE:
<223> OTHER INFORMATION: degenerate oligonucleotide primer

<400> SEQUENCE: 21
tcgctatact gctgtcgatt cgatac                                             26

<210> SEQ ID NO 22
<211> LENGTH: 777
<212> TYPE: PRT
<213> ORGANISM: Pichia pastoris

<400> SEQUENCE: 22

```
Met Thr Leu Arg Ser Ala Ile Lys Ala Arg Thr Ser Lys Gly Leu Ile
1               5                   10                  15

Gly Ala Val Ile Ile Ala Ser Ile Ile Phe Phe Thr Thr Val Thr Phe
                20                  25                  30

Tyr Asp Glu Ser Lys Ile Val Gly Ile Ile Arg Val Ser Asp Thr Tyr
            35                  40                  45

Thr Gly His Ser Ala Val Ser Ser Thr Phe Asn Ala Ser Ser Val Val
        50                  55                  60

Ser Asp Asn Lys Ile Asn Gly Tyr Gly Leu Pro Leu Ile Asp Thr Glu
65                  70                  75                  80

Ser Asn Ser Arg Tyr Glu Asp Pro Asp Ile Ser Ile Glu Asn Glu
            85                  90                  95

Leu Arg Tyr Arg Ile Ala Gln Ser Thr Lys Glu Glu Asn Met Trp
        100                 105                 110

Lys Leu Asp Thr Thr Leu Thr Glu Ala Ser Leu Lys Ile Pro Asn Ile
        115                 120                 125

Gln Ser Phe Glu Leu Gln Pro Phe Lys Glu Arg Leu Asp Asn Ser Leu
    130                 135                 140

Tyr Asn Ser Lys Asn Ile Gly Asn Phe Tyr Phe Tyr Asp Pro Arg Leu
145                 150                 155                 160

Thr Phe Ser Val Tyr Leu Lys Tyr Ile Lys Asp Lys Leu Ala Ser Gly
                165                 170                 175

Ser Thr Thr Asn Leu Thr Ile Pro Phe Asn Trp Ala His Phe Arg Asp
            180                 185                 190

Leu Ser Ser Leu Asn Pro Tyr Leu Asp Ile Lys Gln Glu Asp Lys Val
        195                 200                 205

Ala Cys Asp Tyr Phe Tyr Glu Ser Ser Asn Lys Asp Lys Arg Lys Pro
    210                 215                 220

Thr Gly Asn Cys Ile Glu Phe Lys Asp Val Arg Asp Glu His Leu Ile
225                 230                 235                 240

Gln Tyr Gly Ile Ser Ser Lys Asp His Leu Pro Gly Pro Phe Ile Leu
                245                 250                 255
```

-continued

```
Lys Ser Leu Gly Ile Pro Met Gln His Thr Ala Lys Arg Leu Glu Ser
        260                 265                 270

Asn Leu Tyr Leu Leu Thr Gly Ala Pro Val Pro Leu Ser Leu Ser Phe
            275                 280                 285

Met Thr Lys Lys Gly Leu Tyr Gln Val Gly Val Asp Gln Thr Gly Lys
        290                 295                 300

Leu Asp Pro Asn Ile Ala Arg Thr Glu Leu Trp Glu Phe Tyr Lys Asn
305                 310                 315                 320

Gly Lys Glu Asn Leu Gln Phe Asn Ala Gln Glu Leu Ser His Leu
                325                 330                 335

Ile Glu Thr Val Pro Ser Ser Asn Ser Ser Gly Glu Gly Tyr
            340                 345                 350

Phe Thr Thr Glu Leu Lys Glu Asn Phe Glu Leu Pro Leu Ser Lys
            355                 360                 365

Asn Asp Phe Thr Phe Asp Ser Glu Val Glu Ser Leu Ile Lys Gly
        370                 375                 380

Leu Ser Glu Gln Asp Leu Asp Leu His Thr Gln Arg Tyr Lys Glu Ser
385                 390                 395                 400

Leu Gln Tyr Ser Phe Ala Thr Arg Glu Asn Asp Val Lys Lys Tyr Phe
                405                 410                 415

Tyr Glu Ala Arg Met Ile Ile Asn Thr Val Asn Lys Glu Gly Gly Ala
            420                 425                 430

His Tyr Asp Trp Arg Phe Phe Asn Gly Ala Met Asn His Glu Ser Ser
        435                 440                 445

Gly Phe Thr Glu Glu Glu Arg Gln Leu Arg Lys Arg Ser Val Leu His
    450                 455                 460

Arg Leu Leu Arg Asn Trp Leu Val Phe Asn Tyr Gln Gln Gly Ser Pro
465                 470                 475                 480

Thr Trp Leu Ala His Gly Thr Leu Leu Ser Trp Tyr Trp Asn Ser Leu
                485                 490                 495

Met Phe Pro Trp Asp Tyr Asp Ile Asp Val Gln Met Pro Ile Lys Ser
            500                 505                 510

Leu Asn Asn Leu Cys Ala Asn Phe Asn Gln Ser Leu Ile Ile Glu Asp
        515                 520                 525

Leu Thr Glu Gly Tyr Ser Ser Phe Phe Leu Asp Cys Gly Ser Ser Ile
    530                 535                 540

Thr His Arg Thr Lys Gly Lys Gly Leu Asn Phe Ile Asp Ala Arg Phe
545                 550                 555                 560

Ile Asn Val Glu Thr Gly Leu Tyr Ile Asp Ile Thr Gly Leu Ser Thr
                565                 570                 575

Ser Gln Ser Ala Arg Pro Pro Arg Phe Ser Asn Ala Ser Lys Lys Asp
            580                 585                 590

Pro Ile Tyr Asn Cys Arg Asn Asn His Phe Tyr Ser His Asn Asn Ile
        595                 600                 605

Ala Pro Leu Lys Tyr Thr Leu Met Glu Gly Val Pro Ser Phe Ile Pro
    610                 615                 620

Gln Gln Tyr Glu Glu Ile Leu Arg Glu Tyr Thr Thr Gly Leu Thr
625                 630                 635                 640

Ser Lys His Tyr Asn Gly Asn Phe Phe Met Thr Gln Leu Asn Leu Trp
                645                 650                 655

Leu Glu Arg Asp Pro Met Leu Ala Leu Val Pro Ser Ser Lys Tyr Glu
            660                 665                 670
```

```
Ile Glu Gly Gly Gly Val Asp His Asn Lys Ile Ile Lys Ser Ile Leu
            675                 680                 685

Glu Leu Ser Asn Ile Lys Lys Leu Glu Leu Leu Asp Asp Asn Pro Asp
        690                 695                 700

Ile Leu Glu Glu Val Ile Arg Thr Tyr Glu Leu Thr Ser Ile His His
705                 710                 715                 720

Lys Glu Met Gln Tyr Leu Ser Ser Val Lys Pro Asp Gly Asp Arg Ser
                725                 730                 735

Met Gln Ser Asn Asp Ile Thr Ser Ser Tyr Gln Glu Phe Leu Ala Ser
            740                 745                 750

Leu Lys Lys Phe Gln Pro Leu Arg Lys Asp Leu Phe Gln Phe Glu Arg
        755                 760                 765

Ile Asp Leu Ser Lys His Arg Lys Gln
        770                 775

<210> SEQ ID NO 23
<211> LENGTH: 1178
<212> TYPE: PRT
<213> ORGANISM: Saccharomyces cerevisiae

<400> SEQUENCE: 23

Met Leu Gln Arg Ile Ser Ser Lys Leu His Arg Arg Phe Leu Ser Gly
1               5                   10                  15

Leu Leu Arg Val Lys His Tyr Pro Leu Arg Arg Ile Leu Leu Pro Leu
            20                  25                  30

Ile Leu Leu Gln Ile Ile Ile Thr Phe Ile Trp Ser Asn Ser Pro
        35                  40                  45

Gln Arg Asn Gly Leu Gly Arg Asp Ala Asp Tyr Leu Leu Pro Asn Tyr
    50                  55                  60

Asn Glu Leu Asp Ser Asp Asp Ser Trp Tyr Ser Ile Leu Thr Ser
65                  70                  75                  80

Ser Phe Lys Asn Asp Arg Lys Ile Gln Phe Ala Lys Thr Leu Tyr Glu
                85                  90                  95

Asn Leu Lys Phe Gly Thr Asn Pro Lys Trp Val Asn Glu Tyr Thr Leu
            100                 105                 110

Gln Asn Asp Leu Leu Ser Val Lys Met Gly Pro Arg Lys Gly Ser Lys
        115                 120                 125

Leu Glu Ser Val Asp Glu Leu Lys Phe Tyr Asp Phe Asp Pro Arg Leu
    130                 135                 140

Thr Trp Ser Val Val Leu Asn His Leu Gln Asn Asn Asp Ala Asp Gln
145                 150                 155                 160

Pro Glu Lys Leu Pro Phe Ser Trp Tyr Asp Trp Thr Thr Phe His Glu
                165                 170                 175

Leu Asn Lys Leu Ile Ser Ile Asp Lys Thr Val Leu Pro Cys Asn Phe
            180                 185                 190

Leu Phe Gln Ser Ala Phe Asp Lys Glu Ser Leu Glu Ala Ile Glu Thr
        195                 200                 205

Glu Leu Gly Glu Pro Leu Phe Leu Tyr Glu Arg Pro Lys Tyr Ala Gln
    210                 215                 220

Lys Leu Trp Tyr Lys Ala Ala Arg Asn Gln Asp Arg Ile Lys Asp Ser
225                 230                 235                 240

Lys Glu Leu Lys Lys His Cys Ser Lys Leu Phe Thr Pro Asp Gly His
                245                 250                 255

Gly Ser Pro Lys Gly Leu Arg Phe Asn Thr Gln Phe Gln Ile Lys Glu
            260                 265                 270
```

-continued

Leu Tyr Asp Lys Val Arg Pro Glu Val Tyr Gln Leu Gln Ala Arg Asn
            275                 280                 285

Tyr Ile Leu Thr Thr Gln Ser His Pro Leu Ser Ile Ser Ile Ile Glu
        290                 295                 300

Ser Asp Asn Ser Thr Tyr Gln Val Pro Leu Gln Thr Glu Lys Ser Lys
305                 310                 315                 320

Asn Leu Val Gln Ser Gly Leu Leu Gln Glu Tyr Ile Asn Asp Asn Ile
                325                 330                 335

Asn Ser Thr Asn Lys Arg Lys Asn Lys Gln Asp Val Glu Phe Asn
                340                 345                 350

His Asn Arg Leu Phe Gln Glu Phe Val Asn Asn Asp Gln Val Asn Ser
            355                 360                 365

Leu Tyr Lys Leu Glu Ile Glu Glu Thr Asp Lys Phe Thr Phe Asp Lys
        370                 375                 380

Asp Leu Val Tyr Leu Ser Pro Ser Asp Phe Lys Phe Asp Ala Ser Lys
385                 390                 395                 400

Lys Ile Glu Glu Leu Glu Glu Gln Lys Lys Leu Tyr Pro Asp Lys Phe
                405                 410                 415

Ser Ala His Asn Glu Asn Tyr Leu Asn Ser Leu Lys Asn Ser Val Lys
            420                 425                 430

Thr Ser Pro Ala Leu Gln Arg Lys Phe Phe Tyr Glu Ala Gly Ala Val
        435                 440                 445

Lys Gln Tyr Lys Gly Met Gly Phe His Arg Asp Lys Arg Phe Phe Asn
    450                 455                 460

Val Asp Thr Leu Ile Asn Asp Lys Gln Glu Tyr Gln Ala Arg Leu Asn
465                 470                 475                 480

Ser Met Ile Arg Thr Phe Gln Lys Phe Thr Lys Ala Asn Gly Ile Ile
                485                 490                 495

Ser Trp Leu Ser His Gly Thr Leu Tyr Gly Tyr Leu Tyr Asn Gly Met
            500                 505                 510

Ala Phe Pro Trp Asp Asn Asp Phe Asp Leu Gln Met Pro Ile Lys His
        515                 520                 525

Leu Gln Leu Leu Ser Gln Tyr Phe Asn Gln Ser Leu Ile Leu Glu Asp
    530                 535                 540

Pro Arg Gln Gly Asn Gly Arg Tyr Phe Leu Asp Val Ser Asp Ser Leu
545                 550                 555                 560

Thr Val Arg Ile Asn Gly Asn Gly Lys Asn Asn Ile Asp Ala Arg Phe
                565                 570                 575

Ile Asp Val Asp Thr Gly Leu Tyr Ile Asp Ile Thr Gly Leu Ala Ser
            580                 585                 590

Thr Ser Ala Pro Ser Arg Asp Tyr Leu Asn Ser Tyr Ile Glu Glu Arg
        595                 600                 605

Leu Gln Glu Glu His Leu Asp Ile Asn Asn Ile Pro Glu Ser Asn Gly
    610                 615                 620

Glu Thr Ala Thr Leu Pro Asp Lys Val Asp Asp Gly Leu Val Asn Met
625                 630                 635                 640

Ala Thr Leu Asn Ile Thr Glu Leu Arg Asp Tyr Ile Thr Ser Asp Glu
                645                 650                 655

Asn Lys Asn His Lys Arg Val Pro Thr Asp Thr Asp Leu Lys Asp Leu
            660                 665                 670

Leu Lys Lys Glu Leu Glu Glu Leu Pro Lys Ser Lys Thr Ile Glu Asn
        675                 680                 685

-continued

Lys Leu Asn Pro Lys Gln Arg Tyr Phe Leu Asn Glu Lys Leu Lys Leu
    690             695             700

Tyr Asn Cys Arg Asn Asn His Phe Asn Ser Phe Glu Glu Leu Ser Pro
705             710             715             720

Leu Ile Asn Thr Val Phe His Gly Val Pro Ala Leu Ile Pro His Arg
            725             730             735

His Thr Tyr Cys Leu His Asn Glu Tyr His Val Pro Asp Arg Tyr Ala
        740             745             750

Phe Asp Ala Tyr Lys Asn Thr Ala Tyr Leu Pro Glu Phe Arg Phe Trp
    755             760             765

Phe Asp Tyr Asp Gly Leu Lys Lys Cys Ser Asn Ile Asn Ser Trp Tyr
770             775             780

Pro Asn Ile Pro Ser Ile Asn Ser Trp Asn Pro Asn Leu Leu Lys Glu
785             790             795             800

Ile Ser Ser Thr Lys Phe Glu Ser Lys Leu Phe Asp Ser Asn Lys Val
            805             810             815

Ser Glu Tyr Ser Phe Lys Asn Leu Ser Met Asp Asp Val Arg Leu Ile
        820             825             830

Tyr Lys Asn Ile Pro Lys Ala Gly Phe Ile Glu Val Phe Thr Asn Leu
    835             840             845

Tyr Asn Ser Phe Asn Val Thr Ala Tyr Arg Gln Lys Glu Leu Glu Ile
850             855             860

Gln Tyr Cys Gln Asn Leu Thr Phe Ile Glu Lys Lys Leu Leu His
865             870             875             880

Gln Leu Arg Ile Asn Val Ala Pro Lys Leu Ser Ser Pro Ala Lys Asp
            885             890             895

Pro Phe Leu Phe Gly Tyr Glu Lys Ala Met Trp Lys Asp Leu Ser Lys
        900             905             910

Ser Met Asn Gln Thr Thr Leu Asp Gln Val Thr Lys Ile Val His Glu
    915             920             925

Glu Tyr Val Gly Lys Ile Ile Asp Leu Ser Glu Ser Leu Lys Tyr Arg
930             935             940

Asn Phe Ser Leu Phe Asn Ile Thr Phe Asp Glu Thr Gly Thr Thr Leu
945             950             955             960

Asp Asp Asn Thr Glu Asp Tyr Thr Pro Ala Asn Thr Val Glu Val Asn
            965             970             975

Pro Val Asp Phe Lys Ser Asn Leu Asn Phe Ser Ser Asn Ser Phe Leu
        980             985             990

Asp Leu Asn Ser Tyr Gly Leu Asp Leu Phe Ala Pro Thr Leu Ser Asp
    995             1000            1005

Val Asn Arg Lys Gly Ile Gln Met Phe Asp Lys Asp Pro Ile Ile
    1010            1015           1020

Val Tyr Glu Asp Tyr Ala Tyr Ala Lys Leu Leu Glu Glu Arg Lys
    1025            1030           1035

Arg Arg Glu Lys Lys Lys Lys Glu Glu Glu Glu Lys Lys Lys Lys
    1040            1045           1050

Glu Glu Glu Glu Lys Lys Lys Glu Glu Glu Glu Lys Lys Lys
    1055            1060           1065

Lys Glu Glu Glu Glu Lys Lys Lys Glu Glu Glu Glu Lys Lys
    1070            1075           1080

Lys Lys Glu Glu Glu Glu Lys Lys Lys Gln Glu Glu Glu Glu Lys
    1085            1090           1095

Lys Lys Lys Glu Glu Glu Glu Lys Lys Lys Gln Glu Glu Gly Glu

```
                1100                1105                1110
Lys Met Lys Asn Glu Asp Glu Glu Asn Lys Lys Asn Glu Asp Glu
        1115                1120                1125

Glu Lys Lys Lys Asn Glu Glu Glu Glu Lys Lys Lys Gln Glu Glu
        1130                1135                1140

Lys Asn Lys Lys Asn Glu Asp Glu Glu Lys Lys Lys Gln Glu Glu
        1145                1150                1155

Glu Glu Lys Lys Lys Asn Glu Glu Glu Glu Lys Lys Lys Gln Glu
        1160                1165                1170

Glu Gly His Ser Asn
        1175

<210> SEQ ID NO 24
<211> LENGTH: 346
<212> TYPE: PRT
<213> ORGANISM: Neurospora crassa

<400> SEQUENCE: 24

Met Trp Ser Ser Leu Thr Pro Ala Arg Arg Gln Ala Thr Thr Thr Ser
1               5                   10                  15

Trp Arg Asp Arg Leu Leu Thr Leu Leu Met Ala Leu Thr Phe Val Leu
                20                  25                  30

Ser Ser Leu Ala Ser Pro Leu Pro Ile Glu Gly Ala Val Val Lys Ala
            35                  40                  45

Asn Asn Asn Asp Ala Val Ser Gln Pro Gln Ala Gln Ala Gln Ala Lys
50                  55                  60

Ala Glu Val Arg Gln Phe Ser Ala Pro Ala Gln Ala Gln Glu Ala Glu
65                  70                  75                  80

Pro Ala Thr Ala Thr Thr Ser Asp Asp Thr Thr Asn Thr Asn Thr Asp
                85                  90                  95

Asp Asp Asp Pro Leu Leu Pro Glu Arg Lys Tyr Phe His Glu Pro Gly
            100                 105                 110

Trp Thr Glu Glu Leu Ser His Tyr Asp Thr Arg Phe Phe Thr Ser Pro
        115                 120                 125

Val Pro Tyr Asp Pro His Leu Val His Leu Arg His Leu Ile Arg Ser
    130                 135                 140

Tyr Leu Leu Met Thr Ser Ser Arg Ser Leu Thr Thr Trp Leu Ala His
145                 150                 155                 160

Gly Thr Leu Leu Gly Trp Tyr Trp Asn Gly Ala Ile Met Pro Trp Asp
                165                 170                 175

Tyr Asp Leu Asp Val Gln Val Ser Asn Ile Thr Leu Gly Gln Met Ala
            180                 185                 190

Arg Asp Trp Asn Gln Thr Thr Phe Asp Tyr Val Tyr Thr Leu Ser Glu
        195                 200                 205

Glu Glu Lys Glu Gly Leu Gly Lys Gln Gly Glu Val Thr Val Lys
    210                 215                 220

Lys Tyr Leu Leu Asp Val Asn Pro Tyr Trp Ala Gln Arg Thr Arg Leu
225                 230                 235                 240

Glu Gly Met Asn Val Ile Asp Ala Arg Trp Ile Asp Met Glu Asn Gly
                245                 250                 255

Met Tyr Val Asp Ile Thr Gly Leu Ser Glu Asp Arg Glu Glu Thr Gly
            260                 265                 270

Thr Arg Gln Gly Val Trp Ser Asp Lys Asn Tyr His Gly Tyr Gly Thr
        275                 280                 285
```

```
Arg Gln Ile Trp Pro Leu Arg Arg Thr Glu Phe Glu Gly Val Glu Ala
    290                 295                 300

Trp Val Pro Trp Asp Val Glu Glu Ile Leu Lys Glu Glu Tyr Gly Val
305                 310                 315                 320

Lys Ser Leu Thr Glu Glu Ser Phe Ala Gly His Gln Phe Asp His Gly
                325                 330                 335

Arg Lys Gln Trp Val Lys Thr Glu Leu Ala
            340                 345

<210> SEQ ID NO 25
<211> LENGTH: 217
<212> TYPE: PRT
<213> ORGANISM: Neurospora crassa

<400> SEQUENCE: 25

Met Leu Leu Asn Trp Leu Leu Ile Val Thr Thr Leu Phe Pro Leu Ser
1               5                   10                  15

Thr Cys Ala Pro Ile Glu His Glu Asp Ala Ile Ala Ile Glu Gly Met
            20                  25                  30

Ala Asp Gln Lys Asp Met Ser Gly Lys Ala Gly Asp Pro Pro Gln Lys
        35                  40                  45

Tyr Phe His Glu Ser Thr Phe Ala Glu Lys Ala Leu Gly Tyr Gln Glu
    50                  55                  60

Gln Lys Ala Ala Leu Lys Asn Leu Val Arg Thr Phe Leu Glu Thr Met
65                  70                  75                  80

Arg Asp Leu Gly Ile Glu Thr Trp Leu Met His Gly Ser Leu Leu Gly
                85                  90                  95

Trp Trp Trp Asn Lys Gln Ile Met Pro Trp Asp Ser Asp Ala Asp Val
            100                 105                 110

Gln Val Thr Glu Ala Ser Met Tyr Phe Leu Ala Thr Tyr Tyr Asn Met
        115                 120                 125

Ser Val Phe His Tyr Lys Thr Pro Arg Leu Pro Ala Gly Arg Asn Tyr
    130                 135                 140

Met Leu Glu Val Asn Pro Asn Phe Ser Asn Gly Asp Gln Ser Asp Trp
145                 150                 155                 160

Leu Asn Val Ile Asp Ala Arg Trp Ile Asp Thr Glu Ser Gly Leu Phe
                165                 170                 175

Ile Asp Ile Thr Thr Ala Arg Tyr Asn Leu Thr His Pro Ala Gly Glu
            180                 185                 190

Gly Met Met Ser Cys Lys Asp Gly His Glu Phe Arg Val Thr Ile Ser
        195                 200                 205

Thr Ser Val Lys Ser Ser Gly Gly Gly
    210                 215

<210> SEQ ID NO 26
<211> LENGTH: 311
<212> TYPE: PRT
<213> ORGANISM: Aspergillus niger

<400> SEQUENCE: 26

Met His Lys Lys Ala Thr Leu Ala Leu Ala Ser Ala Ile Cys Ile Thr
1               5                   10                  15

Ala Ala Thr Gly Leu Pro Gly Pro Val Leu Asp Ser Ala Pro Lys Ala
            20                  25                  30

Ser Val His Gly Ser Val His Gly Ser Ile Leu Gly Thr Ala Ala Asp
        35                  40                  45
```

```
Ile Asn Asp Pro Ser Tyr Leu Trp Thr Met Tyr Gly Leu Asn Thr Ser
 50                  55                  60

Glu Glu Tyr Lys Tyr Phe Gln Glu Pro Gly Asn Asp Glu Ile His Ala
 65                  70                  75                  80

His Tyr Asp Ser Arg Phe Phe Lys Asp Pro Val Pro Lys Glu His Arg
                 85                  90                  95

Ser Gln Val Leu Thr His Ile Ile His Ser Tyr Phe Glu Phe Phe Asn
            100                 105                 110

Ser His Asn Leu Glu Thr Trp Leu Ala His Gly Thr Leu Leu Gly Trp
        115                 120                 125

Trp Trp Asn Gly Arg Ile Met Pro Trp Asp Trp Ile Asp Thr Gln
130                 135                 140

Val Ser Glu Ala Thr Leu Phe Arg Leu Ala Asp Glu Phe Asn Gly Thr
145                 150                 155                 160

Val Ala Gln Tyr Asn Thr Thr Asn Pro Asp Thr Gln His Ser Tyr Leu
                165                 170                 175

Leu Asp Val Asn Pro Trp Ala Arg Gln Arg Asp Arg Gly Lys Gly Leu
            180                 185                 190

Asn Ile Ile Asp Ala Arg Trp Ile Asp Met Gln Thr Gly Leu Tyr Ile
        195                 200                 205

Asp Ile Thr Gly Leu Ser Lys Leu Asn Glu Glu Lys Pro Asn Glu Trp
210                 215                 220

Gly Cys Lys Asn Asn His Asn Tyr Met Leu Ser Asp Ile Tyr Pro Leu
225                 230                 235                 240

Arg Ala Ser Phe Phe Glu Gly Val Ala Ala Lys Val Pro Tyr Arg Tyr
                245                 250                 255

Glu Ser Val Leu Ile Asp Glu Tyr Gly Glu Lys Ala Leu Ser Glu Thr
            260                 265                 270

His Tyr Asn Asp Tyr Thr Trp Val Ser Lys Gln Glu Glu Trp Val Ser
        275                 280                 285

Asp Glu Ile Ile Ala Ala Glu Lys Lys Lys Ala Lys Glu Gly Asp
290                 295                 300

Lys Asp Gly Arg Gln Tyr Glu
305                 310

<210> SEQ ID NO 27
<211> LENGTH: 261
<212> TYPE: PRT
<213> ORGANISM: Aspergillus niger

<400> SEQUENCE: 27

Met Arg Leu Ser Thr Tyr Pro Ile Leu Phe Ala Phe Cys Gly Leu Ala
  1               5                  10                  15

Ser Val Arg Gly Glu Gly Glu Ile Thr Phe Glu Asp Val Arg Asp Lys
               20                  25                  30

Leu Pro Lys Thr Tyr Ser Gly Gln Gly Gly Glu Pro Gly Pro Lys Tyr
           35                  40                  45

Phe Lys Glu Ser Ser Phe Ala Glu Ser Val Leu Pro Glu Glu Glu Thr
 50                  55                  60

Leu Pro His Leu Ser Ala Leu Ile Gln Thr Tyr Leu Ser Thr Met Ala
 65                  70                  75                  80

Asp Leu Gly Ala Glu Thr Trp Ile Met His Gly Ser Leu Leu Ala Trp
                 85                  90                  95

Trp Trp Asn Gln Lys Ile Phe Pro Trp Asp Asn Asp Leu Asp Val Gln
            100                 105                 110
```

```
Ile Asn Glu Pro Thr Ile His Phe Leu Ala Asp Tyr Tyr Asn Met Thr
            115                 120                 125

Glu His His Phe Asp Leu Pro Asp Val Glu Gly Gly Arg Thr Tyr Leu
        130                 135                 140

Leu Glu Ile Asn Pro Asn Tyr Val Val Arg Ser Lys Leu Asp Lys Ala
145                 150                 155                 160

Asn Val Ile Asp Gly Arg Trp Ile Asp Thr Ser Ser Gly Leu Phe Ile
                165                 170                 175

Asp Ile Thr Ala Val Arg Ala Asp Glu Arg Arg Ala Asn Gly Gln
            180                 185                 190

Pro Gly Ala Leu Met Cys Lys Asp Arg His Asn Phe Asp Glu Ser Glu
        195                 200                 205

Ile Tyr Pro Leu Arg Asn Ser Tyr Phe Glu Asp Val Pro Ala Lys Ile
        210                 215                 220

Pro Tyr Ala Tyr Thr Lys Leu Leu Gln Asp Glu Tyr Gly Ala Lys Ala
225                 230                 235                 240

Leu Thr Lys Thr Asn Tyr Gln Gly Cys Val Ile Leu Gln Glu Val Glu
                245                 250                 255

Phe Val Val Ser Thr
                260

<210> SEQ ID NO 28
<211> LENGTH: 997
<212> TYPE: PRT
<213> ORGANISM: Candida albicans

<400> SEQUENCE: 28

Met Ser Asn Thr Ile Pro Gln Tyr Phe Ile Arg Ile Phe Asn Leu Ile
1               5                   10                  15

Phe Ser Ala Arg Arg Lys Asn Phe Gln Leu Ala Leu Ile Ser Gly Leu
            20                  25                  30

Leu Phe Phe Gly Ser Phe Ala Ile Leu Ser Thr Thr Ser Tyr Ser Lys
        35                  40                  45

Lys Phe Asn Tyr Phe Asp Asp Leu Ile Leu Lys Ile Tyr Asp Tyr Asn
    50                  55                  60

Tyr Leu Thr Asn Asn Tyr Asn Ile Asp Tyr Leu Ala Lys Asn Asp Pro
65                  70                  75                  80

Glu Ala Tyr Phe Asn Val Lys Val Gln Gln Ile Val Asp Glu Lys Lys
                85                  90                  95

Gln His Asp Leu Glu Ser Lys Phe Trp Ser Leu Asp Thr Lys Ile Asn
            100                 105                 110

Asp Asp Gln Ala Thr Leu Gln Ile Pro Ala Tyr Phe Thr Tyr Asn Lys
        115                 120                 125

Pro Arg Asp Asn Lys Asn Leu Glu Asp Ser Glu Gln Ser Ser Lys Pro
    130                 135                 140

Val Glu Lys Pro Leu Ile Gln Pro Phe Asp Pro Arg Phe Thr Leu Ala
145                 150                 155                 160

Met Tyr Tyr Tyr Tyr Leu Asp Gln Gln Met Thr Thr Ala His His Asp
                165                 170                 175

Ser Ser Ser Ser Ser Ser Gly Asn Ser Ile Thr Val Pro Phe Asn Trp
            180                 185                 190

Tyr Asp Trp Val Asp Met Ser Val Leu Asn Lys Tyr Leu Leu Ala Pro
        195                 200                 205

Asn Lys Asp Lys Pro Asp Cys Ser Ile Leu Asp Ala His Glu Asp Ala
```

-continued

```
                210                 215                 220
Arg Lys Ile Glu Thr Glu Lys Lys Met Glu Lys Leu Ala Lys Gln
225                 230                 235                 240

Trp Asp Glu Asn Lys Arg Lys Ala Glu Glu Lys Lys Lys Ala Glu
                245                 250                 255

Glu Asp Lys Lys Glu Glu Glu Lys Lys Lys Ala Glu Glu Glu Glu
                260                 265                 270

Glu Lys Gln Arg His Glu Gln Glu Lys Gln Ala Leu Glu Glu Asp Lys
                275                 280                 285

Lys Lys Leu Glu Glu Glu Lys Lys Ile Glu Glu Lys Asn Lys
290                 295                 300

Leu Gln Glu Gln Gln Gln Gln Gln Gln Glu Glu Lys Ala Asn Asp
305                 310                 315                 320

Gly Asn Gln Glu His Ser Lys Phe Val Lys Arg Asp Glu Ile Lys
                325                 330                 335

Met Ser Thr Ser Gln Asp Lys Ser Asp Ser Asp Ala Asp Arg Ala Lys
                340                 345                 350

Ile Asp Met Thr Thr Phe Phe Asn Glu Ala Phe Glu Lys Leu Ser Asp
                355                 360                 365

Glu Asp Lys Ala Ser Val Ala Lys Asp Val Glu Asp Ala Val Lys Lys
370                 375                 380

Ile Thr Gln Pro Ser Ser Trp Cys Val Pro Asn Ala Lys Leu Ser Ile
385                 390                 395                 400

Asp His Ser Asp Lys Gln Ile Val His Pro Gly Phe Asn Val Phe Lys
                405                 410                 415

Ser Pro Gly Arg Thr Pro Gln Lys Ala Ile Ile Ala Gly Lys Ser
                420                 425                 430

Phe Leu Tyr Ser Tyr Ala Pro Pro Ser Ser Ile Leu Phe Leu Thr
                435                 440                 445

Ser Glu Gly Ser Tyr Ser Val Asn Val Gln His Ser Ala Pro Leu Leu
                450                 455                 460

Arg Asn Gly Ile Pro Glu Ser Tyr Leu Ala Asn Asn Phe Asp Val
465                 470                 475                 480

Ser Leu Asn Val Leu Gln Gln Leu His Lys Leu Lys Lys Asn His Lys
                485                 490                 495

Pro Asp Thr Ala Lys Val Ile Asn Asp Tyr Leu Leu His Ile Pro Lys
                500                 505                 510

Glu Ser Phe Lys Tyr Asp Pro Asp Ser Ile Ile Phe Asp Tyr Thr Lys
                515                 520                 525

Arg Leu Asp Lys Gly Glu Lys Leu Thr Ile Lys Glu Leu Lys Tyr Leu
530                 535                 540

Gln Ser Leu Glu Tyr Ser Lys Asp Lys Val Ala His Gly Gly Pro Pro
545                 550                 555                 560

Lys Tyr Phe Ala Glu Ser Arg Leu Ile Gly Thr Thr Val Gly Asp His
                565                 570                 575

Tyr Asp Trp Arg Phe Phe Asn Gly Val Gln Phe Gly Thr Val Asp Gln
                580                 585                 590

Ser Leu Thr Leu His Arg Leu Ile Arg Thr Trp Leu Ser Phe Thr Arg
                595                 600                 605

Lys Ser Gly Ile Thr Thr Trp Ile Ala His Gly Ser Leu Leu Ser Trp
                610                 615                 620

Tyr Trp Asn Gly Met Ala Phe Pro Trp Asp Asn Asp Ile Asp Val Gln
625                 630                 635                 640
```

-continued

Val Pro Ile Met Asp Leu His Lys Leu Ser Leu Gln Phe Asn Gln Thr
                645                 650                 655

Ile Val Val Glu Asp Pro Glu Asp Gly Phe Gly Arg Tyr Phe Leu Asp
            660                 665                 670

Ile Gly Ser Phe Ile Thr Leu Arg Glu Lys Gly Asn Gly Asn Asn Asn
        675                 680                 685

Ile Asp Ala Arg Phe Ile Asp Ile Asp Thr Gly Leu Tyr Ile Asp Ile
    690                 695                 700

Thr Ala Leu Ala Leu Ser Asn Ser Glu Thr Pro Lys Ser Asp Leu Ala
705                 710                 715                 720

Glu Leu Pro Lys Asn Phe Glu Ile Lys Asp Asn Tyr Lys Pro Ala
                725                 730                 735

Asn Glu Leu Leu Gln Ile Tyr Asn Cys Arg Asn Asn His Phe Asn Ser
                740                 745                 750

Tyr Asp Glu Leu Ser Pro Leu Met Lys Ser Ser Val Glu Gly Glu Ile
            755                 760                 765

Gly Tyr Ile Pro Ser Arg Tyr Ser Thr Ile Leu Thr Arg Glu Tyr Arg
        770                 775                 780

Ser Gly Leu Ser Ser Asn Ser His Gly Gly Tyr Ile Phe Ile Ala Lys
785                 790                 795                 800

Leu Arg Leu Trp Val Lys Glu Asp Leu Tyr Tyr Phe Ile Lys His
                805                 810                 815

Arg Asp Gln Trp Thr Lys Tyr His Ser Phe Asn Thr Lys Leu Ser Gln
            820                 825                 830

Asp Pro Ser Asn Thr Leu Leu Gln Asp Tyr Ser Tyr Leu Met Ser Glu
        835                 840                 845

Gln Glu Tyr Glu Asn Leu Gln Tyr Ser Thr Asp Leu Glu His Asp Asn
    850                 855                 860

Pro Phe Lys Lys Thr Lys Lys Pro Leu Glu Leu Lys Asn Ser Glu Leu
865                 870                 875                 880

Glu Lys Leu Lys His Met Asn Glu Ser Glu Leu Leu Gln Phe Leu Asn
                885                 890                 895

Asn Asp Asp Ile Leu Ile Gln Phe Phe Asn Ala Lys Glu Phe Thr Ser
            900                 905                 910

Phe His Glu Ser Glu Ile Met Gln Leu Thr Phe Gly Lys Ser Thr Ala
        915                 920                 925

Lys Leu Met Ser Ser Ala Ile Asp Phe Pro Pro Ile Lys Tyr Glu Pro
    930                 935                 940

Tyr Leu Tyr Lys Leu Asn His Asp Leu Asp Thr Phe Glu Asn Lys Val
945                 950                 955                 960

Asp Arg Tyr Leu Ala Leu Gln Asp Ala Tyr Gln Gln Glu His Asn Asn
                965                 970                 975

Ser Pro Ser Gly Gly Ser Asp Asn Gly Phe Met Glu Ile Glu Glu Asp
            980                 985                 990

Leu Asp Phe Ala Phe
        995

<210> SEQ ID NO 29
<211> LENGTH: 303
<212> TYPE: PRT
<213> ORGANISM: Pichia angusta

<400> SEQUENCE: 29

Met Leu Val Asn Ser Val Ser Pro Ser Lys Ser Glu Leu Asp Phe Asp

-continued

```
1               5                   10                  15
Ser Leu Phe Thr Ala Glu Lys Asn Tyr Glu Phe Val Ile Pro Pro Asp
            20                  25                  30

Arg Phe Asn Tyr Ser Tyr Asp Gln Ile Ile Glu Asn Tyr Glu Lys Arg
            35                  40                  45

Ile Asp Glu Leu Asp Glu Lys Gln Leu Arg His Leu Gln Thr Leu Lys
        50                  55                  60

Tyr Ser Arg Ser Ile Pro Ser Thr Lys Leu Lys Lys Ser Phe Arg Glu
65                      70                  75                  80

Val Asn Ile Asn Trp Pro Ala Thr Tyr Asn Gly His Lys Val Thr Glu
                85                  90                  95

Asn Gly Gly His Tyr Asp Phe Arg Phe Phe Asn Gly Phe Val Thr Glu
                100                 105                 110

Ser Lys Leu Asn Glu Tyr Asp Val Asn Glu Lys Arg Lys Ile Met
            115                 120                 125

Leu His Arg Ile Ile His Thr Trp Leu Gln Phe Thr Tyr Lys Glu Gly
        130                 135                 140

Ile Val Ser Phe Leu Ala His Gly Thr Leu Leu Ser Trp Tyr Trp Asn
145                 150                 155                 160

Ala Leu Val Phe Glu Trp Asp Asn Asp Ile Asp Val Gln Met Pro Ile
            165                 170                 175

Met Asp Phe Asp Arg Phe Cys Met Lys Tyr Asn Asn Ser Leu Ile Val
            180                 185                 190

Glu Asp Val Gln His Gly Tyr Gly Lys Tyr Tyr Val Asp Cys Gly Pro
        195                 200                 205

Tyr Pro Thr His Arg Thr Lys Gly Asn Gly Arg Asn Asn Ile Asp Ala
    210                 215                 220

Arg Phe Ile Asp Val Asp Ser Gly Met Tyr Ile Asp Ile Thr Gly Leu
225                 230                 235                 240

Ala Leu Thr Asp Thr Ile Lys Ile Pro Pro Arg Leu Glu Arg Leu Asp
            245                 250                 255

Arg Gln Arg Lys Ala Asn Asn Glu Gln Gly Lys Ser Glu Asp Ala Leu
        260                 265                 270

Pro Ala Glu Gln Thr Glu Gly Leu Ser Asp Pro Gly Ala Ser Arg Asn
    275                 280                 285

Val Lys Arg Ala Pro Val Lys Ser Asn Lys Gly Pro Glu Val Ser
    290                 295                 300
```

METHODS FOR ELIMINATING MANNOSYLPHOSPHORYLATION OF GLYCANS IN THE PRODUCTION OF GLYCOPROTEINS

CROSS-REFERENCE TO RELATED APPLICATIONS

This application claims priority to U.S. provisional application Ser. No. 60/532,461 filed on Dec. 24, 2003, which is incorporated by reference herein in its entirety.

STATEMENT AS TO FEDERALLY SPONSORED RESEARCH

This invention was funded, at least in part, under a grant from the Department of Commerce, NIST-ATP Cooperative Agreement Number 70NANB2H3046. The United States government may therefore have certain rights in the invention.

FIELD OF THE INVENTION

The present invention relates to the elimination of mannosylphosphate transfer on glycans of glycoproteins, and further relates to eliminating genes responsible for the addition of mannosylphosphate residues on glycans in yeast and filamentous fungal cells. In particular, the invention relates to engineering yeast and filamentous fungal host cells to produce glycans without mannosylphosphate residues.

BACKGROUND OF THE INVENTION

The ability to produce recombinant human proteins has led to major advances in human health care and remains an active area of drug discovery. Many therapeutic proteins require the cotranslational addition of glycans to specific asparagine residues (N-glycosylation) of the protein to ensure proper structure-function activity and subsequent stability in human serum. For therapeutic use in humans, glycoproteins require human-like N-glycosylation. Mammalian cell lines (Chinese hamster ovary (CHO) cells as well as human retinal cells) which can mimic human-like glycoprotein processing have several drawbacks including low protein titers, long fermentation times, heterogeneous products, and ongoing viral containment issues. Thus, the use of yeast and filamentous fungal expression systems having more economical processing, fewer safety obstacles and producing more robust heterologous protein yields have been heavily researched as host cells for human therapeutics.

In yeast and filamentous fungus, glycoproteins are produced having oligosaccharides which are different from those of mammalian-derived glycoproteins. Specifically in yeast, outer chain oligosaccharides are hypermannosylated consisting of 30-150 mannose residues (Kukuruzinska et al., 1987, *Annu. Rev. Biochem.* 56: 915-944). Moreover, mannosylphosphate is often transferred to both the core and outer sugar chains of glycoproteins produced in yeast (Ballou, 1990, *Methods Enzymol.* 185: 440-470). Of most consequence, is that these mannosylphosphorylated glycans from glycoproteins produced in the yeast, *Saccharomyces cerevisiae*, have been shown to illicit an immune response in rabbits (Rosenfeld and Ballou, 1974, *JBC*, 249: 2319-2321). Thus, the elimination of mannosylphosphorylation in yeast and filamentous fungi is essential for the production of non-immunogenic therapeutic glycoproteins.

In *S. cerevisiae* there are at least two genes which participate in the transfer of mannosylphosphate. The two genes, MNN4 and MNN6 have been cloned, and analyses of the gene products suggest they function in the transfer of mannosylphosphate (for review see Jigami and Odani, 1999, *Biochim. Biophys. Acta*, 1426: 333-345). MNN6 encodes a type II membrane protein homologous to the Kre2p/Mnt1p family of proteins which has been characterized as Golgi α-1,2-mannosyl-transferases involved in O-mannosylation and N-glycosylation (Lussier et al., 1997, *JBC*, 272: 15527-15531). The Δmnn6 mutant does not show a defect in the mannosylphosphorylation of the core glycans in vivo, but exhibits a decrease in mannosylphosphate transferase activity in vitro (Wang et al., 1997, *JBC*, 272: 18117-18124). Mnn4p is also a putative type II membrane protein which is 33% identical to the *S. cerevisiae* Yjr061p (Odani et al., 1996, *Glycobiology*, 6: 805-810; Hunter and Plowman, 1997, *Trends in Biochem. Sci.*, 22:18-22). Both the Δmnn6 and Δmnn4 mutants decrease the transfer of mannosylphosphate. However, the Δmnn6Δmnn4 double mutant does not further reduce this activity. These observations suggest the presence of additional mannosyltransferases that add mannosylphosphate to the core glycans.

Thus, despite the reduction of mannosylphosphorylation in *S. cerevisiae* with the disruption of MNN4, MNN6 or both in combination, there is no evidence that complete elimination of mannosylphosphate transferase activity is possible. Other genes which affect the mannosylphosphate levels have been identified in *S. cerevisiae*. These genes include PMR1, VRG4, MNN2 and MNN5. PMR1 encodes a Golgi-localized $Ca^{2+}/Mn^{2+}$-ATPase required for the normal function of the Golgi apparatus (Antebi and Fink, 1992, *Mol. Biol. Cell*, 3: 633-654); Vrg4p is involved in nucleotide-sugar transport in the Golgi (Dean et al., 1997, *JBC*, 272: 31908-31914), and Mnn2p and Mnn5p are α1,2-mannosyltransferases responsible for the initiation of branching in the outer chain of N-linked glycans (Rayner and Munro, 1998, *JBC*, 273: 23836-23843). For all four proteins, the reduction in mannosylphosphate groups attached to N-linked glycans seems to be a consequence of Golgi malfunction or a reduction in size of the N-linked glycans rather than a specific defect in the transfer activity of the mannosylphosphate groups.

Proteins expressed in the methylotrophic yeast, *Pichia pastoris* contain mannosylphosphorylated glycans (Miele, et al., 1997, *Biotech. Appl Biochem.*, 2: 79-83). Miura et al. reported the identification of the PNO1 (Phosphorylmannosylation of N-linked Oligosaccharides) gene which upon disruption confers an attenuation of mannosylphosphorylation on glycoproteins (WO 01/88143; Miura et al., 2004, *Gene*, 324: 129-137). The PNO1 gene encodes for a protein involved in the transfer of mannosylphosphate to glycans in *P. pastoris*. Its specific function, however, is unknown. As mentioned, the Δpno1 mutant decreases but does not abolish mannosylphosphorylation on N-glycans relative to a *P. pastoris* strain having wild-type Pno1p.

Currently, no methods exist to eliminate mannosylphosphorylation on glycoproteins produced in fungal hosts. A residual amount of mannosylphosphorylation on glycoproteins may still be immunogenic and, thus, is undesirable for use as human therapeutics.

What is needed, therefore, is an expression system based on yeast or filamentous fungi that produces glycoproteins which are essentially free of mannosylphosphorylated glycans.

SUMMARY OF THE INVENTION

The present invention provides a method for eliminating mannosylphosphate residues on glycans of glycoproteins in a yeast or filamentous fungal host (e.g., *P. pastoris*). The present invention also provides a fungal host which normally produces mannosylphosphorylated glycoproteins or a fraction thereof, in which the fungal host is modified to produce glycoproteins essentially free of mannosylphosphate residues. In one embodiment, the present invention provides a null mutant lacking one or more genes homologous to MNN4. In a preferred embodiment, the present invention provides a host of the genus *Pichia* comprising a disruption, deletion or mutation of mnn4B and pno1. The resulting host strain is essentially free of mannosylphosphorylation on glycans of glycoproteins.

The present invention further provides glycoprotein compositions that are essentially free of mannosylphosphorylated glycoproteins. Such glycoprotein compositions comprise complex N-glycans that may be used for therapeutic applications.

The present invention also provides isolated polynucleotides comprising or consisting of nucleic acid sequences selected from the group consisting of the coding sequences of the *P. pastoris* MNN4A, MNN4B and MNNC; nucleic acid sequences that are degenerate variants of these sequences; and related nucleic acid sequences and fragments. The invention also provides isolated polypeptides comprising or consisting of polypeptide sequences selected from the group consisting of sequences encoded by the *P. pastoris* MNN4A, MNN4B, MNN4C; related polypeptide sequences, fragments and fusions. Antibodies that specifically bind to the isolated polypeptides of the invention are also provided.

The present invention also provides host cells comprising a disruption, deletion or mutation of a nucleic acid sequence selected from the group consisting of the coding sequence of the *P. pastoris* MNN4A, MNN4B and MNNC gene, a nucleic acid sequence that is a degenerate variant of the coding sequence of the *P. pastoris* MNN4A, MNN4B and MNNC gene and related nucleic acid sequences and fragments, in which the host cells have a reduced activity of the polypeptide encoded by the nucleic acid sequence compared to a host cell without the disruption, deletion or mutation.

BRIEF DESCRIPTION OF THE DRAWINGS

FIG. 1. depicts the nucleic acid and amino acid sequence of *P. pastoris* MNN4A.

FIG. 2. depicts the nucleic acid and amino acid sequence of *P. pastoris* MNN4B.

FIG. 3. depicts the nucleic acid and amino acid sequence of *P. pastoris* MNN4C.

FIG. 6A. shows a high performance liquid chromatogram for the sample containing N-linked glycans from K3 purified from *P. pastoris* YSH-1 (Δoch1) supernatant. Glycans with mannosylphosphate elute between 20-30 mins. B. shows a high performance liquid chromatogram for a sample containing N-linked glycans from K3 purified from *P. pastoris* YAS-164 (Δoch1Δmnn4AΔpno1) supernatant. Glycans with mannosylphosphate elute between 20-30 mins. C. shows a high performance liquid chromatogram for a sample containing N-linked glycans from K3 purified from *P. pastoris* YAS-174 (Δoch1Δmnn4A Δpno1Δmnn4B) supernatant. Note the absence of mannosylphosphorylated glycans between 20 and 30 mins.

FIG. 7A. shows a high performance liquid chromatogram for the negative experimental control sample containing $H_2O$ B. shows a high performance liquid chromatogram for the sample containing N-linked glycans from erythropoietin expressed from pBK291 (His-EPO) produced in *P. pastoris* strain BK248 C. shows a high performance liquid chromatogram for the sample containing N-linked glycans from His-EPO produced in *P. pastoris* strain BK244 D. shows a high performance liquid chromatogram for the sample containing N-linked glycans from CD40 expressed from pJC33 (His-CD40) produced in *P. pastoris* strain YJC12 E. shows a high performance liquid chromatogram for the YAS252. Note: Glycans with mannosylphosphate elute between 20-30 mins.

FIG. 9 shows an alignment of MNN4/PNO1 homologs in *P. pastoris* (Pp), *S. cerevisiae* (Sc), *Neurospora crassa* (Nc), *Aspergillus nidulans* (An), *Candida albicans* (Ca) and *Pichia angusta* (*Hansenula polymorpha*) (Pa) using Clustal W from DNAStar.

DETAILED DESCRIPTION OF THE INVENTION

Figure 4:
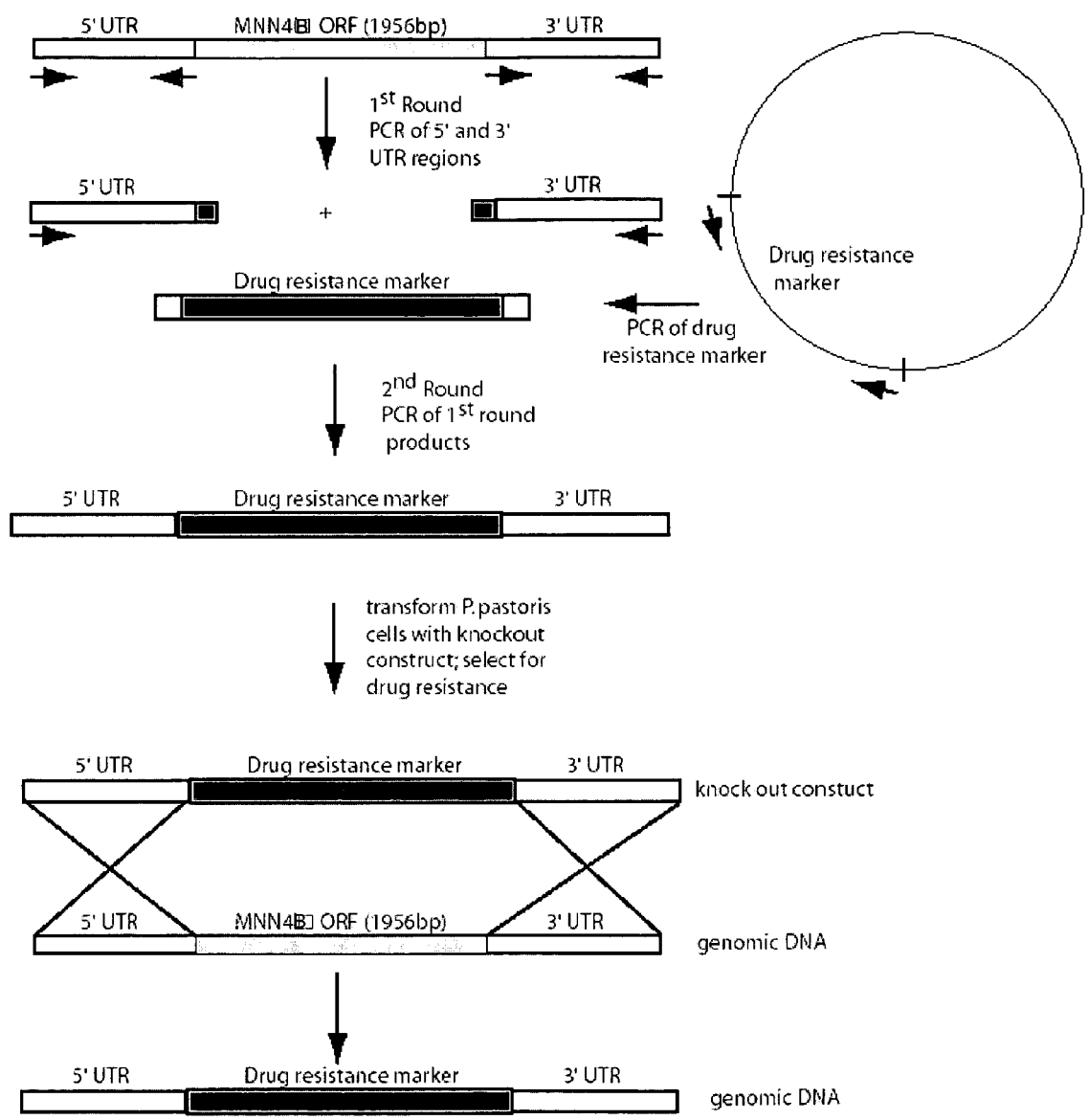
FIG. 4. illustrates the fusion PCR knock-out strategy of *P. pastoris* MNN4B using a drug resistance marker.

Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lane, *Antibodies: A Laboratory Manual*, Cold Spring Harbor Laboratory Press, Cold Spring Harbor, N.Y. (1990); Taylor and Drickamer, *Introduction to Glycobiology*, Oxford Univ. Press (2003); *Worthington Enzyme Manual*, Worthington Biochemical Corp., Freehold, N.J.;

*Handbook of Biochemistry: Section A Proteins*, Vol I, CRC Press (1976); *Handbook of Biochemistry: Section A Proteins*, Vol II, CRC Press (1976); *Essentials of Glycobiology*, Cold Spring Harbor Laboratory Press (1999).

All publications, patents and other references mentioned herein are hereby incorporated by reference in their entireties.

The following terms, unless otherwise indicated, shall be understood to have the following meanings:

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hair-pinned, circular, or in a padlocked conformation.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence is placed adjacent to the endogenous nucleic acid sequence, such that the expression of this endogenous nucleic acid sequence is altered. In this context, a heterologous sequence is a sequence that is not naturally adjacent to the endogenous nucleic acid sequence, whether or not the heterologous sequence is itself endogenous (originating from the same host cell or progeny thereof) or exogenous (originating from a different host cell or progeny thereof). By way of example, a promoter sequence can be substituted (e.g., by homologous recombination) for the native promoter of a gene in the genome of a host cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site and a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence. The term "degenerate oligonucleotide" or "degenerate primer" is used to signify an oligonucleotide capable of hybridizing with target nucleic acid sequences that are not necessarily identical in sequence but that are homologous to one another within one or more particular segments.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, *Methods Enzymol.* 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., *Molecular Cloning: A Laboratory Manual*, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

The nucleic acids (also referred to as polynucleotides) of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. Other modifications can include, for example, analogs in which the ribose ring contains a bridging moiety or other structure such as the modifications found in "locked" nucleic acids.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product; see, e.g., Leung et al., *Technique*, 1:11-15 (1989) and Caldwell and Joyce, *PCR Methods Applic.* 2:28-33 (1992)); and "oligonucleotide-directed mutagenesis" (a process which enables the generation of site-specific mutations in any cloned DNA segment of interest; see, e.g., Reidhaar-Olson and Sauer, *Science* 241:53-57 (1988)).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

The term "marker sequence" or "marker gene" refers to a nucleic acid sequence capable of expressing an activity that allows either positive or negative selection for the presence or absence of the sequence within a host cell. For example, the *P. pastoris* URA5 gene is a marker gene because its presence can be selected for by the ability of cells containing the gene to grow in the absence of uracil. Its presence can also be selected against by the inability of cells containing the gene to grow in the presence of 5-FOA. Marker sequences or genes do not necessarily need to display both positive and negative selectability. Non-limiting examples of marker sequences or genes from *P. pastoris* include ADE1, ARG4, HIS4 and URA3.

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those skilled in the art. A variety of methods for labeling polypeptides and of substituents or labels useful for such purposes are well known in the art, and include radioactive isotopes such as $^{125}$I, $^{32}$P, $^{35}$S, and $^{3}$H, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well known in the art. See, e.g., Ausubel et al., *Current Protocols in Molecular Biology*, Greene Publishing Associates (1992, and Supplements to 2002) (hereby incorporated by reference).

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusions that include the entirety of the proteins of the present invention have particular utility. The heterologous polypeptide included within the fusion protein of the present invention is at least 6 amino acids in length, often at least 8 amino acids in length, and usefully at least 15, 20, and 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

The term "non-peptide analog" refers to a compound with properties that are analogous to those of a reference polypeptide. A non-peptide compound may also be termed a "peptide mimetic" or a "peptidomimetic". See, e.g., Jones, *Amino Acid and Peptide Synthesis*, Oxford University Press (1992); Jung, *Combinatorial Peptide and Nonpeptide Libraries: A Handbook*, John Wiley (1997); Bodanszky et al., *Peptide Chemistry—A Practical Textbook*, Springer Verlag (1993); *Synthetic Peptides: A Users Guide*, (Grant, ed., W. H. Freeman and Co., 1992); Evans et al., *J. Med. Chem.* 30:1229 (1987); Fauchere, *J. Adv. Drug Res.* 15:29 (1986); Veber and Freidinger, *Trends Neurosci.*, 8:392-396 (1985); and references sited in each of the above, which are incorporated herein by reference. Such compounds are often developed with the aid of computerized molecular modeling. Peptide mimetics that are structurally similar to useful peptides of the invention may be used to produce an equivalent effect and are therefore envisioned to be part of the invention.

A "polypeptide mutant" or "mutein" refers to a polypeptide whose sequence contains an insertion, duplication, deletion, rearrangement or substitution of one or more amino acids compared to the amino acid sequence of a native or wild-type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 50% overall sequence homology to its wild-type counterpart. Even more preferred are muteins having at least 70%, 75%, 80%, 85% or 90% overall sequence homology to the wild-type protein. In an even more preferred embodiment, a mutein exhibits at least 95% sequence identity, even more preferably 98%, even more preferably 99% and even more preferably 99.9% overall sequence identity. Sequence homology may be measured by any common sequence analysis algorithm, such as Gap or Bestfit.

Amino acid substitutions can include those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* (Golub and Gren eds., Sinauer Associates, Sunderland, Mass., $2^{nd}$ ed. 1991), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γγ-carboxyglutamate, ε-N,N,N-trimethyllysine, ε-N-acetyllysine, O-phosphoserine, N-acetylserine, N-formylmethionine, 3-methylhistidine, 5-hydroxylysine, N-methylarginine, and other similar amino acids and imino acids (e.g., 4-hydroxyproline). In the polypeptide notation used herein, the left-hand end corresponds to the amino terminal end and the right-hand end corresponds to the carboxy-terminal end, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) In a preferred embodiment, a homologous protein is one that exhibits at least 65% sequence homology to the wild type protein, more preferred is at least 70% sequence homology. Even more preferred are homologous proteins that exhibit at least 75%, 80%, 85% or 90% sequence homology to the wild type protein. In a yet more preferred embodiment, a homologous protein exhibits at least 95%, 98%, 99% or 99.9% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypepitde sequence to a database containing a large number of sequences from different organisms is the computer program BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred Parameters for BLASTp are:

Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

The term "elimination" as used with respect to mannosylphosphorylation refers to mannosphosphorylated glycan detection levels indicating no apparent detectable mannosylphosphate residues using HPLC under the stated setting.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Methods for Producing a Fungal Host Strain Lacking Mannosylphosphorylation on Glycoproteins The present invention provides methods for eliminating mannosylphosphate transfer on glycans of glycoproteins in yeast or filamentous fungal host cells which normally produce glycoproteins having mannosylphosphorylation. In one embodiment, the yeast or filamentous fungal host cell which normally produces glycoproteins having mannosylphosphorylation is engineered so that it is essentially free of mannosylphosphorylation on glycans of glycoproteins. In another embodiment, the fungal hosts are genetically modified to have disrupted, attenuated or mutated at least one gene encoding a protein participating in mannosylphosphate transferase. Preferably, the method involves disruption, attenuation or mutation of one or more genes selected from MNN4A, MNN4B, MNN4C and PNO1.

Using known genes encoding mannosylphosphate transferases, novel genes encoding mannosylphosphate transferase in *P. pastoris* were isolated. The MNN4 gene sequence from *S. cerevisiae* (Genbank accession #P36044) was blasted against the genome of *P. pastoris* (Integrated Genomics, Chicago, Ill.). This search resulted in the identification of three previously unknown ORFs in addition to the PNO1 gene. The three ORFs were designated as MNN4A (SEQ ID NO: 1), MNN4B (SEQ ID NO: 3), and MNN4C (SEQ ID NO: 1). These ORFs were amplified and subsequently-sequenced and are shown respectively in FIGS. 1-3 (Example 1). The encoded amino acid sequences for MNN4A (SEQ ID NO: 2), MNN4B (SEQ ID NO: 4), MNN4C (SEQ ID NO: 6) are also set forth in FIGS. 1-3.

Nucleic Acid Sequences

In one aspect, the present invention provides a nucleic acid molecule comprising or consisting of a sequence which is a variant of the *P. pastoris* MNN4A gene having at least 50% identity to SEQ ID NO:1. The nucleic acid sequence can preferably have at least 65%, 70%, 75% or 80% identity to the wild-type gene. Even more preferably, the nucleic acid sequence can have 85%, 90%, 95%, 98%, 99%, 99.9% or even higher identity to the SEQ ID NO:1. The present invention also provides polypeptide comprising or consisting of a sequence which is a variant of the *P. pastoris* MNN4A gene having at least 50% identity to SEQ ID NO:2. The amino acid sequence can preferably have at least 65%, 70%, 75% or 80% identity to the wild-type gene. Even more preferably, the amino acid sequence can have 85%, 90%, 95%, 98%, 99%, 99.9% or even higher identity to the SEQ ID NO:2.

In another embodiment, the *P. pastoris* MNN4B gene is particularly useful in the elimination of mannosylphosphate transfer on glycans of glycoproteins in a yeast strain. The present invention provides a nucleic acid molecule comprising or consisting of a sequence which is a variant of the *P. pastoris* MNN4B gene having at least 50% identity to SEQ ID NO:3. The nucleic acid sequence can preferably have at least 65%, 70%, 75% or 80% identity to the wild-type gene. Even more preferably, the nucleic acid sequence can have 85%, 90%, 95%, 98%, 99%, 99.9% or even higher identity to the SEQ ID NO:3. The present invention also provides polypeptide comprising or consisting of a sequence which is a variant of the *P. pastoris* MNN4B gene having at least 50% identity to SEQ ID NO:4. The amino acid sequence can preferably have at least 65%, 70%, 75% or 80% identity to the wild-type gene. Even more preferably, the amino acid sequence can have 85%, 90%, 95%, 98%, 99%, 99.9% or even higher identity to the SEQ ID NO:4.

In yet another embodiment, the present invention provides a nucleic acid molecule comprising or consisting of a sequence which is a variant of the *P. pastoris* MNN4C gene having at least 50% identity to SEQ ID NO:5. The nucleic acid sequence can preferably have at least 65%, 70%, 75% or 80% identity to the wild-type gene. Even more preferably, the nucleic acid sequence can have 85%, 90%, 95%, 98%, 99%, 99.9% or even higher identity to the SEQ ID NO:5. The present invention also provides an polypeptide comprising or consisting of a sequence which is a variant of the *P. pastoris* MNN4C gene having at least 50% identity to SEQ ID NO:6. The amino acid sequence can preferably have at least 65%, 70%, 75% or 80% identity to the wild-type gene. Even more preferably, the amino acid sequence can have 85%, 90%, 95%, 98%, 99%, 99.9% or even higher identity to the SEQ ID NO:6.

Also provided are vectors, including expression vectors and knock-out vectors comprising the above nucleic acid molecules of the invention. A knock-out vector comprising a MNN4A, MNN4B or MNN4C may be used to disrupt the MNN4A, MNN4B or MNN4C gene locus. Alternatively, an integration vector comprising a drug resistance marker or an auxotrophic marker is used to disrupt the MNN4 gene locus.

Combination of Mannosylphosphorylation Gene Knockouts

Figure 5:
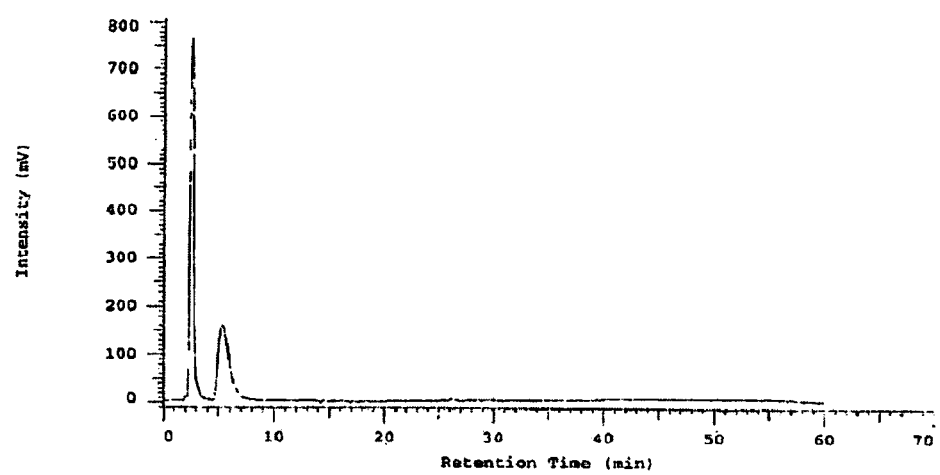
FIG. 5A. shows a high performance liquid chromatogram for the negative experimental control using $H_2O$ as the sample. B. shows a high performance liquid chromatogram for the sample containing N-linked glycans from K3 purified from *P. pastoris* YSH-44 supernatant. Glycans with mannosylphosphate elute between 20-30 mins. C. shows a high performance liquid chromatogram for a sample containing N-linked glycans from K3 purified from *P. pastoris* YSH-49 (Δpno1) supernatant. Glycans with mannosylphosphate elute between 20-30 mins. D. shows a high performance liquid chromatogram for a sample containing N-linked glycans from K3 purified from *P. pastoris* YAS-130 (Δpno1Δmnn4B) supernatant. Note the absence of mannosylphosphorylated glycans between 20 and 30 mins.

Each of the three newly identified *P. pastoris* genes, MNN4A, MNN4B, MNN4C, is disrupted using the PCR overlap strategy as shown in FIG. 4 to determine the effect on mannosylphosphorylation. The individual Δmnn4A, Δmnn4B, and Δmnn4C mutants did not show a significant decrease in mannosylphosphorylation transfer activity on glycans of the kringle 3 domain of human plasminogen (K3) protein, whereas the Δpno1mutant (YSH-49) displayed only an attenuation in mannosylphosphorylation transfer—decreased to 6% (FIG. 5C)—but not to the levels described previously in Miura et al. (WO 01/88143). It has been postulated that different glycoproteins may display varying degrees and types of glycosylation in the same host cell (Montesino et al, 1998, *Prot. Expr. Purif.* 14: 197-207). In one embodiment of the present invention, combinations of null mutants were constructed, one of which, the double mutant ΔpnoΔmnn4b in *P. pastoris* resulted in undetectable levels of mannosylphosphorylation on glycans of the K3 reporter protein (FIG. 5D). Similarly, other glycoproteins (e.g, CD40 and invertase) produced from the double mutant Δpno1Δmnn4b in *P. pastoris* also resulted in lack of mannosylphosphorylation. The double mutant, therefore, produces various glycoproteins of interest that are free of mannosylphosphorylation on glycans. Accordingly, a method is provided for disrupting a combination of genes involved in the transfer of mannosylphosphate residues on glycans of glycoproteins in a host (e.g., *Pichia* sp.). Preferably, the combination includes disruption of MNN4B and PNO1.

In case the disruption of the *P. pastoris* MNN4B locus alone does not confer elimination of mannosylphosphorylation on glycans, a combination of mannosylphosphorylation genes are disrupted. In a preferred embodiment, the disruption of the MNN4B locus is in combination with at least a second gene involved in mannosylphosphate transfer, such as MNN4A, MNN4B, MNN4C or PNO1. The second gene in this case is preferably the *P. pastoris* PNO1 gene (Genbank accession #BD105434). It is contemplated that a skilled artisan may disrupt or mutate any gene involved in oligosaccharide synthesis or a fragment thereof in combination with a disrupted or mutated MNN4B, which would result in the elimination of mannosylphosphate transfer to glycans in other fungal hosts.

In another embodiment, the method provides for disrupting a gene encoding MNN4B (SEQ ID NO: 3) in a host (e.g., *P. pastoris*) that already has attenuated mannosylphosphate transferase activity. Additionally, it is contemplated that the elimination of mannosylphosphate transfer to glycans in other *Pichia* species involves the disruption or mutation of any combination of genes having homology to MNN4A, MNN4B, MNN4C, or PNO1.

In yet another aspect of the invention each of the three newly identified *P. pastoris* genes, MNN4A, MNN4B, MNN4C, was disrupted using a fusion knock out strategy as described in Example 3 in order determine if any combination of gene knockouts had an effect on mannosylphosphorylation of glycoproteins expressed in this mutant strain. The individual Δmnn4A, Δmnn4B, and Δmnn4C mutants as with the PCR overlap knockout strategy (FIG. 4) did not show a decrease in mannosylphosphorylation transfer activity on glycans of the kringle 3 domain of human plasminogen (K3) protein (data not shown). However, the K3 reporter protein expressed in a Δpno1Δmnn4b double null mutant (YAS174) is essentially free of any mannosylphosphorylation (FIG. 6C, compare with FIG. 6A, B). Note the absence of mannosylphosphorylated glycans between 20 and 30 mins.

Heterologous Glycoprotein Expression System

Using established techniques for expressing heterologous glycoproteins in yeast and filamentous fungi, a gene encoding a therapeutic glycoprotein is expressed. A fungal recombinant protein expression system may typically include promoters such as AOX1, AOX2, or other inducible promoters, transcriptional terminators such as CYC, selectable markers such as URA3, URA5, G418, ADE1, ARG4, HIS4, Zeocin and secretion signals such as *S. cerevisiae* αMF. In one embodiment, this expression system is modified to be at least a mnn4B mutant. Preferably, the glycoproteins are produced in *P. pastoris* having at least Δmnn4B.

Glycoproteins of interest can be produced by any means through the use of the methods disclosed herein. Glycoprotein production can be provided by any means in a host cell, including accumulation in an intracellular compartment or secretion from the cell into a culture supernatant. Host cells of the present invention may be propagated or cultured by any method known or contemplated in the art, including but not limited to growth in culture tubes, flasks, roller bottles, shake flasks or fermentors. Isolation and/or purification of the glycoprotein products may be conducted by any means known or contemplated in the art such as fractionation, ion exchange, gel filtration, hydrophobic chromatography and affinity chromatography. An example of glycoprotein production and purification is disclosed in Example 7.

The glycoproteins expressed without mannosylphosphorylated glycans using the methods described herein can include but are not limited to: erythropoietin, cytokines such as interferon-α, interferon-β, interferon-γ, interferon-ω, TNF-α, granulocyte-CSF, GM-CSF, interleukins such as IL-Ira, coagulation factors such as factor VIII, factor IX, human protein C, antithrombin III and thrombopoeitin antibodies; IgG, IgA, IgD, IgE, IgM and fragments thereof, Fc and Fab regions, soluble IgE receptor α-chain, urokinase, chymase, and urea trypsin inhibitor, IGF-binding protein, epidermal growth factor, growth hormone-releasing factor, FSH, annexin V fusion protein, angiostatin, vascular endothelial growth factor-2, myeloid progenitor inhibitory factor-1, osteoprotegerin, α-1 antitrypsin, DNase II, α- feto proteins and glucocerebrosidase.

Production of Complex Glycoproteins Lacking Mannosylphosphorylation

In another aspect of the invention, the present invention provides methods for producing complex N-linked glycans in fungi and yeast (e.g., *P. pastoris*) that comprises eliminating mannosylphosphate transfer to glycans on glycoproteins. Such method provides a glycoprotein composition that is essentially free of mannosylphosphate residues on glycoproteins. In one embodiment, the invention provides less than 1% mannosylphosphorylated glycoproteins of total N-glycans. In a more preferred embodiment, the invention provides less than 0.5% mannosylphosphorylated glycoproteins of total N-glycans.

In another aspect of the present invention, the glycoprotein compositions are essentially free of mannosylphosphate residues on complex N-glycans. The method to produce such glycans involve disrupting the PNO1 and MNN4B genes in a host strain expressing complex N-glycans (e.g., *P. pastoris* YSH-44 expressing K3 reporter protein) (Hamilton et al., 2003, *Science*, 301: 1244-1246). The engineered strain comprising pno1 mnn4B disruptions, designated as YAS-130, lacks mannosylphosphate residues on glycans of glycoproteins (Example 5). Although a genetic disruption of the PNO1 gene in YSH-44 (designated YSH-49) reduces the mole % of glycans exhibiting mannosylphosphorylation (acidic fraction), mannosylphosphate residues still remain (FIG. 5C). Treatment of the glycans from YSH-44 with mild acid hydrolysis followed by alkaline phosphatase demonstrates that the acidic fraction is comprised of about 5-15% of total glycans. This YSH-49 strain shows an acidic fraction of about 6%, which does compare favorably with the about 9% acidic fraction of the YSH-44 (FIG. 5B).

By contrast, FIG. 5D shows elimination of mannosylphosphate transfer to glycans in *P. pastoris* YAS-130 (Δpno1Δmnn4B) in comparison to FIG. 5A control (H$_2$O), FIG. 5B YSH-44 with about 9% mannosylphosphorylation, and FIG. 5C YSH-49 (Δpno1) with about 6% mannosylphosphorylation. Herein is described for the first time a yeast strain engineered to be essentially free of mannosylphosphorylated glycans.

It is also contemplated that other types of yeast and filamentous fungus can be modified to lack mannosylphosphate transfer activity using the methods described herein. While *Pichia pastoris* is the preferred host strain for producing complex N-linked glycoproteins lacking mannosylphosphate residues, the following host cells may be also engineered: *Pichia finlandica, Pichia trehalophila, Pichia koclamae, Pichia membranaefaciens, Pichia methanolica, Pichia minuta (Ogataea minuta, Pichia lindneri), Pichia opuntiae, Pichia thermotolerans, Pichi salictaria, Pichia guercum, Pichia pijperi, Pichia stiptis*, and *Pichia angusta (Hansenula polymorpha)*.

Therapuetic Glycoproteins Produced in Yeast (e.g., *P. pastoris*)

Different glycoproteins may display varying degrees and types of glycosylation in the same host cell (Montesino et al, 1998). The present invention provides methods for producing various glycoproteins in a recombinant yeast strain that essentially lack mannosylphosphorylation. Preferably, the method involves engineering expression of a heterologous glycoprotein in *P. pastoris* Δpno1Δmnn4B. As such, the present invention demonstrates elimination of mannosylphosphorylation from glycans on various therapeutic glycoproteins (FIG. 7A-E, FIG. 8).

While the reporter protein K3, contains a single N-linked glycosylation site, the reporter protein His-erythropoietin (EPO) disclosed herein contains three N-linked glycosylations sites, the reporter protein His-CD40 disclosed herein contains two glycosylation sites, and the His-invertase protein disclosed herein contains up to 24 glycosylation sites. His-tagged erythropoietin (His-EPO) is expressed from *P. pastoris* strain expressing mannosylphosphorylation in FIG. 7B and a *P. pastoris* Δpno1Δmnn4B strain lacking mannosylphosphorylation in FIG. 7C. His-tagged CD40 (His-CD40) is expressed from *P. pastoris* strain expressing mannosylphosphorylation in FIG. 7D and *P. pastoris* Δpno1Δmnn4b strain lacking mannosylphosphorylation in FIG. 7E. His-tagged invertase is expressed from *P. pastoris* strain lacking mannosylphophorylation in FIG. 8. Strain construction for each of these glycoproteins is disclosed in Example 6.

Identification of MNN4 Homologs

In another aspect of the present invention, a method is provided for identifying the homologs to a MNN4 gene in any yeast preferably *Pichia* sp. or filamentous fungi. A skilled artisan can perform a BLAST database search using the amino acid sequence of MNN4A, MNN4B, MNN4C or PNO1 (Genbank accession #BD105434) against the genome of any yeast, preferably *Pichia* and obtain the homologs to any of these genes. With the identification of the MNN4/PNO1 homologs in *Pichia* yeast, one skilled in the art can subsequently disrupt or mutate any combination of these homologous genes. An alignment is shown in FIG. 9 of MNN4/PNO1 homologs in *P. pastoris, S. cerevisiae, Neurospora crassa, Aspergillus nidulans, Candida albicans* and *Pichia angusta (Hansenula polymorpha)*. Upon screening for the presence of mannosylphosphorylated glycans on proteins expressed from the *Pichia* host (Example 7), one skilled in the art can determine the gene or combination of genes, which upon disruption confer the expression of glycoproteins from the *Pichia* host which are essentially free of mannosylphosphorylation.

The disrupted genes or genes which encode for proteins participating in the transfer of mannosylphosphate to glycans of glycoproteins are preferably from a yeast strain belonging to the genus *Pichia*. Yeasts belonging to the genus *Pichia* according to the present invention include, but are not limited to: *Pichia pastoris, Pichia finlandica, Pichia trehalophila, Pichia koclamae, Pichia membranaefaciens, Pichia methanolica, Pichia minuta (Ogataea minuta, Pichia lindneri), Pichia opuntiae, Pichia thermotolerans, Pichi salictaria, Pichia guercum, Pichia pijperi, Pichia stiptis*, and *Pichia angusta (Hansenula polymorpha)*. *Pichia pastoris* is preferably used among these. Other yeast and filamentous fungi include *Saccharomyces cerevisiae, Schizosaccharomyces pombe, Saccharomyce* sp. *Hansenula polymorpha, Kluyveromyces* sp., *Candida* sp., *Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum* and *Neurospora crassa*.

The following are examples which illustrate the compositions and methods of this invention. These examples should not be construed as limiting—the examples are included for the purposes of illustration only.

EXAMPLE 1

Identification and Sequencing of MNN4A, MNN4B, MNN4C in *P. pastoris* (FIGS. 1-3)

The *Saccharomyces cerevisiae* MNN4 protein sequence (Genbank accession #P36044) was blasted against a *Pichia pastoris* genomic sequence (Integrated Genomics, Chicago, Ill.) for open reading frames encoding for proteins with homology. This search identified three ORFs with regions of homology to MNN4p. These ORFs were designated MNN4A, MNN4B and MNN4C. Each of these three genes was subsequently sequenced. The MNN4A gene was found to contain an open reading frame containing 2580 nucleotide bases coding for 860 amino acids (FIG. 1). The MNN4B gene was found to contain an open reading frame containing 1956 nucleotide bases coding for 652 amino acids (FIG. 2), and the MNN4C gene was found to contain an open reading frame containing 2289 nucleotide bases coding for 763 amino acids (FIG. 3).

EXAMPLE 2

Construction of *P. pastoris* Strains: YSH-44 and YSH-1

*P. pastoris* YSH-44 and YSH-1 were engineered from BK64-1, an Δoch1 deletion mutant secreting K3, a reporter protein with a single N-linked glycosylation site (Choi et al., 2003, *PNAS*, 100: 5022-5027; Hamilton et al., 2003, *Science*, 301: 1244-1246). YSH-1 expresses glycoproteins having predominantly GlcNAcMan$_5$GlcNAc$_2$ N-glycans and YSH-44 expresses glycoproteins having predominantly GlcNAc$_2$Man$_3$GlcNAc$_2$ N-glycans.

Deletion of PNO1 gene in YSH-44 Strain

The pno1 deletion allele (pno1::Hyg$^R$) in YSH-44 was generated by the PCR overlap method (Davidson et al., 1999, *Microbiol.* 148: 2607-2615). Primers PNK1 (5'-CAT-AGCCCACTGCTAAGCC-AGAATTCTAATATG-3') (SEQ ID NO:7) paired with PNK2 (5'-GCAGCGTACGAAGCT-TCAGCTAGAATTGTAAAGTGAATTATCAAG-TCTTTC-3') (SEQ ID NO:8), PNK3 (5'-CAGATCCAC-TAGTGGCCTATGCAACAA-TATAGCACCTCTCAAATACACGTTG-3') (SEQ ID NO:9) paired with PNK4 (5'-TCTTGAAGTAGATTTG-GAGA-TTTTGCGCTATG-3') (SEQ ID NO:10) were used to amplify the 5' and 3' flanking regions of the PNO1 gene from genomic DNA (NRRL-Y11430). Primers KAN1 (5'-AGCTGAAGCT-TCGTACGCTGC-3') (SEQ ID NO:11) paired with KAN2 (5'-GCATAGGCCACTAGTGGATCTG-3') (SEQ ID NO:12) were used to amplify the Hyg resistance marker from vector pAG32 (Goldstein and McCusker, 1999, *Yeast*, 14: 1541-1553). Primers PNK1 and PNK4 were then used in a second reaction with all three products from first round of PCR reactions to generate an overlap product. The resulting fusion PCR product was used to transform strain YSH-44, an engineered *P. pastoris* strain expressing predominantly GlcNAc2Man3GlcNAc2. Transformants were selected on YPD (1% yeast extract, 2% peptone, 2% dextrose) medium containing 200 µg/ml of hygromycin B. Proper integration of deletion allele pno1::Hyg$^R$ was confirmed by PCR. This Δpno1 strain was designated YSH-49.

EXAMPLE 3

PNO1/MNN4B Knockout Strategy in *P. Pastoris* Strain YSH-49 (FIG. 4)

YAS-130 (Δpno1Δmnn4b) double mutant strain was achieved by PCR overlap in YSH-49. The TAS54 (TTCAACGAGTGACCAATGTAGA) (SEQ ID NO: 13) and TAS51 (CCAT-CCAGTGTCGAAAACGAGCTGGC-GAACTTTTCTGGGTCGAAG) (SEQ ID NO:14) primers were used to amplify the 521 bp DNA fragment 5' of the predicted start codon from *Pichia pastoris* genomic DNA (NRRL-Y 11430). TAS51 contains a 22 bp overhang that is complimentary to the 5' end of a drug resistance marker. TAS49 (TGAAGACGTCCCCTTTGAACA) (SEQ ID NO:15) and TAS52 (ACGAGGCAAGCTAAACA-GATCTAGTTGTTTTTCTATATAAAAC) (SEQ ID NO:16) were used to amplify the 503 bp DNA fragment 3' of the predicted stop codon. TAS52 also contains a 22 bp overhang that is complimentary to the 3' end of the drug resistance marker. PCR of the drug resistance marker used pAG29 (contains pat ORF) as the DNA source (Goldstein and McCuster, 1999). The drug resistance marker was amplified using primers TAS53 (CTTCGACCCA-GAAAAGTTCGCCAGCTCG-TTTTCGACACTG-GATGG) (SEQ ID NO:17) and TAS50 (GTTTTATATAG-AAAAAACAACTAGATCTGTTTAGCTTGCCTCGT) (SEQ ID NO: 14). TAS53 has a 22 bp overhang that is complimentary to the 22 bp 5' to the predicted MNN4B start codon. TAS50 has a 22 bp overhang that is complimentary to the 22 bp 3' to the predicted MNN4B stop codon. The 5' MNN4B fragment, 3' MNN4B fragment, and the gene that confers resistance to a selectable marker were combined in an equimolar ratio and used as template DNA with primers TAS54 and TAS49 for the PCR overlap reaction.

PNO1/MNN4B Knockout Strategy in *P. pastoris* Strain YSH-1

YSH-1 was transformed by electroporation with SfiI-digested pJN503b (Δmnn4Δpno1::URA3) to yield the Δoch1Δmnn4AΔpno1 strain YAS 159. The URA3 selectable marker was recovered in this strain by 5-FOA counterselection. The resulting strain, YAS164 (Δoch1; Δmnn4AΔpno1; ura3; his4; ade1; arg4), was transformed with SfiI-digested pAS19 (Δmnn4B::URA3) giving rise to the Δoch1Δmnn4Δpno1Δmnn4B strain YAS170. The YAS170 strain was subsequently counterselected on 5-FOA to yield the strain YAS174 (Δoch1Δmnn4AΔpno1Δmnn4B; ura3; his4; ade1; arg4). YAS174 thus represents a *Pichia pastoris* strain that is deficient in mannose outer chain formation and void of mannosylphosphate on N-linked glycans.

EXAMPLE 4

PCR Amplification

An Eppendorf Mastercycler was used for all PCR reactions. PCR reactions contained template DNA, 125 µM dNTPs, 0.2 µM each of forward and reverse primer, Ex Taq polymerase buffer (Takara Bio Inc.), and Ex Taq polymerase. The DNA fragments 5' to the predicted MNN4B ORF, 3' to the predicted MNN4B ORF, and the drug resistance marker were amplified with 30 cycles of 15 sec at 97° C., 15 sec at 55° C. and 90 sec at 72° C. with an initial denaturation step of 2 min at 97° C. and a final extension step of 7 min at 72° C. PCR samples were separated by agarose gel electrophoresis and the DNA bands were extracted and purified using a Gel Extraction Kit from Qiagen. All DNA purifications were eluted in 10 mM Tris, pH 8.0 except for the final PCR (overlap of all three fragments) which was eluted in deionized H$_2$O.

EXAMPLE 5

DNA Transformations, Culture Conditions for Production of Complex Glycans in *P. pastoris* for Mannosylphosphorylation Analysis DNA for transformation was prepared by adding sodium acetate to a final concentration of 0.3 M. One hundred percent ice cold ethanol was then added to a final concentration of 70% to the DNA sample. DNA was pelleted by centrifugation (12000 g×10 min) and washed twice with 70% ice cold ethanol. The DNA was dried and then resuspended in 50 µl of 10 mM Tris, pH 8.0. YSH-49 and YAS-130 were prepared by expanding a yeast culture in BMGY (buffered minimal glycerol: 100 mM potassium phosphate, pH 6.0; 1.34% yeast nitrogen base; 4×10$^{-5}$% biotin; 1% glycerol) to an O.D. of ~2-6. The yeast were made electrocompetent by washing 3 times in 1M sorbitol and resuspending in ~1-2 mls 1M sorbitol. DNA (1-2 µg) was mixed with 100 µl of competent yeast and incubated on ice for 10 min. Yeast were then electroporated with a BTX Electrocell Manipulator 600 using the following parameters; 1.5 kV, 129 ohms, and 25 µF. One milliliter of YPDS (1% yeast extract, 2% peptone, 2% dextrose, 1M sorbitol) was added to the electroporated cells. Transformed yeast were subsequently plated on selective agar plates. Cells transformed with knockout constructs containing the hph resistance gene were spread onto YPD Y+(1% yeast extract, 2% peptone, 2% dextrose, 1.34% yeast nitrogen base without amino acids) agar plates containing 0.4 mg/ml hygromycin B. Cells transformed with knockout constructs containing the pat resistance gene were spread onto defined medium (1.34% yeast nitrogen base lacking amino acids and NH4SO$_4$, 2% dextrose, 0.1% L-proline, 4×10$^{-5}$% biotin) agar plates containing 0.6 mg/ml glufosinate. Colonies were patched onto another plate containing the same drug selection. DNA was isolated from these patches and analyzed by PCR for replacement of the wild-type MNN4B ORF with the drug resistance marker.

Screening for knockouts was performed by PCR amplification (Example 4) of both the 5' and 3' portions of the knockout construct. TAS81 (TAGTCCAAGTACGA-AAC-GACACTATCG) (SEQ ID NO:19) and TAS08 (AGCT-GCGCACGTCAAGAC-TGTCAAGG) (SEQ ID NO:20) primers were used to screen the 5' portion of the knockout construct while TAS82 (ACGACGGTGAGTTCAAA-CAGTTTGGTT) (SEQ ID NO:21) and TAS07 (TCGC-TATACTGCTGTCGATTCGATAC) (SEQ ID NO:22) primers were used to screen the 3' portion of the knockout construct. Observation of a PCR product in both screens is indicative of a successful knockout of the MNN4B ORF since primers TAS08 and TAS07 anneal at the 5' and 3' ends of the drug resistance marker sequence, respectively and TAS81 and TAS82 are complimentary to sequences in the genome that flank the 5' and 3' regions of DNA used in the knockout construct. Ninety six transformants were screened with four testing positive as an MNN4B knockout. All four Δpno1Δmnn4b strains expressed the K3 reporter protein without detectable levels of mannosylphosphate. An example of this is shown in FIG. 5D.

EXAMPLE 6

Figure 8:
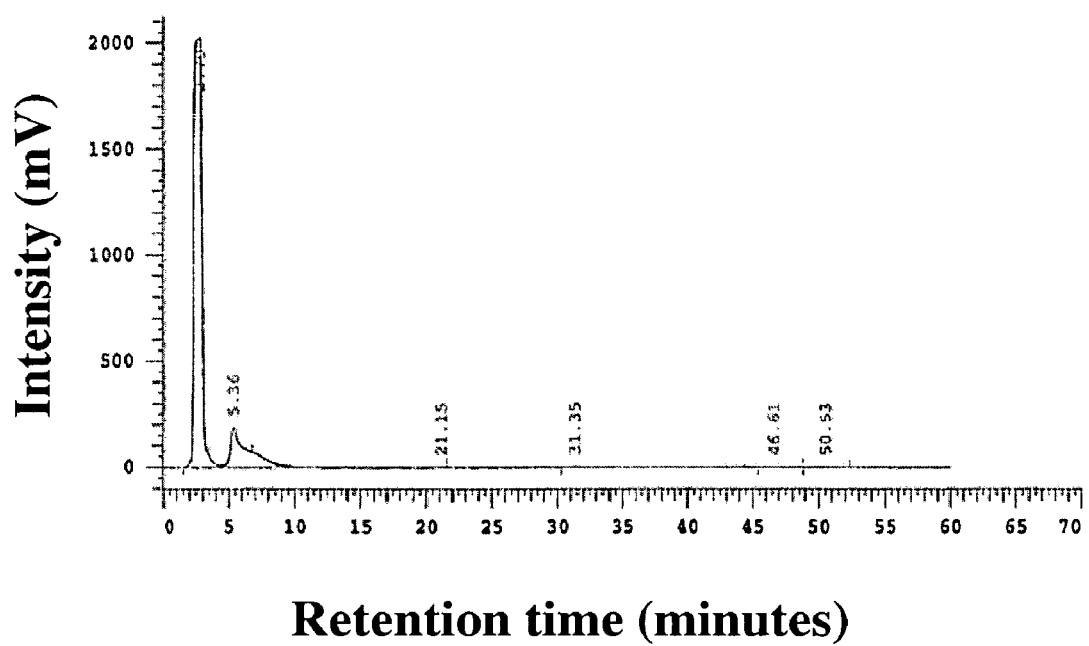
FIG. 8A shows a high performance liquid chromatogram for the sample containing N-linked glycan from invertase expressed from pPB147 produced in *P. pastoris* strain YAS252.

Strain Construction for His-Tagged EPO, CD40 and Invertase Proteins FIGS. 7, 8

For His-tagged erythropoietin (EPO), the first 166 amino acids of EPO was amplified from a human kidney cDNA library (Clontech) and inserted into the C-terminal 6His pPICZA (Invitrogen) plasmid at the EcoRI and KpnI sites. This plasmid (pBK291) was transformed into two *P. pastoris* strains, resulting in the following strains expressing EPO-6His: BK248 (ura3, his4, ade1, arg4, Δoch1::URA3) and BK244 [YSH44 transformed with pBK116 and pBK284 having the pno1mnn4b (pno1::Hyg$^R$) (mnn4b::Kan$^R$) knockouts as described and shown in Example 2, FIG. 4. pBK116 results from a 1551 bp AOX1 3'UTR DNA fragment isolated from NRRL11430 (ATCC) inserted into Invitrogen pPIC6A plasmid at the AflIII site and a 1952bp AOX1 5'UTR DNA fragment isolated from NRRL11430 inserted into the same pPIC6A plasmid at the BglII and BamHI sites with the removal of the 573 bp PmeI/BamHI DNA fragment. This pBK116 was then digested with NotI and the resulting NotI fragments were transformed into YSH44 in order to knock out the reporter K3 protein. pBK284 results from a 3196 bp DNA fragment including the AOX1 promoter, AOX1 ORF and AOX1 terminator sequence isolated from NRRL11430 (ATCC) and cloned into the multiple cloning site of the Invitrogen plasmid pCR2.1-TOPO. This plasmid was then digested with MscI and BssHI in order to delete the kanamycin gene. This resulted in pBK284 which was digested with PmeI prior to transformation into the YSH44 strain transformed with pBK116 for integration into the AOXI promoter locus. HPLC glycan analysis of EPO-6His in BK248 and BK244 is shown in FIG. 7B, C. For His-tagged CD40, the human CD40 DNA was amplified by PCR from phCD40/GemT (Pullen et al., 1999, *JBC*, 274: 14246-14254) using a 5' EcoRI primer and a 3' His10-KpnI primer for cloning into pPICZcαA resulting in pJC33. pJC33 was expressed in *P. pastoris* strain YJC12 (ura3, his4, ade1, arg4) and YAS252-2 (YAS-130 transformed with pBK116, pBK284 and pRCD465 (U.S. Ser. No. 60/562424) containing galactosyltransferase) resulting in YAS252. HPLC glycan analysis of CD49-6His in YJC12 and YAS252 is shown in FIG. 7D, E. For His-tagged-invertase, the full length invertase sequence was amplified by PCR from *Kluyveromyces lactis* genomic DNA, strain CBS683, purchased from Centraalbureau voor Schimmelcultures. The invertase ORF was amplified using blunt ended 5' and 3' primers for insertion into pPICZA plasmid (providing the C-terminal 6His tag) at the PmlI site. This pPB147 was transformed into the *P. pastoris* strain YAS245-2 (YAS130 transformed with pBK116, pBK284, and pRCD465 (U.S. Ser. No. 60/562424) resulting in YAS253. HPLC glycan analysis of invertase-6His in YAS253 is shown in FIG. 8.

EXAMPLE 7

Determination of Mannosylphosphorylation in *P. pastoris*

The extent of mannosylphosphate transfer to N-linked glycans in the strains shown in FIGS. 5-8 was determined by secreting a His-tagged reporter protein (kringle 3 protein in FIGS. 5, 6; erythropoietin protein and CD40 protein in FIG. 7 and invertase protein in FIG. 8) expressed under the control of the methanol inducible AOX1 promoter. Briefly, a shake flask containing BMGY was inoculated with a fresh yeast culture (e.g., YAS-130) and grown to an O.D. of ~20. The culture was centrifuged and the cell pellet washed with BMMY (buffered minimal methanol: same as BMGY except 0.5% methanol instead of 1% glycerol). The cell pellet was resuspended in BMMY to a volume ⅕ of the original BMGY culture and placed in a shaker for 24 h. The secreted protein was harvested by pelleting the biomass by centrifugation and transferring the culture medium to a fresh tube. The His-tagged K3, EPO, CD40 and invertase proteins were then purified on a Ni-affinity column and digested with PNGase (Choi et al., 2003). Glycan was separated from protein and then labeled with 2-amino-benzamide (2-AB). The 2-AB-labeled glycan was lyophilized, resuspended in HPLC grade water and subjected to HPLC using a GlycoSep C column (Glyco, Novato, Calif.). This analysis allows separation of neutral and acidic glycans. These glycans were determined to be phosphorylated from experiments with mild acid hydrolysis which removes the terminal mannose group, exposing the phosphate. With subsequent alkaline phosphatase treatment, the terminal phosphate group can be cleaved, leaving a neutral glycan. Successive experiments showed that phosphorylated N-linked glycans (acidic glycans) in all strains migrated between 20 and 30 minutes. Baseline conditions were assessed using dH$_2$O as a blank. The percentage of phosphorylation was calculated by dividing the acidic peak areas by the sum of the neutral and the acidic peaks. This HPLC analysis was performed under the conditions below.

HPLC Analysis

The HPLC conditions are as follows: Solvent A (acetonitrile), solvent B (500 mM ammonium acetate, 500 mM, pH 4.5) and solvent C (water). The flow rate was 0.4 mL/min for 50 min. After eluting isocratically (20% A:80% C) for 10 min a linear solvent gradient (20% A:0% B:80% C to 20% A:50% B:30% C) was employed over 30 min to elute the glycans. The column was equilibrated with solvent (20% A:80% C) for 20 min between runs.

What is claimed is:

1. A yeast of the genus *Pichia* characterized as lacking mannosyiphosphate transferase activity on glycoproteins, wherein said yeast is modified by the disruption or deletion of the MNN4B and PNO1 genes.

2. The yeast of claim 1 wherein the yeast is selected from the group consisting of: *Pichia pastoris, Pichia finlandica, Pichia trehalophila, Pichia koclamae, Pichia membranaefaciens, Pichia methanolica, Pichia minuta (Ogataea minuta, Pichia lindneri), Pichia opuntiae, Pichia thennotolerans, Pichi salictaria, Pichia guercum, Pichia pijperi,* and *Pichia stiptis.*

3. The yeast of claim 1 wherein the yeast is *P. pastoris.*

4. A modified host *Pichia* cell characterized in that the host has a disruption or deletion in the polynucleotide of SEQ ID NO:3, and thus lacks the mannosylphosphate transferase activity encoded by the polycleotide.

5. A modified host *Pichia* cell characterized in that the host does not produce a gene product having the amino acid sequence of SEQ ID NO:4, and thus lacks the mannosylnhosnhate transferase activity of the gene product.

* * * * *